United States Patent
Krantz

(10) Patent No.: US 9,545,449 B2
(45) Date of Patent: Jan. 17, 2017

(54) SITE-SPECIFIC LABELING AND TARGETED DELIVERY OF PROTEINS FOR THE TREATMENT OF CANCER

(71) Applicant: Advanced Proteome Therapeutics Inc., Boston, MA (US)

(72) Inventor: Alexander Krantz, Boston, MA (US)

(73) Assignee: Advanced Proteone Therapeutics Inc., Boston, MA (US)

(*) Notice: Subject to any disclaimer, the term of this patent is extended or adjusted under 35 U.S.C. 154(b) by 0 days.

(21) Appl. No.: 14/400,190

(22) PCT Filed: May 13, 2013

(86) PCT No.: PCT/US2013/040823
§ 371 (c)(1),
(2) Date: Nov. 10, 2014

(87) PCT Pub. No.: WO2013/170272
PCT Pub. Date: Nov. 14, 2013

(65) Prior Publication Data
US 2015/0202314 A1    Jul. 23, 2015

Related U.S. Application Data

(60) Provisional application No. 61/849,034, filed on Jan. 17, 2013, provisional application No. 61/848,601, filed on Jan. 7, 2013, provisional application No. 61/741,984, filed on Aug. 1, 2012, provisional application No. 61/688,308, filed on May 11, 2012.

(51) Int. Cl.
| | |
|---|---|
| *A61K 38/00* | (2006.01) |
| *A61K 47/48* | (2006.01) |
| *A61K 38/17* | (2006.01) |
| *A61K 38/38* | (2006.01) |
| *A61K 38/40* | (2006.01) |
| *A61K 45/06* | (2006.01) |
| *C07K 14/435* | (2006.01) |

(52) U.S. Cl.
CPC ......... *A61K 47/48246* (2013.01); *A61K 38/17* (2013.01); *A61K 38/38* (2013.01); *A61K 38/40* (2013.01); *A61K 45/06* (2013.01); *C07K 14/435* (2013.01)

(58) Field of Classification Search
None
See application file for complete search history.

(56) References Cited

U.S. PATENT DOCUMENTS

| | | |
|---|---|---|
| 5,900,404 A | 5/1999 | Gegg et al. |
| 6,017,876 A | 1/2000 | Gegg et al. |
| 6,204,247 B1 | 3/2001 | Gegg et al. |
| 6,326,468 B1 | 12/2001 | Canne et al. |
| 6,420,340 B2 | 7/2002 | Gegg et al. |
| 8,030,459 B2 | 10/2011 | Papisov et al. |
| 8,927,485 B2 | 1/2015 | Krantz et al. |
| 2003/0215877 A1 | 11/2003 | Love et al. |
| 2005/0079208 A1 | 4/2005 | Albani |
| 2007/0123465 A1 | 5/2007 | Adermann et al. |
| 2010/0099649 A1* | 4/2010 | Krantz et al. ............ 514/131 |
| 2011/0002978 A1 | 1/2011 | Harrison |
| 2011/0263832 A1 | 10/2011 | Krantz et al. |
| 2013/0165382 A1 | 6/2013 | Krantz et al. |

FOREIGN PATENT DOCUMENTS

| | | |
|---|---|---|
| WO | WO-89/11867 A1 | 12/1989 |
| WO | WO-02/42427 A2 | 5/2002 |
| WO | WO-02/087497 A2 | 11/2002 |
| WO | WO-03/093478 A1 | 11/2003 |
| WO | WO-2007/112362 A2 | 10/2007 |
| WO | WO-2010/140886 A1 | 12/2010 |
| WO | WO-2011/153250 A2 | 12/2011 |

OTHER PUBLICATIONS

Yu et al, Site-specific crosslinking of annexin proteins by 1,4-benzoquinone: a novel crosslinker for the formation of protein dimers and diverse protein conjugates (Org. Biomol. Chem., 2012, 10, 4500).*
Blanco-Canosa et al., "An efficient Fmoc-SPPS approach for the generation of thioester peptide precursors for use in native chemical ligation," Angew Chem Int Ed Engl. 47(36):6851-5 (2008) (10 pages).
Brandt et al., "Covalent attachment of proteins to polysaccharide carriers by means of benzoquinone," Biochim Biophys Acta. 386(1):196-202 (1975).
Deady et al., "Synthesis and antitumor activity of some indeno[1,2-b]quinoline-based bis carboxamides," Bioorg Med Chem. 8(5):977-84 (2000).
Dixon, "N-terminal modification of proteins—A review," J Protein Chem. 3(1):99-108 (1984).
Gentle et al., "Direct production of proteins with N-terminal cysteine for site-specific conjugation," Bioconjug Chem. 15(3):658-63 (2004).
Hauser et al., "Expressed protein ligation using an N-terminal cysteine containing fragment generated in vivo from a pelB fusion protein," Protein Expr Purif. 54(2):227-33 (2007) (13 pages).
International Preliminary Report on Patentability and Written Opinion for International Patent Application No. PCT/US2013/040823, issued Nov. 11, 2014 (15 pages).

(Continued)

*Primary Examiner* — James H Alstrum Acevedo
*Assistant Examiner* — Sergio Coffa
(74) *Attorney, Agent, or Firm* — Clark & Elbing LLP

(57) ABSTRACT

The present invention relates to the formation of protein conjugates from proteins chemically modified for linkage to (1) anticancer drug pharmacophores, (2) ligands to biomarkers on cancer cell surfaces, (3) and/or another protein molecule. It provides and specifies new compositions, methods and combinations for tumor, and tumor vasculature targeting and cancer treatment.

16 Claims, No Drawings

(56) References Cited

OTHER PUBLICATIONS

International Search Report for International Patent Application No. PCT/US13/40823, mailed Dec. 16, 2013 (8 pages).

Johnson et al., "Insights into the mechanism and catalysis of the native chemical ligation reaction," J Am Chem Soc. 128(20):6640-6 (2006).

Kalia et al., "Hydrolytic stability of hydrazones and oximes,"Angew Chem Int Ed Engl. 47(39):7523-6 (2008).

Kent, "Total chemical synthesis of proteins," Chem Soc Rev. 38(2):338-51 (2009).

Kolb et al., "Click chemistry: diverse chemical function from a few good reactions," Angew Chem Int Ed. 40(11):2004-21 (2001).

Lo Conte et al., "Photoinduced addition of glycosyl thiols to alkynyl peptides: use of free-radical thiol-yne coupling for post-translational double-glycosylation of peptides," J Org Chem. 75(13):4644-7 (2010).

Loo et al., "Biophysical characterization of zinc ejection from HIV nucleocapsid protein by anti-HIV 2,2'-dithiobis[benzamides] and benzisothiazolones," J Med Chem. 39(21):4313-20 (1996).

Niemeyer et al., "Oligonucleotide-directed self-assembly of proteins: semisynthetic DNA—streptavidin hybrid molecules as connectors for the generation of macroscopic arrays and the construction of supramolecular bioconjugates," Nucleic Acids Res. 22(25):5530-9 (1994).

Nishimura et al., "An efficient chemical method for removing N-terminal extra methionine from recombinant methionylated human growth hormone," Chem Commun. 1135-6 (1998).

Niwa et al., "A flexizyme that selectively charges amino acids activated by a water-friendly leaving group," Bioorg Med Chem Lett. 19(14):3892-4 (2009).

Radic et al., "Probing gorge dimensions of cholinesterases by freeze-frame click chemistry," Chem Biol Interact. 175(1-3):161-5 (2008) (10 pages).

Rice et al., "Inhibitors of HIV nucleocapsid protein zinc fingers as candidates for the treatment of AIDS," Science. 270(5239):1194-7 (1995).

Selden et al., "Cross-linked dimers with nucleating activity in actin prepared from muscle acetone powder," Biochemistry. 39(1):64-74 (2000).

Sunde et al., "Improved conditions for the removal of 2-oxoacyl groups from the N-terminus of proteins," Biochim Biophys Acta. 1388(1):45-52 (1998).

Tam et al., "Orthogonal ligation strategies for peptide and protein," Biopolymers. 51(5):311-32 (1999).

Wang et al., "Interaction of a self-assembling peptide with oligonucleotides: complexation and aggregation," Biophys J. 93(7):2477-90 (2007).

Wen et al., "Erythropoietin structure-function relationships: high degree of sequence homology among mammals," Blood. 82(5):1507-16 (1993).

Witus et al., "Identification of highly reactive sequences for PLP-mediated bioconjugation using a combinatorial peptide library," J Am Chem Soc. 132(47):16812-7 (2010) (14 pages).

Extended European Search Report for European Application No. 13787738.7, mailed Jul. 29, 2016 (17 pages).

Li et al., "Site-specific labeling of annexin V with F-18 for apoptosis imaging," Bioconjug Chem. 19(8):1684-8 (2008).

Green et al., "Quantitative evaluation of the lengths of homobifunctional protein cross-linking reagents used as molecular rulers," Protein Sci. 10(7):1293-304 (2001).

Supplemental Partial European Search Report for European Application No. 13787738.7, mailed Mar. 8, 2016 (12 pages).

* cited by examiner

SITE-SPECIFIC LABELING AND TARGETED DELIVERY OF PROTEINS FOR THE TREATMENT OF CANCER

CROSS-REFERENCE TO RELATED APPLICATIONS

This application is a national stage of International Patent Application No. PCT/US2013/040823, which claims benefit of U.S. Provisional Application No. 61/688,308, filed May 11, 2012, 61/741,984, filed Aug. 1, 2012, 61/848,601, filed Jan. 7, 2013, and 61/849,034, filed Jan. 17, 2013, each of which is hereby incorporated by reference in its entirety.

FIELD OF THE INVENTION

The present invention relates to the formation of protein conjugates from proteins chemically modified for linkage to (1) anticancer drug pharmacophores, (2) ligands to biomarkers on cancer cell surfaces, and/or (3) another protein molecule. It provides and specifies new compositions, methods and combinations for tumor, and tumor vasculature targeting and cancer treatment. The present invention also specifies fusion proteins that are produced recombinantly that can be utilized to link anticancer drug pharmacophores or ligands to biomarkers on cancer cell surfaces, or as therapeutics in their own right because of their increased duration of action and T-cell mediated antitumor immunity. The present invention also relates to the use of novel crosslinked proteins for targeted therapy to tumor cells. The present invention in particular relates to site-specific crosslinking of annexin proteins to various chemotherapeutic drugs or to the formation of multimeric annexin proteins that can be linked to anticancer drugs or ligands to cell surface biomarkers.

BACKGROUND OF THE INVENTION

Heightened interest in apoptosis research and the discovery of the phosphatidylserine binding properties of annexin V have stimulated developments in cell death detection technologies and annexin mediated cellular targeting.

Cancer is one of the most common causes of death, taking nearly 7 million lives each year worldwide. New cancer targeted therapies that make use of therapeutic antibodies or small molecules have made treatment more tumor specific and less toxic. Thus, targeted therapies involving anticancer drugs are vigorously being pursued with the following rationale.

Most small molecule drugs are distributed in large volumes when given intravenously. The result of such treatment is often a narrow therapeutic index due to a high level of toxicity in normal tissues. Increasing doses of chemotherapeutic agents to overcome resistance or increase efficacy most often results in toxic side effects, which generally limits the effectiveness of conventional anti-tumor agents.

Through linkage of the chemotherapeutic drug to a macromolecular carrier, such as an annexin protein, the volume of distribution of the free drug can be significantly reduced and the concentration of free drug can be directed toward and concentrated in the tumor or the tumor endothelium, resulting in a decrease in the amount and types of non-specific toxicities, and an increase in the amount of drug that can be effectively delivered to the tumor per dosed equivalent of the drug entity.

SUMMARY OF THE INVENTION

In a first aspect, the invention features a pharmaceutical composition including a therapeutic protein having a structure according to formula (I),

where
P represents a monomeric protein or a multimeric protein, where P includes 1, 2, 3, or 4 proteins independently selected from cell-targeting proteins, cell-binding proteins, cell-trafficking proteins, and transport proteins, or any combination thereof;
each L independently represents an organic linker group;
each T independently represents a therapeutic agent, a protein, or a ligand to a biomarkers;
n is an integer from 0-10; and
where each L-T moiety present is site-specifically attached to an amino acid residue of P, and
where the compound according to formula (I) represents at least about 75% of biologically active proteins present in the composition.

In some embodiments, n is an integer from 1-10.
In other embodiments, n is 0.
In certain embodiments, P represents a monomeric protein.
In still other embodiments, P represents a multimeric protein (e.g., a dimer, trimer, or tetramer).
In certain embodiments, P includes a protein that is a cell-binding protein that targets cancer cells.
In other embodiments, P includes a protein that is an annexin protein, a synaptotagmin protein, lactadherin, alpha-fetoprotein, leptin, a transferrin protein, or human serum albumin, or a protein having at least 90% sequence identity to any of said proteins.
In further embodiments, P includes a protein that is an annexin protein, a synaptotagmin protein, lactadherin, alpha-fetoprotein, leptin, a transferrin protein, or human serum albumin.
In other embodiments, P includes an annexin protein, an annexin protein including a modified amino acid residue that includes an electrophilic carbonyl, or a protein having at least 90% sequence identity to an annexin protein, and optionally said protein includes a solvent accessible thiol (e.g., a thiol where at least 75%, at least 80%, at least 85%, at least 90%, or at least 95% of the thiol is functionalized when treated with an electrophilic reagent or another reagent as described herein).
In some embodiments, P includes annexin V, annexin V-128, a protein having at least 90% sequence identity to annexin V, a protein having at least 90% sequence identity to annexin V-128, or any combination of proteins thereof.
In still other embodiments, P includes annexin V, or P includes a protein having at least 95% sequence identity to annexin V and which is not annexin V-128.
In certain embodiments, P includes annexin V-128, or P includes a protein having at least 95% sequence identity to annexin V-128 and which is not annexin V.
In other embodiments, P includes an annexin protein modified to include an RGD sequence.
In certain embodiments, P includes an annexin protein modified to include an aldehyde or ketone.

In further embodiments, P includes an annexin protein modified to include an aldehyde or ketone.

In some embodiments, P includes an annexin protein modified to include a carbonyl group on the N-terminal residue.

In still other embodiments, P includes an annexin protein modified to include an aldehyde group on the N-terminal residue.

In further embodiments, the carbonyl group can undergo reductive amination with an aromatic amine.

In still other embodiments, a L-T moiety has been covalently attached to a constituent protein of P by the reductive amination of a modified amino acid having a carbonyl functional group with an aromatic amine.

In certain embodiments, each protein present is annexin V.

In other embodiments, each protein present is annexin V-128.

In certain embodiments, where P is a dimer.

In still other embodiments, the annexin subunits are joined by a peptide linker connecting the C-terminal of one protein to the N-terminal of another.

In certain embodiments, P includes a protein that is an annexin V-128, or a protein having at least 95% sequence identity to annexin V-128 and which is not annexin V, that has a glycine at the N-terminal position, and where said protein is connected at the C-terminal to the other protein.

In further embodiments, other protein is annexin V-128, or where said other protein has at least 95% sequence identity to annexin V-128 and which is not annexin V.

In certain embodiments, n is 0.

In still other embodiments, n is 1, 2, 3, or 4.

In particular embodiments, each L is, independently, a linker group selected from the group consisting of
  C1-C20 alkylene;
  polyethylene glycol;
  a peptide having between 2-25 amino acid residues;
  a peptoid having between 2-25 residues;
  a linker formed from an α,ω-bifunctional compound, where each terminal functional group of the bifunctional compound is selected, independently, from aminooxy, hydrazine, semicarbazide, N-hydroxysuccinimide ester, maleimide, thiol, alkyne, azide, aldehyde, and alkoxylamine;
  a linker formed from a bis-anhydride, bis-imidate, or bis-carbonyl imidazole moiety; or
  a linker formed from a cycloaddition reaction between an alkyne moiety and an azide.

In further embodiments, L is, independently, a linker group selected from the group consisting of:
  a bis-aminooxyalkane $NH_2O(CH_2)_nONH_2$ where n is an integer between 1-20;
  a peptoid or peptide having between 2-15 residues, optionally said peptoid or peptide includes at least one amino acid in the D-configuration, a residue containing a thiol side chain, a residue including a nucleophilic nitrogen containing side chain, a residue having a sidechain including a hydrazine or aminooxy group, a residue having a side chain including a carboxylic acid or carboxylic ester, or any combination thereof;
  a bis-hydrazino-alkane $NH_2NH(CH_2)_nONHNH_2$ where n is an integer between 1-20;
  a bis-semicarbazide-alkane $NH_2NRCO(CH_2)_nOCN-RNH_2$ where n is an integer between 1-20;
  a linker formed from α,ω-bifunctional compound, where one terminal functional group is an azide, and the other terminal group is an aminooxy or a hydrazine;
  a 1,ω-substituted polyethylene glycol polymer including up to 1000 monomeric moieties; and
  a linker including a triazole.

In another embodiment, therapeutic protein includes one or more T groups independently selected from a chelate, protein, vitamin, enzyme, peptide, peptoid, antibody, drug, prodrug, a ligand to biomarker, and a stimulator of efferocytosis.

In a further embodiment, each T group is independently selected from a chelate, protein, vitamin, enzyme, peptide, peptoid, antibody, drug, prodrug, a ligand to biomarker, a polymer, and a stimulator of efferocytosis.

In still another embodiment, the T group is a chelate.

In certain embodiments, T includes a magnetic material (e.g., the magnetic material is paramagnetic or superparamagnetic).

In other embodiments, the T group that is vitamins, enzymes, peptides, peptoids, antibodies, drugs, prodrugs, and ligand to biomarkers, and stimulators of efferocytosis.

In still other embodiments, the T group is a ligand to a biomarker (e.g., folate, EGFR, ALK, MET, MUC-1, or KRAS).

In further embodiments, the T group is selected from the group consisting of: anthracyclines, taxols, auristatins, camptothecin, bleomycim, carboplatinums, cytarabine, 5-fluoruracil, tamoxifen, calicheimycin, maytansine, tubylysin, etoposide, a folate, and an RGD linked moiety.

In particular embodiments, said anthracycline is doxorubicin, vinblastine, vincristine; or said taxol is paclitaxel.

In still other embodiments, therapeutic protein includes a -L-T moiety, which is represented by $L_1$-$T_1$ and which is site-specifically attached to the N-terminal residue of any constituent protein of P, and where at least about 75% of the compounds according to formula (I) present in the composition have said N-terminal residue covalently attached to said $L_1$-$T_1$ moiety.

In still further embodiments, the N-terminal residue is represented by the following substructure,

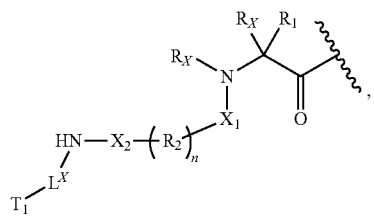

where
  both $R_X$ are H, or both $R_X$ combine to form a carbon-nitrogen double bond;
  $R_1$ is selected from the group consisting of hydrogen, optionally substituted C1-C20 alkyl and α-amino acid residue,
  $R_2$ is independently selected from the group consisting of optionally substituted C1-C20 alkyl, C2-C20 alkenyl, and C2-C20 alkynyl; $(CH_2)_q(OCH_2CH_2)_r$, where q=0-3, r=1-1000; or $(CH_2)_{1-3}$CO-Peptidyl, where the peptidyl is a chain of 1-40 α-amino acids, each of $X_1$ and $X_2$ is independently selected from the group consisting of a covalent bond, O, NR, NRCO, and NRCONR, where R is selected from the group consisting of hydrogen or is an optionally substituted group selected from C1-C10 alkyl, C2-C10 alkenyl, C2-C10 alkynyl, C6-C10 aryl, C3-C9 cycloalkyl, and three- to nine-membered heterocycloalkyl;

$L^X$ is absent or a linker covalently attached to each of $T_1$ and the amino moiety via a carbonyl.

In certain embodiments, $T_1$ is selected from the group consisting of: anthracyclines, taxols, auristatins, camptothecin, bleomycim, carboplatinums, cytarabine, 5-fluoruracil, tamoxifen, calicheimycin, maytansine, tubylysin, and etoposide.

In still other embodiments, at least about 80%, where at least about 85%, where at least about 90%, or where at least about 95% of the compounds according to formula (I) present in the composition have said N-terminal residue covalently attached to said $L_1$-$T_1$ moiety.

In further embodiments, both $R_X$ are H.

In still other embodiments, therapeutic protein includes a -L-T moiety represented by $L_2$-$T_2$ and which is site-specifically attached to a surface available thiol, or a functional group formed from surface available thiol, of any constituent protein of P, and where at least about 75% of the compounds according to formula (I) present in the composition have said surface available thiol covalently attached to said $L_2$-$T_2$ moiety.

In certain embodiments, $L_2$-$T_2$ is covalently attached to said protein via an S-propargyl functional group formed from a surface active thiol.

In still other embodiments, $L_2$-$T_2$ is covalently attached to said protein via a pendant azido moiety covalently attached to a surface active thiol.

In further embodiments, $T_2$ is either a folate or RGD linked moiety.

In still other embodiments, at least about 80%, where at least about 85%, where at least about 90%, or where at least about 95% of the compounds according to formula (I) present in the composition have said surface available thiol covalently attached to said $L_2$-$T_2$ moiety.

In particular embodiments, therapeutic protein further includes
(i) a -L-T moiety represented by $L_3$- which is site-specifically attached to the N-terminal residue of any constituent protein of P, and where at least about 75% of the compounds according to formula (I) present in the composition have said N-terminal residue covalently attached to said $L_3$-$T_3$ moiety; or
(ii) a -L-T moiety represented by $L_3$-$T_3$ which is site-specifically attached to a surface available thiol of any constituent protein of P, and where at least about 75% of the compounds according to formula (I) present in the composition have said surface available thiol that is covalent attached to said $L_3$-$T_3$ moiety.

In certain embodiments, at least about 80%, where at least about 85%, where at least about 90%, or where at least about 95% of the compounds according to formula (I) present in the composition have said N-terminal residue covalently attached to said $L_3$-$T_3$ moiety.

In other embodiments, at least about 80%, where at least about 85%, where at least about 90%, or where at least about 95% of the compounds according to formula (I) present in the composition have said surface available thiol covalently attached to said $L_3$-$T_3$ moiety.

In still another aspect, the compound according to formula (I) has the following structure,

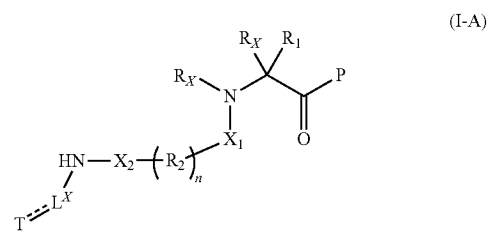

(I-A)

where
the bond between T and $L^X$ is a single bond or a double bond;
both $R_X$ are H, or both $R_X$ combine to form a carbon-nitrogen double bond;
P is selected from the group consisting of annexin proteins, synaptotagmin I, transferrin, lactadherin, α-fetoprotein and leptin, and human serum albumins.
$R_1$ is selected from the group consisting of hydrogen, optionally substituted C1-C20 alkyl and α-amino acid residue,
$R_2$ is independently selected from the group consisting of optionally substituted C1-C20 alkyl, C2-C20 alkenyl, and C2-C20 alkynyl; $(CH_2)_q(OCH_2CH_2)_r$, where q=0-3, r=1-1000; or $(CH_2)_{1-3}$CO-Peptidyl, where the peptidyl is a chain of 1-40 α-amino acids,
each of $X_1$ and $X_2$ is independently selected from the group consisting of a covalent bond, O, NR, NRCO, and NRCONR, where R is selected from the group consisting of hydrogen or is an optionally substituted group selected from C1-C10 alkyl, C2-C10 alkenyl, C2-C10 alkynyl, C6-C10 aryl, C3-C9 cycloalkyl, and three- to nin-membered heterocycloalkyl;
$L^X$ is absent, a linker covalently attached to each of T and the amino moiety via a carbonyl, or a linker attached to T via a double bond; and
T is a biologically active agent that is an anticancer drug, and, when $L^X$ is absent, T is covalently attached to the amino group via a carbonyl.

In another aspect, the invention features a compound of formula II,

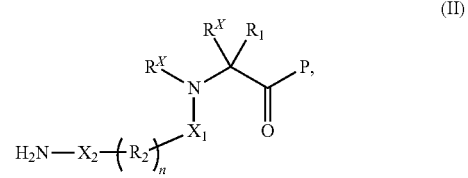

(II)

where
both $R_X$ are H, or both $R_X$ combine to form a carbon-nitrogen double bond;
P is selected from the group consisting of annexin proteins, synaptotagmin I, lactadherin, α-fetoprotein and leptin, and human serum albumins.
$R_1$ is selected from the group consisting of hydrogen, optionally substituted C1-C20 alkyl and α-amino acid residue,
$R_2$ is independently selected from the group consisting of optionally substituted C1-C20 alkyl, C2-C20 alkenyl, and C2-C20 alkynyl; $(CH_2)_q(OCH_2CH_2)_r$, where q=0-3, r=1-1000; or $(CH_2)_{1-3}$CO-Peptidyl, where the peptidyl is a chain of 1-40 α-amino acids, each of $X_1$ and $X_2$ is independently selected from the group consisting of a covalent bond, O, NR, NRCO, and NRCONR, where R is selected from the group consisting of hydrogen or is an optionally substituted group selected from C1-C10 alkyl, C2-C10 alkenyl, C2-C10 alkynyl, C6-C10 aryl, C3-C9 cycloalkyl, and three- to nine-membered heterocycloalkyl; and L is absent or a linker covalently attached to each of T and the amino moiety via a carbonyl.

In some embodiments, both $R_X$ are H.

In still other embodiments, the compound has a carbonyl group, by contacting said compound with a therapeutic agent T, thereby forming a therapeutic protein.

In another aspect the invention features a method of crosslinking drugs, ligands to biomarkers and other biologically active entities to form a therapeutic protein by (i) contacting said therapeutic agent (III) including a carbonyl group as shown,

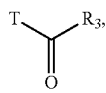

(III)

where $R_3$ is H,
with a crosslinker of compound (IV),

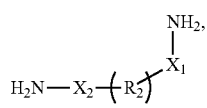

(IV)

where each of $X^1$ and $X^2$ is, independently, O, NH, or CONH;

$R_1$ is H, $CH_3$, or an amino acid side chain;

$R_2$ is optionally substituted phenyl or is $(CH_2)_m$ $(OCH_2CH_2)_p$, where m is an integer between 1-8, p is an integer between 0-1000, and P is a protein;

to form a compound having a structure according to the following formula,

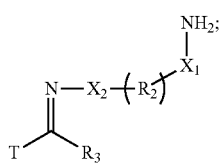

(V)

and (ii) containing the compound according to formula (V) with a protein according to formula (VI) containing a carbonyl function,

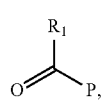

(VI)

to produce the crosslinked protein of formula (VII)

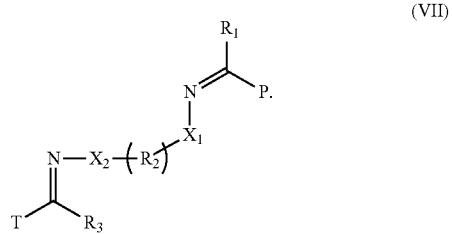

(VII)

In some embodiments, the protein of formula (VII) is optionally treated with a reducing agent to form the corresponding diamine (VII-A),

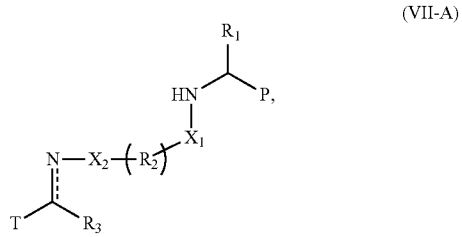

(VII-A)

wherein the bond between the nitrogen and the carbon bearing $R_3$ is a double bond or a single bond.

In still other embodiments, the protein is an annexin monomer or is an annexin multimer, and where said monomer or multimer includes a carbonyl moiety.

In particular embodiments, therapeutic agent is selected from the group consisting of: anthracyclines, taxols, auristatins, camptothecin, bleomycin, carboplatinums, cytarabine, 5-fluoruracil, tamoxifen, calicheimycin, maytansine, tubylysin, and etoposide In certain embodiments, said anthracycline is doxorubicin, vinblastine, vincristine; or said taxol is paclitaxel.

In some embodiments, the compound of structure VII is further modified at a protein cysteine function with a biologically active entity.

In still other embodiments, the biologically active entity is either a folate or RGD linked moiety.

In certain embodiments, structure (VI) is an N-terminally modified protein of structure (VIII),

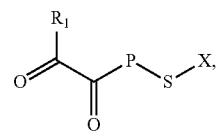

(VIII)

where X is H or a biologically active agent.

In another aspect, the invention features a method of preparing a therapeutic protein linked to two biologically active entities by condensing a protein containing a free thiol and modified to contain a ketone or aldehyde function as well (with the biologically active entities targeted for cancer cells), by first condensing the free thiol of said protein with thiol reactive substrates, and then in a further step condensing carbonyl containing drugs, (modified to contain reactive carbonyls, if necessary) for carbon-nitrogen double bond formation.

In another aspect, the invention features method of preparing a therapeutic protein linked to two biologically active entities targeted for cancer cells by first condensing carbonyl containing drugs with molecules of formula III and then contacting the protein product with thiol reactive agents.

In still another aspect, the invention features method for crosslinking entities to proteins by contacting a propargylated cysteine-containing protein of structure XII,

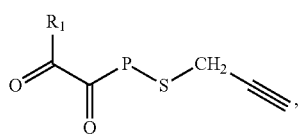

(XII)

where $R_1$ is H, $CH_3$, or an amino acid side chain, with an azide substrate (XIII),

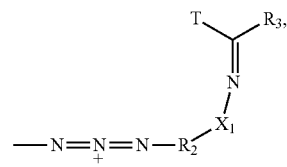

(XIII)

where $X_1$=O, NH, CONH, NHCONH; $R_2$ is $(CH_2)_m(OCH_2CH_2)_p$, where m is an integer between 1-8, p is an integer between 0-1000, T is a therapeutic agent, and $R_3$ is H or $CH_3$; to provide a compound according to formula (XIV),

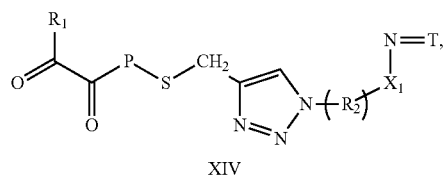

(XIV)

In some embodiments, the protein of formula (VII) is optionally treated with a reducing agent to form the corresponding diamine (XIV-A),

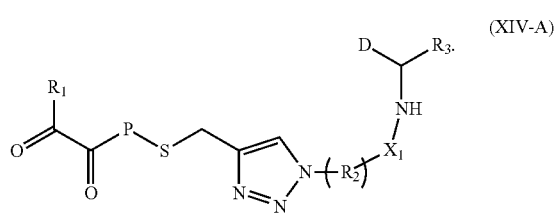

(XIV-A)

In another aspect, the invention features a method for crosslinking entities to proteins by combining a compound according to formula (XIV),

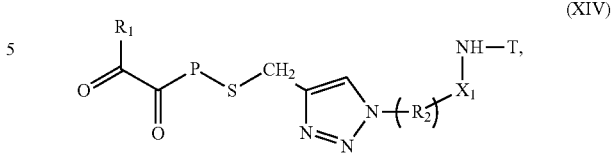

(XIV)

with a compound according to formula (XV), where $X_1$ is O, NH, CONH, or NHCONH; $R_2$ is optionally substituted phenyl or is $(CH_2)_m(OCH_2CH_2)_p$, where m is an integer between 1-8, p is an integer between 0-1000; and T is a therapeutic agent

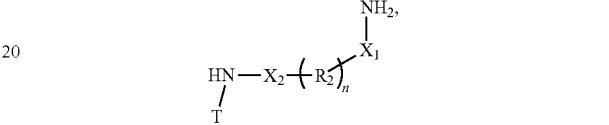

(XV)

to provide a compound according to formula (XVI),

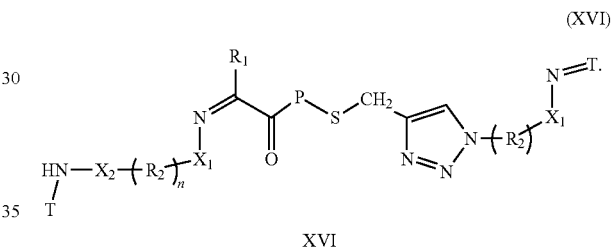

(XVI)

XVI

In still another aspect, the invention features method of crosslinking a protein to two entities by propargylating the free cysteines of a molecule of formula I and then introducing a biological entity via 1,3-cycloaddition of an azide substrate with the propargylated protein to give structures of formula (XVI).

The invention also features therapeutic protein obtained by any of the methods described herein.

In another aspect, the invention features a therapeutic protein having a structure according to formula (X).

In still another aspect, the invention features a therapeutic protein having a structure according to formula (XVI).

In another aspect, the invention features the isolated therapeutic protein as described in any of the embodiments described herein.

In some embodiments of any the methods or therapeutic proteins described herein, protein P includes an annexin, or a protein having at least 95% sequence identity to annexin V and which is not annexin V-128.

In further embodiments, P is a monomer, dimer, trimer, or tetramer.

In certain embodiments, P is diannexin; a dimer of a protein having at least 95% sequence identity to annexin V and which is not annexin V-128; a dimer of annexin V-128; or a dimer protein having at least 95% sequence identity to annexin V-128 and which is not annexin V.

In still other embodiments, protein P is a homodimeric or heterodimric annexin, and two cysteines are labeled.

In further embodiments, protein P is a homodimeric or heterodimric annexin, in which at least one annexin component is a mutant.

In some embodiments, protein P is a homodimeric or heterodimric annexin, in which at least one annexin component is a mutant and two cysteines are labeled.

In some embodiments of any the methods or therapeutic proteins described herein, each T group is, independently, selected from vitamins, enzymes, peptides, peptoids, antibodies, drugs, prodrugs, and ligand to biomarkers, and stimulators of efferocytosis.

In certain embodiments, the T group is a ligand to a biomarker.

In other embodiments, ligand is selected from the group consisting of folate, EGFR, ALK, MET, MUC-1 and KRAS.

In still other embodiments, T selected from the group consisting of: anthracyclines, taxols, auristatins, camptothecin, bleomycim, carboplatinums, cytarabine, 5-fluoruracil, tamoxifen, calicheimycin, maytansine, tubylysin, etoposide, a folate, and an RGD linked moiety.

In further embodiments, the anthracycline is doxorubicin, vinblastine, vincristine; or said taxol is paclitaxel.

In another aspect, the invention features a pharmaceutical composition including any of the therapeutic proteins described herein, where said therapeutic protein includes at least about 80% of the biologically active proteins present in the composition.

In still another aspect, the invention features a method of treating cancer in a patient, said method including administering to a patient in need thereof an effective amount of the any of the therapeutic proteins, or pharmaceutical compositions thereof, described herein.

In certain embodiments, the pharmaceutical composition includes a therapeutic protein that promotes anti-tumor immunity or promotes T-cell mediated antitumor immunity.

In still other embodiments, the effective amount of conjugated therapeutic agent T is less than the amount required by the administration of unconjugated therapeutic agent T.

In certain embodiments, the effective amount of conjugated therapeutic agent T is less than about 95, 90, 85, 80, 75, 70, 65, 60, 55, 50, 45, 40, 35, 30, or 25% of the amount required by the administration of unconjugated therapeutic agent T.

In still another aspect, the invention features method for the synthesis of a compound according to formula (X),

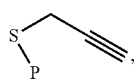
(X)

by contacting a protein P (e.g., an annexin such as annexin V or annexin V-128) having a surface available thiol with a propargylic alcohol according to formula (IX),

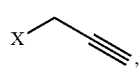
(IX)

where X is Br, Cl, R, an alkyl sulfonate, or an aryl sulfonate.

In some embodiments, the protein is annexin V-128.

In still another aspect, the invention features a method for the synthesis of a compound having formula (XII),

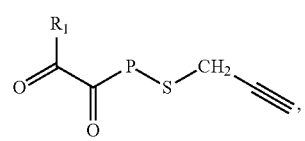
(XII)

by contacting a protein having the following structure according to formula (XI),

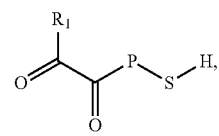
(XI)

where P represents a protein and $R_1$ is H, $CH_3$, or an amino acid side chain, with a propargylic alcohol according to formula (IX),

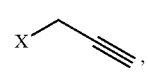
(IX)

where X is Br, Cl, R, an alkyl sulfonate, or an aryl sulfonate.

In still another aspect, the invention features a compound according to formula (XVII),

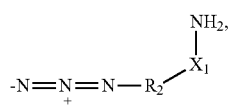
(XVII)

where $X_1$ is absent or is O, NH, CONH, NHCONH; $R_2$ is $(CH_2)_m(OCH_2CH_2)_p$, where m is an integer between 1-8 and p is an integer between 0-1000.

In a further aspect, the invention features a compound according to formula (XVIII),

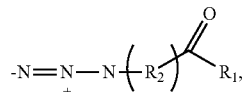
(XVIII)

where $R_1$ is H, C1-C20 alkyl, C6-C10 aryl, C2-C20 alkenyl, or OH; and $R_2$ is $(CH_2)_m(OCH_2CH_2)_p$, where m is an integer between 1-8 and p is an integer between 0-1000.

In another aspect, the invention features a compound according to formula (XIX),

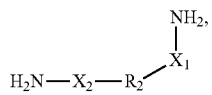
(XIX)

where
 $X_1$ is O, NH, or CONH;
 $X_2$ is absent or is O, NH, or CONH;
 $R_1$ is H, $CH_3$, or an amino acid side chain; and $R_2$ is $(CH_2)_m(OCH_2CH_2)_p$, where m is an integer between 1-8 and p is an integer between 0-1000.

In another aspect, the invention features a method for preparing protein dimmers having a structure according to formula (XXI), (XXI)

P-S-CH₂-[triazole]-N-(R₂)-N-[triazole]-CH₂-S-P

XXI by contacting two compounds according to formula (X), (X)

P-S-CH₂-C≡CH, with a compound according to formula (XX), (XX)

⁻N=N⁺=N—(R₂)—N=N⁺=N⁻, where $R_2$ is $(CH_2)_m(OCH_2CH_2)_p$, where m is an integer between 1-8 and p is an integer between 0-1000; under conditions that will result in a cycloaddition reaction between the alkyne and azide moieties.

In another aspect, the invention features a method for delivering drugs to cancer cells expressing both phosphatidylserine and an RGD peptide or folate receptor.

In another aspect, the invention features a method for site-specifically pegylating annexin ketoamides of formula (II) by contacting the compound according to formula (II) with polyethylene glycol carbazides (XXII) in the presence or absence of sodium cyanoborohydride.

(XXII)

PEG-C(=O)-NNH₂.

In still another aspect, the invention features a method of site-specifically modifying annexin proteins containing solvent accessible cysteines such as, by first contacting the protein with propargyl substrates IX as in claim 14, and then condensing X with pegylated azides to give XXIV.

PEG—N₃ + P—S—CH₂—C≡CH →

XXIII        (X)

P—S—CH₂—[triazole]—N—PEG

XXIV

PEG=polyethylene glycol polymer; P=protein, annexin V-128

In some embodiments, the protein is annexin V-128.

In still another aspect, the invention features a compound of formula (XXV).

(XXV)

$X_3$—(R₂)—$X_1$—NH₂, where $X_1$ is O, NH, or CONH;

$R_2$ is $(CH_2)_m(OCH_2CH_2)_p$, where m is an integer between 1-8 and p is an integer between 0-1000; and $X_3$ is $N_3$, SH, or propargyl.

In another aspect, the invention features a method of pegylating annexin proteins including treating a compound according to formula (XXVIII), (XXVIII)

Y-CH₂-C(=O)-[phenyl]-C(=O)-NH-PEG where Y is a halogen, with annexin proteins containing a free cysteine to afford (XXX)

AN-S-CH₂-C(=O)-[phenyl]-C(=O)-NH-PEG, wherein AN-S represents an annexin protein.

In another aspect, the invention features a method of pegylating annexin proteins including treating a compound according to formula (XXIX), (XXIX)

Y-CH₂-C(=O)-[phenyl]-S(=O)₂-NH-PEG, where Y is a halogen, with annexin proteins containing a free cysteine to afford

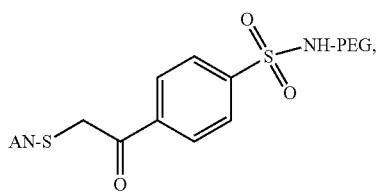
(XXXI)

wherein AN-S represents an annexin protein.

In another aspect, the invention features a method of forming dimers of annexin V-128 by treating the protein with bis-maleimides according to formula (XXXII),

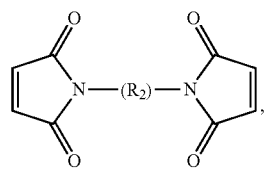
(XXXII)

where $R_2$ is $(CH_2)_m(OCH_2CH_2)_p$, where m is an integer between 1-8 and p is an integer between 0-1000, to give compounds according to formula (XXXIII),

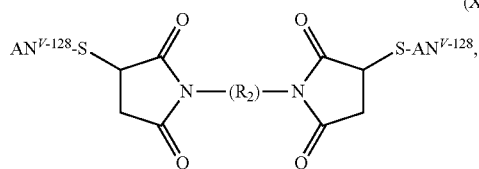
(XXXIII)

where $AN^{V-128}$ represents annexin V-128.

In still another aspect, the invention features a molecule of formula (XXXIII).

In another aspect, the invention features a method of forming dimers of annexin V or annexin V-128 by combining a compound according to the following formula,

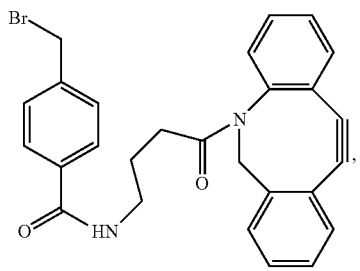 [SMILES: O=C(NCCCC(=O)N1Cc2ccccc2C#Cc2ccccc21)c1ccc(CBr)cc1]

with a compound having the formula P—SH, where P is an annexin V protein or an annexin V-128 protein, to provide an intermediate compound (XXXIV),

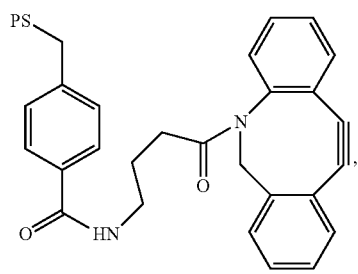
(XXXIV)

which can then be treated with a

P-L-$N_3$ (XXXV), where P is an annexin V protein or an annexin V-128 protein, L is compound represented by the formula (XXXV) a linker that covalently attaches the azido moiety to the protein, to provide a compound according to formula (XXXVI),

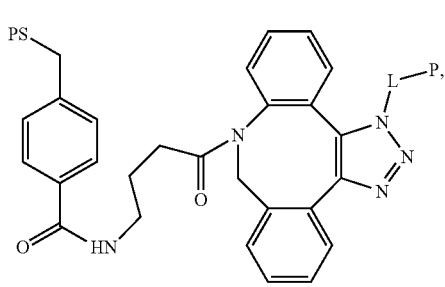
(XXXVI)

or the regioisomer thereof.

In another aspect, the invention features a method of forming dimers of annexin V or annexin V-128 by combining a compound according to the following formula,

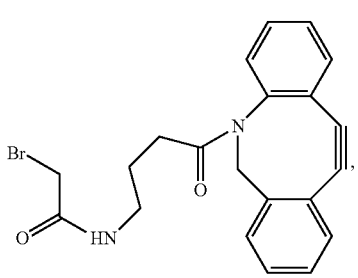
(XXXVII)

with a compound having the formula P—SH, where P is an annexin V protein or an annexin V-128 protein, to provide an intermediate compound (XXXVIII),

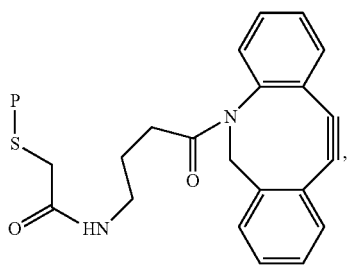
(XXXVIII)

which can then be treated with a

P-L-N$_3$ (XXXV), where P is an annexin V protein or an annexin V-128 protein, L is compound represented by the formula (XXXV) a linker that covalently attaches the azido moiety to the protein, to provide a compound according to formula (XXXIX),

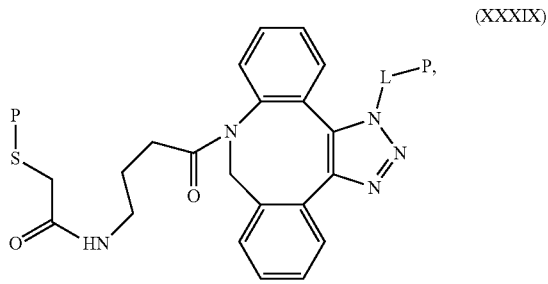

(XXXIX)

or the regioisomer thereof.

The therapeutic peptides, and pharmaceutical compostions thereof, of the present invention may be administered to a subject by any methods known in the art, including but not limited to, oral, topical, transdermal, parenteral, subcutaneous, intranasal, intramuscular and intravenous routes, including both local and systemic applications. In addition, the therapeutic peptides, and pharmaceutical compostions thereof, of the present invention may be designed to provide delayed or controlled release using formulation techniques which are well known in the art.

The present invention also includes a pharmaceutical composition comprising a therapeutically effective amount of the conjugate described herein above in combination with a pharmaceutically acceptable carrier. As used herein, a "pharmaceutically acceptable carrier" is a pharmaceutically acceptable solvent, suspending agent or vehicle for delivering the therapeutic peptides of the present invention to the human or animal. The carrier may be liquid or solid and is selected with the planned manner of administration in mind. Examples of pharmaceutically acceptable carriers that may be utilized in accordance with the present invention include, but are not limited to, PEG, liposomes, ethanol, DMSO, aqueous buffers, oils, and combinations thereof.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "CX—CY-alkyl", wherein x is 1-5 and y is 2-10 indicates a particular alkyl group (straight- or branched-chain) of a particular range of carbons. For example, the expression C1-C6-alkyl includes, but is not limited to, methyl, ethyl, propyl, butyl, isopropyl, tert-butyl, isobutyl, n-pentyl, and n-hexyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

As used herein, the term "anticancer agent" refers to a molecule capable of inhibiting cancer cell function. The agent may inhibit proliferation or may be cytotoxic to cells. A variety of anticancer agents can be used, and include those that inhibit protein synthesis and those that inhibit expression of certain genes essential for cellular growth or survival. Anticancer agents include those that result in cell death and those that inhibit cell growth, proliferation and/or differentiation. Preferably, the anticancer agent is selectively toxic against certain types of cancer cells but does not affect or is less effective against other normal cells.

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems can be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

A "bifunctional polymer" or "bifunctional linker" refers to a molecule comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein. A "multi-functional polymer" or "multi-functional linker" refers to a molecule comprising two or more discrete functional groups that are capable of reacting specifically with other moieties (including but not limited to, amino acid side groups) to form covalent or non-covalent linkages.

As used herein, a "conjugate" refers to a molecule that contains at least one receptor-binding ligand and at least one anticancer agent that are coupled directly or via a linker and that are produced by chemical coupling methods or by recombinant expression of chimeric DNA molecules to produce fusion proteins. Included in this definition are multimers of annexin proteins in which monomer can be thought of as a receptor or phosphatidylserine-binding ligand. Such dimers or multimers may contain as well anticancer agents or ligands to biomarkers.

The term "biologically compatible" refers to compounds that do not have biological activity and are non-toxic and non-inflammatory to, e.g., humans.

The term "cycloaddition" refers to a pericyclic chemical reaction, in which two or more unsaturated molecules (or parts of the same molecule) combine with the formation of a cyclic adduct in which there is a net reduction of the bond multiplicity.

As used herein, the term "covalently coupled", "linked", "bonded", "joined", and the like, with reference to the ligand and anticancer agent components of the therapeutic peptides, and pharmaceutical compostions thereof, of the present invention, mean that the specified components are either directly covalently bonded to one another or indirectly covalently bonded to one another through an intervening moiety or components, such as a bridge, spacer, linker or the like. For example but not by way of limitation, the ligand and the anticancer agent may be chemically coupled together via a thioether linkage as described in Mickisch et al. (1993).

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the invention. Therapeutic effect may include, for example, but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "fusion protein" includes a single molecular entity having at least two polypeptide domains that are not normally present in a single, natural polypeptide, and where the polypeptide domains are linked by a polypeptide chain. Thus, naturally occurring proteins are not "fusion proteins", as used herein.

The term "heteroaryl," as used herein, represents an aromatic (i.e., containing 4n+2 pi electrons within the ring system) mono-, bi-, or tricyclic-membered ring having between 5-14 ring members and containing one, two, three, or four heteroatoms independently selected from the group consisting of nitrogen, oxygen, and sulfur. Exemplary heteroaryls include, but are not limited to pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl (e.g., 1,3,4-thiadiazole), isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like.

The term "homogeneous" as used herein is defined in the context of the term "substantially pure", vide infra.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

A "liposome" is a small vesicle composed of various types of lipids, phospholipids and/or surfactant. The components of the liposome are commonly arranged in a bilayer formation, similar to the lipid arrangement of biological membranes.

As used herein, the term "multimer" is defined as a protein molecule composed of two or more monomeric proteins or modified proteins.

The term "peptide" includes chains of amino acids linked by peptide bonds. The term "peptide" can also refer to a "protein" or "polypeptide", which are compounds made of amino acids arranged in a linear chain and folded into a globular form. A variety of polypeptides or proteins may be used within the scope of the methods and compositions provided herein. In certain embodiments, the proteins may comprise antibodies or fragments of antibodies containing an antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the common amino acids found in naturally occurring proteins, or at least one modified or unusual amino acid. Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. Polypeptides made synthetically may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Protein, polypeptide and peptide sequences can be found at computerized databases known to those of ordinary skill in the art. One such database is the National Center for Biotechnology Information's GenBank and GenPept databases. Alternatively, various commercial preparations of proteins, polypeptides, and peptides are known to those of skill in the art.

The term "peptoid" refers to poly-N-substituted glycines, where the N-substituent can be, for example, the side chains of natural or unnatural amino acids. Exemplary peptoids can have e.g., 2-25 residues.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers to any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

By "polyethylene glycol" or "PEG" is also meant any other polyalkylene glycol compound or a derivative thereof, with or without coupling agents or derivatization with coupling or activating moeities (e.g., with thiol, triflate, tresylate, azirdine, oxirane, or preferably with a maleimide moiety). Compounds, such as maleimido monomethoxy PEG, are exemplary or activated PEG compounds of the invention. Other polyalkylene glycol compounds, such as polypropylene glycol, may be used in the present invention.

Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides. The PEG can be linked to any N-terminal amino acid of the conjugate, and/or can be linked to an amino acid residue downstream of the N-terminal amino acid, such as lysine, histidine, tryptophan, aspartic acid, glutamic acid, and cysteine, for example, or other such linkable amino acids known to those of skill in the art. Cysteine-pegylated conjugates, for example, are created by attaching polyethylene glycol to a thio group on a cysteine residue of the conjugate. The PEG moiety attached to the conjugate may range in molecular weight, for example, from about 200 to 40,000 MW.

The term "prevent," as used herein, refers to prophylactic treatment or treatment that prevents one or more symptoms or conditions of a disease, disorder, or conditions described herein. Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein, or a pharmaceutically acceptable salt or solvate thereof, or a pharmaceutical composition thereof, can be acute, short-term, or chronic. The doses administered may be varied during the course of preventative treatment.

The term "receptor," as used herein, will be understood to include any peptide, protein, glycoprotein, polycarbohydrate, or lipid that is uniquely expressed or overexpressed on the surface of cancer cells or cells in the tumor vasculature and is exposed on the surface of cancer cells or cells in the tumor vasculature in a manner that will allow interaction with a circulating targeting agent, such as the conjugate.

The terms "treat," "treating," and "treatment," as used herein, will be understood to include both inhibition of tumor growth, as well as induction of tumor cell death.

The term "subject" is intended to include organisms, e.g., prokaryotes and eukaryotes, which are capable of suffering from or afflicted with a disease, disorder or condition. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, arthritis, atherothrombosis, plaque rupture, or Crohn's disease. In another embodiment, the subject is a cell.

As used herein, "substantially pure" means an object species is the predominant species present (i.e., on a molar basis, it is more abundant than any other individual species in the composition), and preferably, a substantially purified fraction is a composition wherein the object species comprises at least about 50% (on a molar basis) of all macromolecular species present. Generally, a substantially pure composition will comprise more than about 80% of all macromolecular species present in the composition, more preferably, more than about 85%, 90%, 95%, and 99%. Most preferably, the object species is purified to essential homogeneity (contaminant species cannot be detected in the composition by conventional detection methods), wherein the composition consists essentially of a single macromolecular species.

As used herein the term "therapeutic protein" may either be a protein conjugate, a fusion protein prepared recombinantly with or without additional linkages to organic chemical entities with potential biological activities, or chemically generated multimers (e.g., crosslinked proteins) with or without additional linkages to organic chemical entities with potential biological activities.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Where a group is substituted, the group may be substituted with e.g., 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, halogen (—F, —Cl, —Br, or —I), azido (—$N_3$), nitro (—$NO_2$), cyano (—CN), acyloxy (—OC(=O)R'), acyl (—C(=O)R'), alkoxy (—OR'), amido (—NR'C(=O)R" or —C(=O) NRR'), amino (—NRR'), carboxylic acid (—$CO_2H$), carboxylic ester (—$CO_2R'$), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, aryl, or heteroaryl. In some embodiments, the substituent groups themselves may be further substituted with, for example, 1, 2, 3, 4, 5, or 6 substituents as defined herein. For example, a $C_{1-6}$ alkyl, phenyl, or heteroaryl group may be further substituted with 1, 2, 3, 4, 5, or 6 substituents as described herein.

The present invention includes all isomeric (e.g., enantiomeric, diastereomeric, and geometric (or conformational)) forms of the compounds; for example, syn and anti isomers, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The present invention includes all pharmaceutically acceptable isotopically-labeled compounds of the invention, wherein one or more atoms are replaced by atoms having the same atomic number, but an atomic mass or mass number different from the atomic mass or mass number usually found in nature. Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Salts derived from appropriate bases include alkali metal, alkaline earth metal, and ammonium salts. Representative alkali or alkaline earth metal salts include sodium, lithium, potassium, calcium, magnesium, and the like. One class of salts includes the pharmaceutically acceptable salts. The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. *Pharmaceutical Sciences* 66:1-19, 1977 and in *Pharmaceutical Salts: Properties, Selection, and Use,* (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

DETAILED DESCRIPTION OF THE INVENTION

This invention is concerned with the design and preparation of therapeutic peptides, and pharmaceutical compositions thereof, which include protein conjugates and fusion proteins, including homogeneous fusion protein conjugates bearing multiple entities, that can be targeted to specific cancer cell types. This objective of targeted therapy using therapeutic peptides, and pharmaceutical compostions thereof, can be met using (1) a targeted component with high affinity for cancer cell surface biomarkers, (2) site-specific methods for the attachment of each entity to a specific site on the fusion protein, and (3) cleavage sites for the release of therapeutic entities.

The methods and therapeutic proteins described herein employ site-specific crosslinking reactions in order to link biologically active agents (e.g., cancer therapeutics) to the protein that can be used for targeted drug delivery (e.g., targeted delivery to cancer cells). Accordingly, one set of therapeutic proteins described herein are crosslinked compounds that can consist of various proteins (e.g., annexin proteins or analogues thereof) in monomeric or multimeric form, crosslinked to compounds such as ligands of cell surface biomarkers, small molecule drug entities, and imaging or optical agents. In some embodiments, therapeutic proteins may be designed simply to overcome the renal threshold for glomerular filtration of 68,000 Da, or targeted to cell surface biomarkers in addition to phosphatidylserine, or carry agents for the destruction of cancer cells.

The present invention further relates to methods of making and using the crosslinked products, themselves or as components, in microarrays, the production of fine chemicals and kits, radio-labeling, molecular and optical imaging applications, and the diagnosis and treatment of cancer. Although the focus of this disclosure centers on cancer cells, the invention and its methods can be used in other therapeutic methods, including disease states in which phosphatidylserine appears on the external surface of cells, such as in certain viral diseases.

As described herein, members of the annexin family of proteins are of particular interest. Annexin V, for example, has been the subject of diagnostic studies and has been employed in clinical use without any significant toxicities. Its high affinity for phosphatidylserine (PS), a cell surface biomarker of apoptotic cells, is well established. The protein can be used in the development of therapeutic proteins, e.g., imaging agents. In addition to its high affinity for PS, it has compelling properties that impact the immune system and clearance of cells. Indeed, studies over the last decade have indicated that the exposure of phosphatidylserine on the surface of cells can inhibit immune responses. A recent study by X. Yan et al. shows that blocking PS results in enhanced T cell mediated tumor immunity and inhibited tumor growth (Cancer Immunol Immunother. 2012, 61, 1917-27). Indeed, we describe new compositions herein that make practical the use of annexin-based therapeutics as immunotherapeutics.

Another clinically relevant feature of annexin V is its ability to recruit phagocytes and engage in efferocytosis upon mutation of an RGT triad to RGD triad in its N-terminus (K. Schutters et al., Cell Death Differ. 2013 20, 49-56). Recently, the mononuclear phagocyte lineage has been found to have biologically and clinically significant tumor enhancing effects that could be exploited in novel treatments for cancer patients (D. S. Dickens et al., J Pediatr Hematol Oncol. 2009, 31, 14-7). Consequently, annexin's ability to unlock T-cell antitumor immunity and its efferocytotic potential provide additional dimensions to its role as a homing agent and delivery system of multiple therapeutic cargo.

In therapeutic proteins described herein, the annexin protein (and additional ligands to biomarkers) serve as targeting components, and the drugs serve as warheads. As indicated above The annexin protein also has the potential to promote antitumor immunity which gives the agent an additional dimension.

The modular synthetic approaches described herein offer numerous advantages in assembling the elements of this multi-therapeutic agent. It provides a basis for molecular diversity which includes spacer amino acids, polyethylene glycol and alkyl chains that can be systematically varied in the template to optimize bioavailability parameters and the interactions of the biological elements with the target cell. The ability to modify the composition of the amino acids, for example, as well as their positions, is a variable that is likely to have therapeutic significance.

Therapeutic proteins described herein therefore can provide a triumvirate of properties embracing immunotherapeutic, efferocytotic, and affinities for cancer cell surface biomarkers, which make annexin proteins extraordinarily attractive delivery vehicles for additional targeted therapies. In particular, these proteins can serve as scaffolds for the attachment of entities with various biological activities and meet the requirements of site-specifically (1) attaching combinations of cytotoxic drugs, anti-angiogenics, and other anticancer agents in prodrug formats (2) attaching additional entities that have high affinity to the target cancer cell to augment the homing abilities of annexin and achieve high precision targeting.

Therapy (Including Cancer Therapy)

In particular, therapeutic peptides can be useful for the treatment or prevention of diseases characterized by increased necrotic or apoptotic activity in cells. For example, the therapeutic peptides, and pharmaceutical compostions thereof, can be used for the treatment or prevention of cancer and other proliferative diseases, inflammation and inflammatory diseases (e.g., inflammatory bowel disease and rheumatoid arthritis) Crohn's disease, and diabetes.

Cancers that may be treated according to the methods described herein include, but are not limited to, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

Proliferative diseases that may be treated according to the methods described herein include dyslasia, benign dysproliferative disorders, leukoplakia, Bowen's disease, keratoses, Farmer's Skin, solar cheilitis, solar keratosis, obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Still other proliferative diseases are described in U.S. Pat. Nos. 5,639,600 and 7,087,648, hereby incorporated by reference.

Biologically Active Agents

Exemplary classes of therapeutic agents include, but are not limited to carbohydrates, anti-microbials, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogel and ramatroban, antibodies, neurotransmitters, psychoactive drugs, oligonucleotides, proteins, lipids, and combinations thereof.

Additional therapeutic agents that can be used in the methods described herein include, without limitation, growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutyric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothenic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active or biologically compatible agent can be an anti-inflammatory agent, such as an NSAID, corticosteriod, or COX-2 inhibitor, e.g., rofecoxib, celecoxib, valdecoxib, or lumiracoxib. Therapeutic agent may also include antibiotics.

Diagnostic Agents

Exemplary diagnostic agents which can be used in the methods described herein include, without limitation, imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials. Other diagnostic agents that can be used in the methods described herein include those described in U.S. Patent Publication No. 20100099649, which is herein incorporated by reference in its entirety.

Therapeutic Agents Used in Cancer Therapy

Exemplary therapeutic peptides, and pharmaceutical compostions thereof, for use in the treatment for cancer are provided disclosed. The present invention provides conjugates that include a ligand having the ability to specifically bind to an external receptor or binding site on an outer surface of a tumor vasculature endothelial cell or cancer cell, wherein the external receptor or binding site is specific for tumor vasculature endothelial cells or cancer cells (i.e., is uniquely expressed or overexpressed on a luminal surface of the tumor vasculature endothelial cell or cancer cell).

Many cancer therapeutics provide only marginal benefits to the majority of patients to whom they are administered. Two of the most formidable therapeutic challenges involve the need for selective toxicity versus cancer cells to avoid harming healthy tissues, and the selection and delivery of combination therapies to deal with the heterogeneity and progression of tumors. One strategy to reduce exposure of healthy cells to cytotoxic agents would be the use of targeted therapies to exploit biomarkers on the surface of cancer cells and deliver such agents to tumor cells preferentially. One such agent is the antibody-drug conjugate (ADC) which exploits the antibody's affinity for a target biomarker and delivers anticancer agents to the associated cell.

A problem in the development of current protein conjugates is the difficulty of producing homogeneous agents that meet the demands of product uniformity. For example, the above-mentioned ADC strategy commonly consists of a mixture of species, each with a distinct structural identity. The formation of an ADC involves conjugation of the drug to the antibody, a process that requires controlled chemical reactions involving specific amino acids on the antibody. Cysteine and lysine residues are often targeted for conjugation due to their reactivity and the possibility of their being preferentially modified. Nonetheless, even with the narrow focus on these two amino acids, the difficulty of restricting conjugation to only specific loci on the protein is confounded by the presence of multiple lysine and, to a lesser extent, cysteine amino acid residues of similar reactivity all along the protein surface. Consequently, conjugation results in a mixture of ADC species differing not only in the number of drugs attached to the antibody but also in the sites of drug linkage. Thus the amount of drug attached to the antibody is generally reported as an average drug to antibody ratio (DAR), which describes a heterogeneous population of ADCs with different numbers and locations of cytotoxic drugs. ADCs conjugated to cysteines are mixtures having DAR ratios ranging from 0-8, and ADCs conjugated to the more numerous lysines have the potential for even greater variability.

The net results of creating a heterogeneous mixture containing a array of components that are structurally uncharacterized are that (1) there is little practical potential for systematically developing an optimal drug on the basis of structural considerations according to classical lead development, (2) losses of activity by attachment to sites that compromise activity are difficult to uncover, (3) unraveling toxicities or other limiting properties of such a complex formulation become immensely difficult tasks and potential high order liabilities, and (4) there is a greater opportunity for immune reactions and resistance.

For protein conjugation, product homogeneity requires that the same entity be made to the same protein site, a formidable challenge in light of the dearth of site-specific methods. An attractive agent for cancer therapy would be a single agent that not only selectively delivers cytotoxic agents to cancer cells but can also stimulate antitumor immunity, thereby allowing for effective combination therapy. This type of agent embraces the two attributes of targeted and combination therapy that have become the mantra of cancer therapy. Although such multi-therapeutic agents combine compelling features of cancer therapy, methods for the development of homogeneous preparations, consisting of conjugates of a single chemical composition that can be manufactured with guaranteed product uniformity, are lacking. The latter would be a useful addition to the armamentarium of cancer therapeutics.

To achieve practical, well-characterized therapeutic agents and to avoid intractable mixtures, there is clearly a need for the construction of homogeneous protein conjugates that bear multiple entities and have extended circulation times in vivo. Consequently, key aspects of this invention, which constitute the enabling technology, involve site-specifically grafting several therapeutically relevant entities onto a fusion protein carrier that exceeds the glomerular filtration threshold for excretion. Although each of the entities represents a distinct therapeutic modality or ligand to a biomarker, the assembly of protein conjugates represents a homogeneous preparation, e.g., a single species with a distinct structural identity. Another aspect of this invention deals with the choice of fusion protein as a delivery system which is selected for its high affinity to the target cancer cells, its ability to promote antitumor immunity, and its duration of action.

In some embodiments, the anticancer agent may be selected from the group consisting of the following therapeutic agents and where therapeutic agent has the requisite functionality to be covalently attached to the protein.

13-cis-Retinoic Acid;

2-CdA2-Chlorodeoxyadenosine;

5-Azacitidine5-Fluorouracil5-FU;

6-Mercaptopurine 6-MP6-TG6-Thioguanine;

Abraxane; Accutane®; Actinomycin-Adriamycin®; Adrucil®; Afinitor®; Agrylin®; Ala-Cort®; Aldesleukin; Alemtuzumab; ALIMTA; Alitretinoin; Alkaban-AQ®; Alkeran®; All-transretinoic Acid; Alphalnterferon; Altretamine; Amethopterin; Amifostine; Aminoglutethimide; Anagrelide; Anandron®; Anastrozole; Arabinosylcytosine; Aranesp®; Aredia®; Arimidex®; Aromasin®; Arranon®; Arsenic Trioxide; Arzerra™; Asparaginase; Atra; Avastin®; Azacitidine;

BCG; BCNU; Bendamustine; Bevacizumab; Bexarotene; BEXXAR®; Bicalutamide; BiCNU; Blenoxane®; Bleomycin; Bortezomib; Busulfan; Busulfex®;

C225; Calcium Leucovorin; Campath®; Camptosar®; Camptothecin-11; Capecitabine; Carac™; Carboplatin; Carmustine; Carmustine; WaferCasodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®;

Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate Dexasone; Dexrazoxane; DHAD; DIC; Diodex; Docetaxel; Doxil®; Doxorubicin; Doxorubicin Liposomal; Droxia™; DTIC; DTIC-Dome®; Duralone®;

Efudex®; Eligard™; Ellence™; Eloxatin™; Elspar®; Emcyt®; Epirubicin; Epoetin Alfa; Erbitux; Erlotinib; Erwinia L-asparaginase; Estramustine; Ethyol; Etopophos®; Etoposide; Etoposide Phosphate; Eulexin®; EverolimusEvista®; Exemestane;

Fareston®; Faslodex®; Femara®; FilgrastimFloxuridineFludara®; FludarabineFluoroplex®; FluorouracilFluorouracil (cream) FluoxymesteroneFlutamideFolinic Acid-FUDR®; Fulvestrant G-CSF; Gefitinib; Gemcitabine; Gemtuzumab ozogamicin; Gemzar; Gleevec™; Gliadel®; WaferGM-CSF; Goserelin; Granulocyte-Colony Stimulating FactorGranulocyte Macrophage Colony Stimulating Factor;

Halotestin®; Herceptin®; HexadrolHexalen®; HexamethylmelamineHMMHycamtin®; Hydrea®; Hydrocort Acetate®; Hydrocortisone; Hydrocortisone Sodium Phosphate; Hydrocortisone Sodium Succinate; Hydrocortone Phosphate Hydroxyurea;

Ibritumomab; Ibritumomab Tiuxetan; Idamycin®; Idarubicinlfex®; IFN-alpha; Ifosfamide; IL-11; IL-2 Imatinib mesylate; Imidazole Carboxamide; Interferon alfa; Interferon Alfa-2b (PEG Conjugate); Interleukin-2; Interleukin-11; Intron A®; (interferon alfa-2b); Iressa®; Irinotecan; Isotretinoin; Ixabepilone; Ixempra™;

Kidrolase (t);

Lanacort®; Lapatinib; L-asparaginase; LCR; Lenalidomide; Letrozole; Leucovorin; Leukeran; Leukine™; Leuprolide; Leurocristine; Leustatin™; Liposomal Ara-C; Liquid Pred®; Lomustine; L-PAML-Sarcolysin; Lupron®; Lupron Depot®;

Matulane®; Maxidex; Mechlorethamine; Mechlorethamine Hydrochloride; Medralone®; Medrol®; Megace®; Megestrol; Megestrol Acetate; Melphalan; Mercaptopurine; Mesna; Mesnex™; Methotrexate; Methotrexate Sodium; Methylprednisolone; Meticorten®; Mitomycin; Mitomycin-C; Mitoxantrone; M-Prednisol®; MTC; MTX; Mustargen®; Mustine; Mutamycin®; Myleran®; Mylocel™ Mylotarg®;

Navelbine®; NelarabineNeosar®; Neulasta™ Neumega®; Neupogen®; Nexavar®; Nilandron®; NilotinibNilutamideNipent®; Nitrogen Mustard; Novaldex®; Novantrone®; Nplate Octreotide; Octreotide acetate; Ofatumumab; Oncospar®; Oncovin®; Ontak®; Onxal™ OprelvekinOrapred®; Orasone®; Oxaliplatin Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pentostatin; Phenylalanine Mustard; Platinol®; Platinol-AQ®; Prednisolone; Prednisone; Prelone®; Procarbazine; PROCRIT®; Proleukin®; Prolifeprospan 20 with Carmustine Implant; Purinethol®;

Raloxifene; Revlimid®; Rheumatrex®; Rituxan®; RituximabRoferon-A®; (Interferon Alfa-2a); Romiplostim-Rubex®; Rubidomycin hydrochloride;

Sandostatin®; Sandostatin LAR®; SargramostimSolu-Cortef®; Solu-Medrol®; SorafenibSPRYCEL™ STI-571StreptozocinSU11248SunitinibSutent®;

Tamoxifen; Tarceva®; Targretin®; Tasigna®; Taxol®; Taxotere®; Temodar®; Temozolomide; Temsirolimus; Teniposide; TESPA; Thalidomide; Thalomid®; TheraCys®; Thioguanine; Thioguanine Tabloid®; Thiophosphoamide-Thioplex®; ThiotepaTICE®; Toposar®; Topotecan; Toremifene; Torisel®; Tositumomab; Trastuzumab; Treanda®; Tretinoin; Trexall™ Trisenox®; TSPATYKERB®;

VCRVectibix™ Velban®; Velcade®; VePesid®; Vesanoid®; Viadur™ Vidaza®; Vinblastine; Vinblastine Sulfate; Vincasar Pfs®; Vincristine; Vinorelbine; Vinorelbine tartrate; VLBVM-26; Vorinostat; VotrientVP-16; Vumon®;

Xeloda®;

Zanosar®; ; Zevalin™ Zinecard®; Zoladex®; Zoledronic acid; Zolinza; and Zometa®.

In other embodiments, therapeutic agent is any of therapeutic agents described in Table A, which can be used in chemotherapy regimens and which can have a suitable functional group for conjugation to any of the moieties described herein, or any combination thereof.

TABLE A

| Therapeutic Class | Exemplary, Non-Limiting Agents |
|---|---|
| Alkylating Agents | Nitrogen mustards: such as mechlorethamine (nitrogen mustard), chlorambucil, cyclophosphamide (Cytoxan ®), ifosfamide, and melphalan<br>Nitrosoureas: which include streptozocin, carmustine (BCNU), and lomustine<br>Alkyl sulfonates: busulfan<br>Triazines: dacarbazine (DTIC) and temozolomide (Temodar ®)<br>Ethylenimines: thiotepa and altretamine (hexamethylmelamine) |
| Antimetabolites | 5-fluorouracil (5-FU)<br>6-mercaptopurine (6-MP)<br>Capecitabine (Xeloda ®)<br>Cladribine<br>Clofarabine<br>Cytarabine (Ara-C ®)<br>Floxuridine<br>Fludarabine<br>Gemcitabine (Gemzar ®)<br>Hydroxyurea<br>Methotrexate<br>Pemetrexed (Alimta ®)<br>Pentostatin<br>Thioguanine |
| Anti-tumor antibiotics (e.g., anthracyclines) | Daunorubicin<br>Doxorubicin (Adriamycin ®)<br>Epirubicin<br>Idarubicin<br>Actinomycin-D<br>Bleomycin<br>Mitomycin-C |
| Topoisomerase inhibitors | topoisomerase I inhibitors<br>topotecan<br>irinotecan (CPT-11).<br>topoisomerase II inhibitors<br>etoposide (VP-16)<br>teniposide<br>Mitoxantrone |
| Mitotic inhibitors | Taxanes such as paclitaxel (Taxol ®) and docetaxel (Taxotere ®)<br>Epothilones: ixabepilone (Ixempra ®)<br>Vinca alkaloids such as vinblastine (Velban ®), vincristine (Oncovin ®), and vinorelbine (Navelbine ®)<br>Estramustine (Emcyt ®) |
| Corticosteroids | Examples include prednisone, methylprednisolone (Solumedrol ®), and dexamethasone (Decadron ®). |
| Miscellaneous Chemotherapeutics | L-asparaginase<br>bortezomib (Velcade ®)<br>imatinib (Gleevec ®)<br>gefitinib (Iressa ®)<br>sunitinib (Sutent ®) |
| Differentiating agents | retinoids<br>tretinoin (ATRA or Atralin ®)<br>bexarotene (Targretin ®)<br>arsenic trioxide (Arsenox ®). |
| Hormone therapy | The anti-estrogens: fulvestrant (Faslodex ®), tamoxifen, and toremifene (Fareston ®)<br>Aromatase inhibitors: anastrozole (Arimidex ®), exemestane (Aromasin ®), and letrozole (Femara ®) |

TABLE A-continued

| Therapeutic Class | Exemplary, Non-Limiting Agents |
|---|---|
| | Progestins: megestrol acetate (Megace ®)<br>Estrogens<br>Anti-androgens: bicalutamide (Casodex ®), flutamide (Eulexin ®), and nilutamde (Nilandron ®)<br>Gonadotropin-releasing hormone (GnRH), also known as luteinizing hormone-releasing hormone (LHRH) agonists or analogs: leuprolide (Lupron ®) and goserelin (Zoladex ®) |
| Immunotherapy | Monoclonal antibody therapy (passive immunotherapies), such as rituximab (Rituxan ®) and alemtuzumab (Campath ®)<br>Non-specific immunotherapies and adjuvants (other substances or cells that boost the immune response), such as BCG, interleukin-2 (IL-2), and interferon-alfa<br>Immunomodulating drugs, for instance, thalidomide and lenalidomide (Revlimid ®)<br>Cancer vaccines (active specific immunotherapies) |

In other embodiments, therapeutic proteins can include one or more of the drugs used in any of the chemotherapy regiments described in Table B.

TABLE B

| Combination Regiment | Constituent Drugs |
|---|---|
| ABVD regimen | Adriamycin (doxorubicin)<br>Bleomycin<br>Vinblastine<br>Dacarbazine |
| BEACOPP regimen | Bleomycin<br>Etoposide<br>Adriamycin (doxorubicin)<br>Cyclophosphamide<br>Oncovin (vincristine)<br>Procarbazine<br>Prednisone |
| CAV regimen | Cyclophosphamide<br>Adriamycin (doxorubicin)<br>Vincristine |
| CHOP regimen | Cyclophosphamide<br>Hydroxyldaunorubicin (doxorubicin)<br>Oncovin (vincristine)<br>Prednisone |
| COPP regimen | Cyclophosphamide<br>Oncovin (vincristine)<br>Procarbazine<br>Prednisone |
| EPOCH regimen | Etoposide<br>Prednisone<br>Oncovin (vincristine)<br>Cyclophosphamide<br>Hydroxyldaunorubicin (doxorubicin) |
| MACOP-B regimen | Methotrexate<br>ARA-C (Cytarabine)<br>Cyclophosphamide<br>Oncovin (vincristine)<br>Prednisone<br>Bleomycin |
| MOPP regimen | Mechlorethamine (aka HN2 or Mustargen)<br>Oncovin (vincristine)<br>Procarbazine<br>Prednisone |
| R-CHOP regimen | Rituximab (Rituxan)<br>Cyclophosphamide<br>Hydroxyldaunorubicin (doxorubicin)<br>Oncovin (vincristine)<br>Prednisone |
| Stanford V regimen | Doxorubicin<br>Vinblastine<br>Mechlorethamine<br>Vincristine |

TABLE B-continued

| Combination Regiment | Constituent Drugs |
|---|---|
| | Bleomycin |
| | Etoposide |
| | Prednisone |

Still other combinations of combination chemotherapy regimens are known in the art (see, e.g., http://www.hci.utah.edu/patientdocs/hci/drugs/Chemoregimen/combocancer.html), and an exemplary summary is provided in Table C.

TABLE C

| Type of Cancer | Name of Combination Chemotherapy Regimen |
|---|---|
| Adenocarcinoma | CaT |
| | Carbo-Tax |
| | CF |
| | EP |
| | FAM |
| | Paclitaxel-Carboplatin-Etoposide |
| | PVB |
| Brain | CDDP/VP-16 |
| | COPE |
| | MOP |
| | PCV |
| | POC |
| | "8 in 1" |
| Breast | AC |
| | ACE (CAE) |
| | AC(e) |
| | AC/Paclitaxel, Dose Dense |
| | AC/Pacilitaxel, Sequential |
| | AT |
| | CAF |
| | Capecitabine-Docetaxel |
| | CEF |
| | CFM see CNF |
| | CMF |
| | CMF-IV |
| | CMFP |
| | CMFVP |
| | CNF |
| | Cooper Regimen |
| | CY/A see AC |
| | Dox >> CMF, Sequential |
| | FAC |
| | FEC |
| | FNC |
| | HEC |
| | ICE-T |
| | MF |
| | MV |
| | NA see Vinorelbine-Doxorubicin |
| | Paclitaxel-Herceptin |
| | Paclitaxel-Vinorelbine |
| | TAC |
| | Tamoxifen-Epirubicin |
| | Trastuzumab-Paclitaxel |
| | VATH |
| | VD |
| | Vinorelbine-Doxorubicin |
| | VM |
| | X + T see Capecitabine-Docetaxel |
| Colorectal | CAPIRI |
| | F-CL |
| | Fle |
| | FOLFIRI |
| | FOLFOX-2 |
| | FOLFOX-3 |
| | FOLFOX-4 |
| | FOLFOX-6 |
| | FOLFOX-7 |
| | FU-LV see F-CL |
| | FU/LV/CPT-11 |
| | IFL + Bevacizumab |
| | XELOX |
| Esophageal | TCF |
| | TIP |
| Gastric | EAP |
| | ECF |
| | EFP |
| | ELF |
| | FAM |
| | FAMTX |
| | FAP |
| | FUP |
| | MCF |
| | PFL |
| | TC |
| Genitourinary—Bladder | CISCA |
| | Cisplatin-Docetaxel |
| | CMV |
| | Gemcitabine-Cisplatin |
| | M-VAC |
| | PC |
| Genitourinary—Cervical | BIP |
| | BOMP |
| | Cisplatin-Fluorouracil |
| | Cisplatin-Vinorelbine |
| | CLD-BOMP |
| | MOBP |
| Genitourinary—Ovarian or Endometrial | AP |
| | Carbo-Tax |
| | CaT |
| | CC |
| | CHAP |
| | CP |
| | CT |
| | Hexa-CAF |
| | PAC |
| | PAC-I (Indiana Protocol) |
| Genitourinary—Prostate | Bicalutamide + LHRH-A |
| | Docetaxel-Estramustine |
| | EM-V see Estramustine/Vinblastine |
| | Estramustine/Vinblastine |
| | FL |
| | FZ |
| | MP |
| | PE |
| | TEC |
| Genitourinary—Renal Cell | Biochemotherapy see Interleukin 2-Interferon alfa 2 |
| | Interleukin 2-Interferon alfa 2 |
| | Interleukin 2-Interferon alfa 2-Fluorouracil |
| Genitourinary—Testicular or Germ Cell | BEP |
| | CISCA II/VB IV |
| | EP |
| | PVB |
| | TIP |
| | VAB-6 |
| | VeIP |
| | VIP |
| Gestational Trophoblastic Neoplasm | CHAMOCA (modified Bagshawe) |
| | MAC III |
| Head and Neck | CABO |
| | CF |
| | CF* |
| | COB |
| | MBC |
| | PFL |
| | TIP |

TABLE C-continued

| Type of Cancer | Name of Combination Chemotherapy Regimen |
|---|---|
| Hepatoblastoma | IPA |
|  | PA-CI |
| Kaposi's Sarcoma | ABV |
| Leukemia-Acute Lymphocytic (ALL) | Advanced-Stage Burkitt's Protocol or B-Cell ALL Pediatric Protocol |
|  | CAL-G |
|  | DVP |
|  | Hyper-CVAD/HD MTX Ara-C |
|  | IDMTX |
|  | IDMTX/6-MP |
|  | Larson Regimen |
|  | Linker Protocol |
|  | MTX/6-M |
|  | MTX/6-MP/VP |
|  | PVA |
|  | PVDA |
|  | TIT |
|  | VAD |
|  | VAD/CVAD |
| Leukemia-Acute Myelocytic (AML) | 5 + 2 |
|  | 7 + 3 |
|  | 7 + 3 + 7 |
|  | ARAC-DNR |
|  | ATRA + CT see DA + ATRA |
|  | CA |
|  | DA |
|  | DA + ATRA |
|  | DAT |
|  | DAV |
|  | DCT |
|  | EMA 86 |
|  | FLAG-Ida |
|  | HDCA |
|  | Hi-C DAZE |
|  | HIDAC |
|  | Idarubicin, Cytarabine, Etoposide (IDA based BF12) |
|  | Idarubicin, Cytarabine, Etoposide (ICE protocol) |
|  | MC |
|  | MV |
|  | TAD |
|  | V-TAD |
| Leukemia—Chronic Lymphocytic (CLL) | CP |
|  | CVP |
|  | Cyclophosphamide-Fludarabine |
|  | Fludarabine-Cyclophosphamide |
| Leukemia—Chronic Myelogenous (CML) | Interferon-Cytarabine-Hydrosyurea |
| Lung—Non-Small Cell | CAMP |
|  | CAP |
|  | CaT |
|  | CT |
|  | CVI |
|  | Docetaxel-Cisplatin |
|  | EC |
|  | EP |
|  | FED |
|  | G + V |
|  | Gemcitabine-Carboplatin |
|  | Gemcitabine-Cis |
|  | Gemcitabine-Vinorelbine |
|  | ICE see MICE |
|  | ICE-T |
|  | MACC |
|  | MICE |
|  | MVP |
|  | PC |
|  | VC |
|  | VIC see CVI |
|  | Vinorelbine-Cisplatin |
|  | Vinorelbine-Gemcitabine |
|  | VIP |
| Lung—Small Cell | ACE |
|  | AVE see CA-VP16 |
|  | CAE see ACE |
|  | CAV |
|  | CAVE |
|  | CAV/EP |
|  | CA-VP16 |
|  | CEV |
|  | CODE |
|  | COPE |
|  | EC |
|  | EP |
|  | ICE see MICE |
|  | MICE |
|  | Paclitaxel-Carboplatin-Etoposide |
|  | VIP |
|  | VP |
| Lymphoma—Hodgkin | ABVD |
|  | B-CAVe |
|  | BCVPP |
|  | BEACOPP |
|  | BVCPP see BCVPP |
|  | CHIVPP |
|  | CHIVPP/EVA |
|  | C-MOPP see COPP |
|  | COMP |
|  | COPP |
|  | CVPP |
|  | EVA |
|  | Mini-BEAM |
|  | MOPP |
|  | MOPP/ABV |
|  | MOPP/ABVD |
|  | MVPP |
|  | NOVP |
|  | OPA |
|  | OPPA |
|  | Stanford V |
| Lymphoma—Non-Hodgkin | Advanced-Stage Burkitt's Protocol or B-Cell ALL Pediatric Protocol |
|  | CDE |
|  | CEPP(B) |
|  | CHOP |
|  | CHOP-BLEO |
|  | CHOP + Rituximab |
|  | C-MOPP see COPP |
|  | CNOP |
|  | CODOX-M/IVAC |
|  | COMLA |
|  | COP |
|  | COPP |
|  | CVP |
|  | DHAOx |
|  | DHAP |
|  | EPOCH |
|  | EPOCH-R |
|  | ESHAP |
|  | FND |
|  | FND + Rituximab, Concurrent |
|  | Hyper-CVAD/HD MTX Ara-C |
|  | ICE + Autologous Stem Cell Transplantation |
|  | MACOP-B |
|  | m-BACOD |
|  | m-BACOD (Reduced Dose) |
|  | M-BACOD |
|  | MINE |
|  | MINE-ESHAP |
|  | ProMACE |
|  | ProMACE/cytaBOM |
|  | ProMAC/MOPP |

TABLE C-continued

| Type of Cancer | Name of Combination Chemotherapy Regimen |
|---|---|
| | R-CHOP see CHOP + Rituximab |
| Melanoma | CDB |
| | CDB + Tamoxifen |
| | CVD |
| | CVD-IL-2I |
| | Dartmouth regimen see CDB + Tamoxifen |
| | DTIC/Tamoxifen |
| Multiple Myeloma | M-2 |
| | MP |
| | VAD |
| | VAD-Liposomal |
| | VBAP |
| | VBMCP |
| | VCAP |
| | VCMP see VMCP |
| | VLAD |
| | VMCP |
| Neuroblastoma | AC |
| | Pt/VM |
| Pancreatic | Gemcitabine-Capecitabine |
| | Gemcitabine-Irinotecan |
| | SMF |
| Renal Cell | Biochemotherapy see Interleukin 2-Interferon alfa 2 |
| | Interleukin 2-Interferon alfa 2 |
| | Interleukin 2-Interferon alfa 2-Fluorouracil |
| Sarcoma | AC |
| | AD |
| | CYVADIC |
| | DI |
| | HDMTX |
| | ICE see MICE |
| | ICE-T |
| | IE |
| | IfoVP |
| | MAID |
| | MICE |
| | MTX-CDDPAdr |
| | Topo/CTX |
| | VAC Pediatric |
| | VAC Pulse |
| | VAC Standard |
| | VACAdr |
| Wilm's Tumor | VAD |

Ligands to Receptors and/or Biomarkers

Therapeutic proteins described herein optionally include covalently bound ligands to receptors and or biomarkers that are present on a cell surface. Therapeutic proteins of particular interest are those that include constituent proteins selected from, e.g., human annexins such as annexin V, annexin VI, annexin V-128, or any annexin V or VI protein containing a cysteine, or annexin V-128, which can also be N-terminally modified by transamination and/or alkylated at a cysteine thiol, or any mutant or extended sequence of annexin V containing a carbonyl group, and any annexin protein fragments or variants thereof which substantially retain the ability to bind to the receptor or binding site, or any combination thereof.

Exemplary ligands for covalent attachment in order to obtain the desired therapeutic protein include, but are not limited to, folate and its derivatives, modified for conjugation to proteins, RGD-motif peptides (Receptor: integrins αV/β3 and αV/β5); NGR-motif peptides (Receptor: aminopeptidase N, also known as CD13); F3, a 34-amino acid basic peptide from HMGN2 (Receptor: cell surface nucleolin); HWGF (selective inhibitors of matrix metalloproteinase-2 and matrix metalloproteinase-9, also known as gelatinase A and gelatinase B; the synthetic peptide CTTHWGFTLC (which targets antiogenic blood vessels, inhibits the migration of human endothelial cells and tumor cells, and also prevents tumor growth and invasion in animal models and improves survival of mice bearing human tumors); and the amino-terminal fragment (ATF) of urokinase (amino acids 1-135 of urokinase A chain). ATF binds to the urokinase receptor, but, unlike full length urokinase, is not internalized.

In other embodiments, therapeutic protein includes a ligand selected from the following group: RGD-motif peptides, folic acid and its derivatives with affinity for folic acid receptors, urokinase, epidermal growth factor (EGF), transforming growth factor-alpha (TGFα), insulin-like growth factor, interleukin-4 (IL-4), interleukin-6 (IL-6), platelet-derived growth factor (PDGF), fibroblast growth factor (FGF), laminin, vascular endothelial growth factor (VEGF), antibodies or antibody fragments (such as, but not limited to, antibodies to the transferrin receptor or the ED-B domain of fibronectin), and the like. The structure and properties of some of the above-listed growth factors are very similar, and therefore, one growth factor may be utilized to target another receptor (for example, TGFα may be utilized to bind to the EGF receptor).

Therapeutic protein may contain a variant of the ligand. For example, it may be desirable to modify a portion of the ligand that has an undesirable biological activity, or it may be desirable to modify a portion of the ligand to enable attachment of the anticancer agent. The only requirement when a variant of the ligand is present in the conjugate is that the ligand variant substantially retains the ligand's receptor or targeting molecule binding activity. Also, sequences may be added to, or inserted within, the ligand during modification, as long as the modified ligand substantially retains the ligand's receptor binding activity. Therefore, it is to be understood that the term "ligand variant" includes both substitutions (including but not limited to conservative and semi-conservative substitutions) as well as additions and insertions to the native ligand's sequence that do not substantially affect the ligand's receptor binding activity. Such variations may occur at the nucleic acid level during construction of the construct from which the conjugate is expressed, or the variations may be produced by other posttranscriptional or posttranslational means known to those or ordinary skill in the art, including but not limited to, mutations and chemical modifications.

The modification of one of the receptor-binding ligands described herein above to provide a fragment or variant thereof that substantially maintains the receptor-binding ability of the native receptor-binding ligand is fully within the skill of a person in the art and therefore is also within the scope of the present invention. The term "substantially maintains the receptor-binding ability of the native receptor-binding ligand" means that the protein fragment or variant maintains at least 50% of the native ligand's receptor-binding ability, and preferably, at least 75% of the native ligand's receptor-binding ability, and more preferably, at least 90% of the native ligand's receptor-binding ability.

In some embodiments, therapeutic proteins optionally further include an anticancer agent (e.g., any of the anticancer agents described herein) that is operatively attached to the ligand, wherein the anticancer agent is selectively toxic to cancer cells, induces their death or inhibits their growth or proliferation.

The ligand of therapeutic protein of the present invention may also be any other targeting protein or composition which binds to the receptor or other targeting molecule uniquely present on the surface of cancer cells or cells in the tumor vasculature (e.g., an aminophospholipid), and, optionally, differs from the proteins that form therapeutic protein (e.g., where therapeutic protein is a monomer or multimer of annexin, the targeting protein is not an annexin protein). When the ligand is a binding protein, the ligand may contain the entire protein that binds to the desired receptor or other targeting molecule, or the ligand may contain only a portion of the binding protein. For example, it may be desirable to remove a portion of the binding protein that has an undesirable biological activity, or it may be desirable to remove a portion of the binding protein to enable attachment of the anticancer agent. The only requirement when a portion of the binding protein is present as the ligand in the conjugate, is that the portion of the protein substantially retain the protein's receptor or targeting molecule binding activity. The terms "portion" and "fragment" are used herein interchangeably.

Examples of receptors that may be targeted by conjugates or multimers in accordance with the present invention include urokinase receptor, epidermal growth factor (EGF) receptor subtypes, insulin-like growth factor receptor, interleukin-4 (IL-4) receptor, interleukin-6 (IL-6) receptor, keratinocyte growth factor (KGF) receptor, platelet-derived growth factor (PDGF) receptor, fibroblast growth factor (FGF) receptor, laminin receptor, vascular endothelial growth factor (VEGF) receptor, transferrin receptor, phosphatidylserine (PS), phosphatidylethanolamine (PE), fibronectin, and the like, as well as portions thereof, and variants thereof, that substantially maintain the ability to bind to the ligand of the conjugate of the present invention and maintain the conjugate on the surface of the cell with substantially no internalization thereof. In some embodiments, the ligand for the receptor may be selected from the group consisting of urokinase, epidermal growth factor (EGF), transforming growth factor-alpha (TGFα), insulin-like growth factor, interleukin-4 (IL-4), interleukin-6 (IL-6), platelet-derived growth factor (PDGF), fibroblast growth factor (FGF), laminin, vascular endothelial growth factor (VEGF),)

Therapeutic proteins of the present invention provides several advantages of the methodologies of the prior art. First, since the anticancer agent is being targeted to cells that it is intended to kill, or the vasculature supplying the cells that it is intended to kill, the dosages of the conjugate containing the anticancer agent should be significantly lower than when the anticancer agent alone is administered systemically. The interaction between the ligand of the conjugate and its respective receptor will displace the native ligand (such as urokinase or a growth factor) from the receptor, and, when the native ligand is involved in the invasive ability or biological advantage of the cancer cells, will greatly inhibit the proliferation and/or invasive ability of the cancer cells.

Polypeptide Biologically Active Agents

In still other embodiments, the biologically active agent covalently attached to therapeutic protein is a polypeptide. Optionally, the biologically active polypeptide differs from the proteins that form therapeutic protein (e.g., where therapeutic protein is a monomer or multimer of annexin, the biologically active polypeptide is not an annexin protein). Exemplary biologically active polypeptides include, but are not limited to, pituitary hormones such as vasopressin, oxytocin, melanocyte stimulating hormones, adrenocorticotropic hormones, growth hormones; hypothalamic hormones such as growth hormone releasing factor, corticotropin releasing factor, prolactin releasing peptides, gonadotropin releasing hormone and its associated peptides, luteinizing hormone release hormones, thyrotropin releasing hormone, orexins, and somatostatin; thyroid hormones such as calcitonins, calcitonin precursors, and calcitonin gene related peptides; parathyroid hormones and their related proteins; pancreatic hormones such as insulin and insulin-like peptides, glucagon, somatostatin, pancreatic polypeptides, amylin, peptide YY, and neuropeptide Y; digestive hormones such as gastrin, gastrin releasing peptides, gastrin inhibitory peptides, cholecystokinin, secretin, motilin, and vasoactive intestinal peptide; natriuretic peptides such as atrial natriuretic peptides, brain natriuretic peptides, and C-type natriuretic peptides; neurokinins such as neurokinin A, neurokinin B, and substance P; renin related peptides such as renin substrates and inhibitors and angiotensins; endothelins, including big endothelin, endothelin A receptor antagonists, and sarafotoxin peptides; and other peptides such as adrenomedullin peptides, allatostatin peptides, amyloid beta protein fragments, antibiotic and antimicrobial peptides, apoptosis related peptides, bag cell peptides, bombesin, bone Gla protein peptides, CART peptides, chemotactic peptides, cortistatin peptides, fibronectin fragments and fibrin related peptides, FMRF and analog peptides, galanin and related peptides, growth factors and related peptides, G therapeutic peptide-binding protein fragments, guanylin and uroguanylin, inhibin peptides, interleukin and interleukin receptor proteins, laminin fragments, leptin fragment peptides, leucokinins, mast cell degranulating peptides, pituitary adenylate cyclase activating polypeptides, pancreastatin, peptide T, polypeptides, virus related peptides, signal transduction reagents, toxins, and miscellaneous peptides such as adjuvant peptide analogs, alpha mating factor, antiarrhythmic peptide, antifreeze polypeptide, anorexigenic peptide, bovine pineal antireproductive peptide, bursin, C3 peptide P16, tumor necrosis factor, cadherin peptide, chromogranin A fragment, contraceptive tetrapeptide, conantokin G, conantokin T, crustacean cardioactive peptide, C-telopeptide, cytochrome b588 peptide, decorsin, delicious peptide, delta-sleep-inducing peptide, diazempam-binding inhibitor fragment, nitric oxide synthase blocking peptide, OVA peptide, platelet calpain inhibitor (P1), plasminogen activator inhibitor 1, rigin, schizophrenia related peptide, serum thymic factor, sodium potassium A therapeutic peptidease inhibitor-1, speract, sperm activating peptide, systemin, thrombin receptor agonists, thymic humoral gamma2 factor, thymopentin, thymosin alpha 1, thymus factor, tuftsin, adipokinetic hormone, uremic pentapeptide, glucose-dependent insulinotropic polypeptide (GIP), glucagon-like peptide-1 (GLP-1), glucagon-like peptide-2 (GLP-1), exendin-3, exendin-4, and other therapeutic peptides or fragments thereof. Additional examples of peptides include ghrelin, opioid peptides (casomorphin peptides, demorphins, endorphins, enkephalins, deltorphins, dynorphins, and analogs and derivatives of these), thymic peptides (thymopoietin, thymulin, thymopentin, thymosin, Thymic Humoral Factor (THF)), cell adhesion peptides, complement inhibitors, thrombin inhibitors, trypsin inhibitors, alpha-1 antitrypsin, Sea Urchin Sperm Activating Peptide, SHU-9119 MC3-R & MC4-R Antagonist, glaspimod (immunostimulant, useful against bacterial infections, fungal infections, immune deficiency immune disorder, leukopenia), HP-228 (melanocortin, useful against chemotherapy induced emesis, toxicity, pain, diabetes mellitus, inflammation, rheumatoid arthritis, obesity), alpha 2-plasmin inhibitor (plasmin inhibitor), APC tumor suppressor (tumor suppressor, useful against neoplasm), early pregnancy factor (immunosuppressor), endozepine diazepam binding inhibitor (receptor peptide), gamma interferon (useful against leukemia), glandular kallikrein-1 (immunostimulant), placental ribonuclease inhibitor, sarcolecin binding protein, surfactant protein D, Wilms' tumor suppressor, GABAB 1b receptor peptide, prion related peptide (iPrPl3), choline binding protein fragment (bacterial related peptide), telomerase inhibitor, cardiostatin peptide, endostatin derived peptide (angiogenesis inhibitor), prion inhibiting peptide, N-methyl D-aspartate receptor antagonist, C-peptide analog (useful against diabetic complications), RANTES, NTY receptors, NPY2-R (neuropeptide Y type 2-receptor) ligands, NC4R peptides, or fragments thereof. See U.S. Pat. No. 6,849,714, which is incorporated by reference herein. Also included are Alpha-1 antitrypsin, Angiostatin, Antihemolytic factor, antibodies, Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GRO.quadrature./MGSA, GRO, GRO, MIP-1, MIP-1, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-.alpha., IFN-.beta., IFN-.gamma.), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase, Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGF), Urokinase, T-20, SS-14, LHRH, erythropoietin (EPO), G-CSF, TPO, axokine, leptin, and many others. Examples of hA conjugated, linked, or fused to biologically active molecules may be found in U.S. Pat. Nos. 7,056,701; 7,041,478; 7,045,318; 6,994,857; 6,987,006; 6,972,322; 6,946,134; 6,926,898; 6,905,688; 6,686,179; 6,548,653; 6,423,512; 5,773,417; and 5,594,110, which are incorporated by reference herein.

Annexins

As provided herein, therapeutic proteins that include annexins can be of particular utility such as annexin V and annexin V-128.

In any of the embodiments herein, the annexin is a human annexin, or is a protein that has at least 75%, at least 80%, at least 85%, at least 90%, or at least 95% sequence identity to human annexin. In still other embodiments, the annexin is human annexin V or is a protein that has at least 75%, at least 80%, at least 85%, at least 90%, or at least 95% sequence identity to human annexin V. For example, in some embodiments, the annexin is human annexin V (SEQ ID NO:1) (Accession P08758) provided in Table D, or is a protein that has at least 75%, at least 80%, at least 85%, at least 90%, or at least 95% sequence identity to the protein.

TABLE D

| SEQ ID NO: 1 | | | |
|---|---|---|---|
| 10 | 20 | 30 | 40 |
| MAQVLRGTVT | DFPGFDERAD | AETLRKAMKG | LGTDEESILT |
| 50 | 60 | 70 | 80 |
| LLTSRSNAQR | QEISAAFETL | FGRDLLDDLK | SELTGKFEKL |
| 90 | 100 | 110 | 120 |
| IVALMKPSRL | YDAYELKHAL | KGAGTNEKVL | TEIIASRTPE |
| 130 | 140 | 150 | 160 |
| ELRAIKQVYE | EEYGSSLEDD | VVGDTSGYYQ | RMLVVLLQAN |
| 170 | 180 | 190 | 200 |
| RDPDAGIDEA | QVEQDAQALF | QAGELKWGTD | EEKFITIFGT |
| 210 | 220 | 230 | 240 |
| RSVSHLRKVF | DKYMTISGFQ | IEETIDRETS | GNLEQLLLAV |
| 250 | 260 | 270 | 280 |
| VKSIRSIPAY | LAETLYYAMK | GAGTDDHTLI | RVMVSRSEID |
| 290 | 300 | 310 | 320 |
| LFNIRKEFRK | NFATSLYSMI | KGDTSGDYKK | ALLLLCGEDD |

Annexin V-128 is described in, e.g., Jin et al., *Journal of Biological Chemistry*, 279:40351-347, 2204. Annexin V-128 is a recombinant human protein that is similar to wild-type human annexin 1, but with three modifications: an N-terminal extension of (Met)-Ala-Gly-Gly-Cys-Gly-His; deletion of the initiator Met at position 1 of wild-type annexin V; and 3) a point mutation of Cys-316 to Ser. Id. In any of the embodiments herein, the annexin is annexin V-128, or is a protein that has at least 75%, at least 80%, at least 85%, at least 90%, or at least 95% sequence identity to annexin V-128.

During the past decade, the utility of annexin V has evolved from a focus on detection of apoptotic cells in vitro, to an in vivo molecular imaging technology with potential clinical use. A key discovery, the specific internalization properties of annexin V, has enhanced the opportunity to use annexin V as a basis for therapeutic applications. PS, an anionic phospholipid restricted to the cytoplasmic surface of plasma membranes in most cells, is externalized to the surface of apoptotic cells, certain tumor cells, and viruses. van Genderen et al. (Extracellular annexin V: functions of phosphatidylserine-binding and two-dimensional crystallization. Biochim Biophys Acta. 2008, 1783(6):953-63.) reported that annexin V opens a portal of cell entry on the PS-expressing cell. Annexin V not only binds tightly to PS but also forms a two-dimensional network on the surface that causes its internalization concomitantly with covalently attached entities. Although strategies for localizing annexin conjugates with concomitant release of anticancer drugs in the vicinity of cancer cells may suffice for delivery of effective therapy, The specific internalization properties of annexin V provides additional incentive to use this protein as a carrier of entities that can ameliorate disease by targeting them for delivery to cells possessing high affinity for annexin V The possibility for targeting pharmacological compounds to the intracellular compartments of PS-expressing cells would be considerably advanced by site-specific modification of annexin V and its variants and the formation of homogeneous adducts.

Thus, the feasibility of utilizing annexin V as a delivery system to cells undergoing apoptosis is based in part on the fact that annexin V can be conjugated to a wide range of reporter compounds without significantly impairing its PS binding and consequently its apoptotic cell-binding properties. This phenomenology opens possibilities for targeting pharmacological compounds to the intracellular compartments of PS-expressing cells. There is evidence, as well, that annexin V can also bind living cells such as tumor cells and enter the living cell upon binding to it. PS is exposed on the surface of vascular endothelial cells within the blood vessels of tumors, but not on normal endothelium (S. Ran, A. Downes, P. E. Thorpe, Increased exposure of anionic phospholipids on the surface of tumor blood vessels, Cancer Res. 62 (2002) 6132-6140; S. Ran, P. E. Thorpe, Phosphatidylserine is a marker of tumor vasculature and a potential target for cancer imaging and therapy, Int. J. Radiat. Oncol. Biol. Phys. 54 (2002) 1479-1484).

There is also abundant evidence that PS is expressed on the outer surface of tumor cells (T. Utsugi, A. J. Schroit, J. Connor, C. D. Bucana, I. J. Fidler, Elevated expression of phosphatidylserine in the outer membrane leaflet of human tumor cells and recognition by activated human blood monocytes, Cancer Res. 51 (1991) 3062-3066; M. Sugimura, R. Donato, V. V. Kakkar, M. F. Scully, Annexin V as a probe of the contribution of anionic phospholipids to the procoagulant activity of tumour cell surfaces, Blood Coagul. Fibrin. 5 (1994) 365-373.

A further basis for cancer therapeutics comes from the work of X. Yan et al. (Cancer Immunol. Immunother. Annexin V promotes anti-tumor immunity and inhibits neuroblastoma growth in vivo. 2012, Apr. 5. DOI 10.1007/s00262-012-1250-4) that provides the stimulus for the construction of annexin dimers and multimers that will bind tightly to PS and promote anti-tumor immunity.

These observations provide a compelling rationale for annexin-mediated cellular targeting of anticancer drugs to tumor cells.

The broad utilization of annexin proteins as delivery systems to cancer cells, or cells undergoing apoptosis benefits from methods where proteins can be conjugated to a wide range of organic compounds and biologicals, without significantly impairing the conjugate's ability to bind PS, and consequently their apoptotic or cancer cell-binding properties. It has been demonstrated that site specificity is critical in maintaining the intrinsic affinity of annexin V for phosphatidylserine and the non-specific labeling of this protein can severely limit the binding of annexin conjugates to PS. A significant advantage of the methodology described herein is the ability to site-specifically introduce functionality onto the framework of annexin proteins (e.g., annexin V and annexin V-128) and link such functions to various payloads, many of which are biologically active entities. Indeed, an appreciation of the differential reactivity of annexin proteins that we have achieved has guided the development of our methodology which has been dependent on experimental observations of comparative reactivities of said proteins.

A strategy for destroying cancer cells and tumors specifically is thus provided by the annexins, a family of highly homologous antithrombotic proteins of which ten are expressed in several human tissues (Benz and Hofmann, Biol. Chem. 378:177-183 (1997). Annexins share the property of binding calcium and negatively charged phospholipids, both of which are required for blood coagulation. Under physiological conditions, negatively charged phospholipid is mainly supplied by phosphatidylserine (PS) in activated or damaged cell membranes. In intact cells, PS is confined to the inner leaflet of the plasma membrane bilayer and is not accessible on the surface.

Several annexins, including I, II, IV, V, and VIII, bind PS with high affinity. Annexin V binds PS with very high affinity ($K_d$=1.7 nmol/L), greater than the affinity of factors X, Xa, and Va for negatively charged phospholipids (Thiagarajan and Tait, J. Biol. Chem. 265:17420-17423 (1990).

These observations provide a compelling rationale for annexin mediated cellular targeting of anticancer drugs to such blood vessels and tumor cells. Annexin V-mediated internalization creates a novel therapeutic platform for targeted drug delivery and cell entry to treat various diseases, including cancer and cardiovascular disease. Through linkage of the chemotherapeutic drug to a macromolecular carrier, such as an annexin protein, the volume of distribution of the free drug is significantly reduced and the concentration of free drug can be directed toward, and concentrated in the tumor or the tumor endothelium, resulting in a decrease in the amount and types of non-specific toxicities, and an increase in the amount of drug that can be effectively delivered to the tumor per dosed equivalent of the drug entity. This strategy is employed in one embodiment of the invention involving the site-specific labeling of annexin with small molecule entities. In a second embodiment of this invention two or more annexin proteins, either the parent or modified forms, are linked together via chemical modification or recombinant DNA technology to increase the duration of action of annexins as circulating proteins in therapeutic applications.

Site-Specific Synthesis of Therapeutic Proteins

In spite of the utility of targeted therapy of combinations of drugs delivered to a common tumor site in a controlled manner, chemical methods have been lacking for the site-specific conjugation of each organic chemical entity (including drugs and homing agents) to their own exclusive site in the construction of therapeutic proteins (e.g., an annexin conjugate). Such strategies would be particularly useful for the preparation of proteins that include multiple therapeutic agents in order to provide an advantageous strategy for combination therapy. In order to realize the benefits of multiple therapeutic entities on a scaffold and avoid heterogeneous mixtures which compromise development, manufacturing and regulatory compliance, site-specific conjugative methods are required.

Additional beneficial effects can result from the use of multimeric proteins, which can afford beneficial clinical effects such as improved circulation times. To meet the threshold requirements, this invention discloses methods and composition of matter that relate to protein multimers, including multimers of annexin, annexin fusion proteins, and their chemical modifications which have extended circulation times compared to annexin monomers.

Further, certain annexin-labeled nanoparticles such as annexin crossed-linked iron oxide (H. Chen et al., Nanomedicine. 2012, 8, 291-8) particles have extended blood half-lives in mice which can used in therapeutic proteins described herein Described herein are methods for the site-specific attachment of entities at the N-terminus of annexin fusion proteins and/or at the cysteine thiols. These methods make feasible the goal of preparing homogeneous fusion protein conjugates bearing multiple therapies, in particular organic chemical pharmacophores, targeted for specific cancer cell surfaces.

Analytically, a necessary condition for the determination of site specificity is the observation by mass spectrometry, that one equivalent of a reactive entity with a target protein leads only to a single new mass corresponding to theoretical mass. For example, addition reactions to the protein should result in the combined mass of protein and reactive entity only, if site specificity has been achieved. This criterion is easy to apply as site specific reactions exhibit only one new mass even when 95%-100% of the protein has been consumed. Invariably, non-specific reactions exhibit multiple masses indicative of labeling multiple residues, before the target protein has been consumed. Thus even by inspection of the mass spectrogram non-specific reactions are evident.

A more stringent criterion that has been employed involves enzyme digestion of the monolabeled species followed by analysis by mass spectrometry (a technique well established in the art) which is used to determine the precise site of labeling.

In one embodiment we have been able to substantially (usually quantitatively) transaminate annexin V or annexin V-128 and generate proteins with carbonyl amides at their termini. These transaminated proteins are subject to further modification with carbonyl reagents such as aminoxy, hydrazide, Pictet-Spengler ligation reactions ((P. Agarwal, A Pictet-Spengler ligation for protein chemical modification. Proc Natl Acad Sci USA. 2013 110, 46-51), and with amines as substrates for reductive amination. Indeed, we have achieved high yields, in some cases quantitative, of carbonyls installed in proteins using aniline substrates. Alternatively, selective acylation of the annexin proteins has been accomplished using kinetically controlled techniques, in which the protein is in excess under first order conditions. These selective condensation reactions provide a basis for site-specifically linking entities to annexin proteins, in general.

In other embodiments we have been able to uncover empirical distinctions for site-selectively modifying the cysteine thiols of annexin proteins. We have been able to attach various modules containing multi-therapeutically relevant entities as a function of thiol nucleophilicity and its local environment. For example, we have determined that whereas α-halomethylketones generally are capable of alkylating either annexin V and annexin V-128 thiol-specifically, propargyl and allyl halides, maleimides, halo-acetamides, acrylamides, and benzyl halide substrates are thiol-specific only against annexin V-128.

The preparation of annexin conjugates bearing multiple entities can be accomplished attaching each entity directly to a unique amino acid, provided site-specific methods are available to install the entities at their respective unique sites along the protein surface. A second approach would be to attach entities to a compact template to create a series of payloads that can ultimately be linked simultaneously to the protein carrier, and this latter approach can therefore afford numerous advantages.

First and foremost, standard small molecule synthetic methods can be employed to specifically position entities on the template. Secondly, standard methods of analysis can be employed to unambiguously characterize the modified template adorned with the desired entities. After all the necessary features are assembled and in place on the "payloaded" template, it can then be attached in a final step using click chemistry techniques. Finally, pre-assembling the template as an accessory to the fusion protein allows for the use of numerous templates, provided they are chemically compatible with protein systems and meet the bioavailability requirements of the ultimate therapeutic agent.

In the current state of the art, informed opinion regards combination therapy as key to most cancer treatments for cancer, rather than the use of any one individual drug. Indeed, the specific targeting of combinations of powerful cytotoxic agents is compelling. In this context, to maximize anticancer activities of an agent and obtain useful synergies, the anti-tumor immunity reported for annexin V can be augmented with chemotherapeutics, anti-angiogenics, ligands to cancer cell surface biomarkers, and the like. Accordingly, chemical strategies for linkage of each of these entities are represented below.

Modification of Annexins

An important embodiment of this invention is the ability to use chemical modification to prepare multimers of annexin proteins as well as multimers of annexin conjugates. Annexin V blockade of PS can enhance T cell mediated tumor immunity and inhibit tumor growth. Since the specificity of anticancer agents, growth, and proliferation of tumors can also be controlled using various ligands, coupling them to annexin V can leverage the enhanced tumor immunity observed for parent annexin. For a specific cancer application, the circulation times of annexin proteins and their conjugates can limit efficacies, if the proteins or their conjugates are too rapidly eliminated from the circulation. Critical mass for overcoming the renal filtration threshold of 68,000 Da can be achieved through fusion protein technology. Diannexin has been produced by such means and is being used to treat reperfusion-ischemia injury and we claim it as a use for treatment of cancer in humans and domestic pets. Other recombinant methods can create multimers with functionalities to which organic chemical entities can be appended such as the use of formyl glycine generating enzymes (Rush et al., J. Am. Chem. Soc., 2008, 130 (37), 12240-12241).

It is especially advantageous to modify annexin using organic chemistry to introduce diverse functionality to link annexins to various entities, e.g., drugs, ligands to cell surface biomarkers, and/or to protein molecules to optimize therapeutic properties in the circulation. Crosslinking of proteins via chemical modification allows considerably more flexibility than DNA recombinant technology alone, which is restricted to establishing peptide bonds in a linear sequence. In the particular case of annexin, the intrinsic ability to promote tumor immunity can be further exploited by (1) adding various ligands that can be transported to the surface or interior of target cancer cells, (2) by attaching ligands to an additional biomarker to more precisely target annexin to specific cancer cells, and (3) other proteins with additional biological properties or that positively impact pharmacokinetics. Conjugates of annexin proteins whose masses place them above the renal filtration threshold of M.W. 68,000 Da, can be generated in a number of ways, through the formation of multimers via recombinant DNA technology, the formation of multimers via chemical modification, or via pegylation of annexin V or its variants or mutants.

We have devised a number of methods to couple proteins or their modifications to utilize the potential advantages of having multimeric forms or pegylated formats. For example, pegylated forms of annexin and multimers that exceed the renal filtration threshold of 68,000 Da should find use as entities that block phosphatidylserine with prolonged duration of action and we have prepared several of such species that are outlined herein. It is noteworthy that multimers of annexin proteins such as diannexin are also subject to the same chemistry as monomeric annexin, with modified stoichiometries. For example, the fusion protein, diannexin, can be functionalized at both cysteines, but only one N-terminal exists for transamination. Exemplary strategies using carbonyl and thiol functionality are described herein.

Protein Modification to Install Sites for Cross-Linking or Conjugation

Carbonyl Strategy

For example, we have been able to substantially transform annexin proteins such as annexin V and annexin V-128 ((1)=annexin protein) at their N-termini and produce carbonyl amides, specifically N-terminal ketoamides (2), Scheme 1. which offer opportunities for attaching a broad range of linkers onto the protein mainframe.

Scheme 1. Conversion of proteins to N-terminal carbonylamides

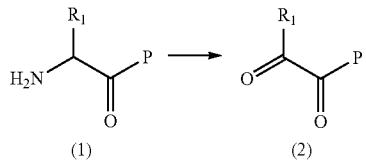

P = protein; $R_1$ = H, $CH_3$, amino acid side chain

For example, we have been able to condense bifunctional carbonyl reagents with alkoxyl amines ($X_1$ or $X_2$=O), or hydrazide functionality ($X_1$ or $X_2$=C=ONH)) with the N-terminal α-carbonylamides (Scheme 2). In a third step, stemming from the foregoing condensation of bifunctional reagents (3) to provide reactive nucleophilic handles as shown in (4), we have been able to further functionalize the nitrogen nucleophiles with a broad range of aldehyde and ketones (not shown). In fact with annexin proteins we have determined that there is a preference for oxime formation over hydrazone formation with am-aminoxy-hydrazides and that such reagents will selectively form oximes with the N-terminal ketoamide.

Scheme 2. Condensation of bifunctional agents with N-terminal α-carbonylamides of proteins

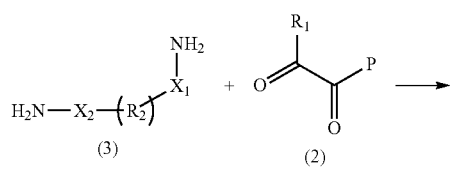

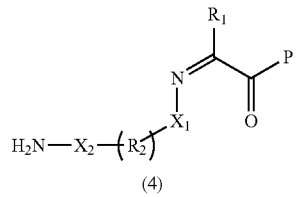

$X_1, X_2$ = O, NH, CONH
$R_1$ = H, $CH_3$, amino acid side chain
$R_2$ = $(CH_2)_m(OCH_2CH_2)_p$
m = 1-8; p = 0-1000, P = protein functionality Indeed, N-terminal carbonyl amides afford two paths to crosslinking biologically active entities to proteins. One path involves a two-step sequence in which condensation of an equivalent of a homo- or hetero-bifunctional crosslinker, with a modified protein containing an aldehyde or ketone function, provides protein with a novel reactive nitrogen nucleophile to give modified proteins as in (4), Figure 2 (illustrated for an α-carbonylamide, but applicable to aldehydes and ketones installed in proteins via DNA recombinant technology). In the second reaction the nitrogen nucleophile is condensed with an appropriate biological entity (payload) containing an aldehyde or ketone function (5) to complete the crosslinking (Scheme 3).

Scheme 3. Crosslinking of payloads to proteins mediated by proteins including α-nucleophiles.

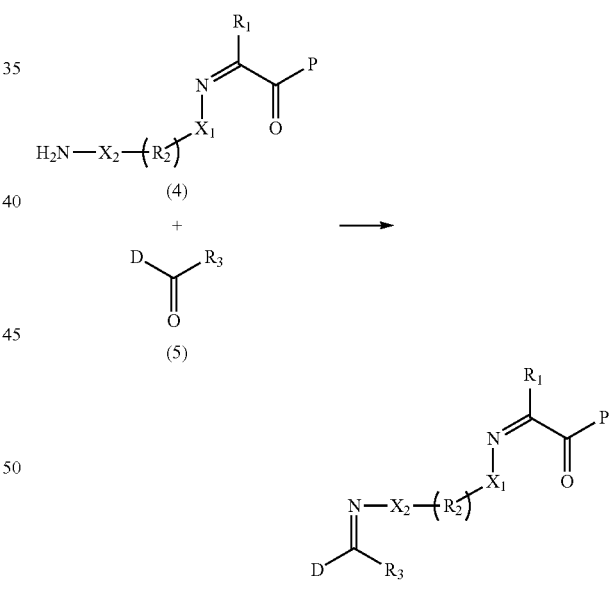

$X_1, X_2$ = O, NH, CONH
$R_1$ = H, $CH_3$, amino acid side chain
$R_2$ = $(CH_2)_m(OCH_2CH_2)_p$
m = 1-8; p = 0-1000, P = protein functionality Another option is to first prepare the biologically active entity for linkage to one equivalent of the crosslinker (4) and then condense the resulting mono-adduct (7) at the site of carbonyl modification of the protein of interest (Scheme 4). Exemplary key steps for anthracycline drugs are indicated below for both pathways in Scheme 5 and Scheme 6.

Scheme 4. Crosslinking of payloads (5) to carbonyl-containing proteins mediated by payload-linker conjugates (7).
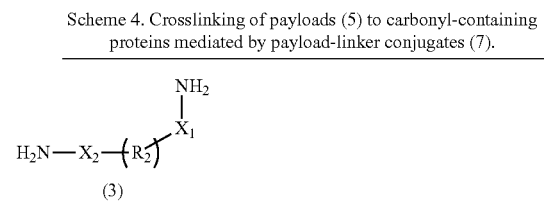
$X_1, X_2 = O, NH, CONH$
$R_1 = H, CH_3$,
amino acid side chain
$R_2 = (CH_2)_m(OCH_2CH_2)_p$
$m = 1-8; p = 0-1000$,
P = protein functionality
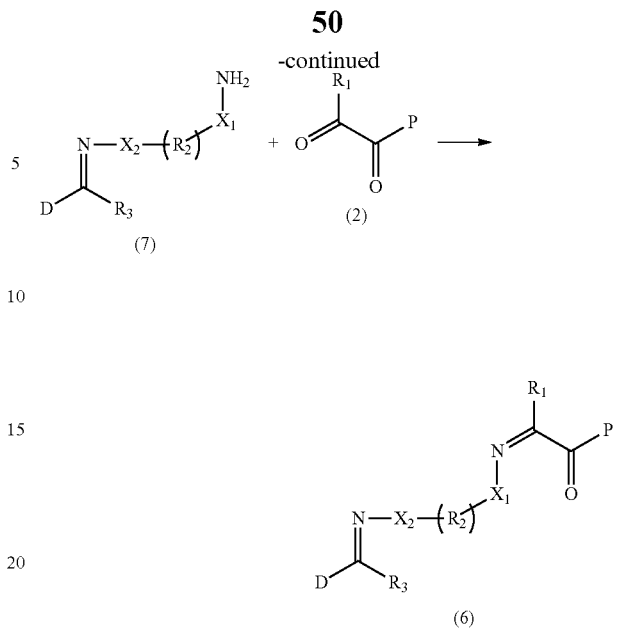
Scheme 5. Crosslinking of anthracycline drugs (8) to proteins containing α-nucleophiles (4).
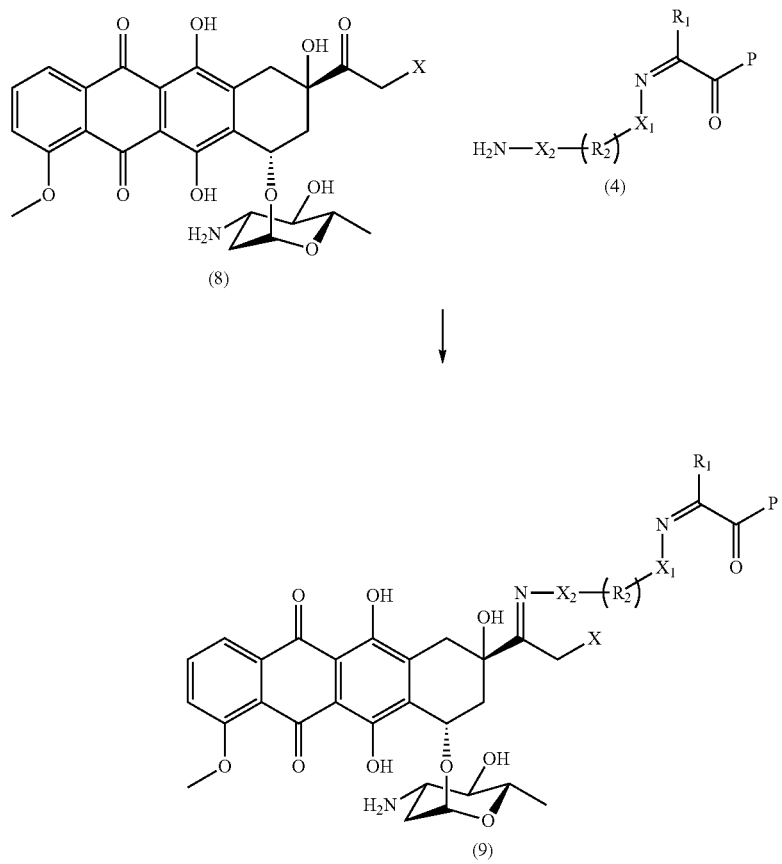
$X_1, X_2 = O, NH, CONH$
X = H, OH
$R_1 = H, CH_3$
$R_2 = (CH_2)_m(OCH_2CH_2)_p$
$m = 1-8; p = 0-1000$ Scheme 6. Crosslinking of anthracycline drugs (8) to carbonyl-containing proteins by initial functionalization using bifunctional carbonyl reactive nucleophiles (3).

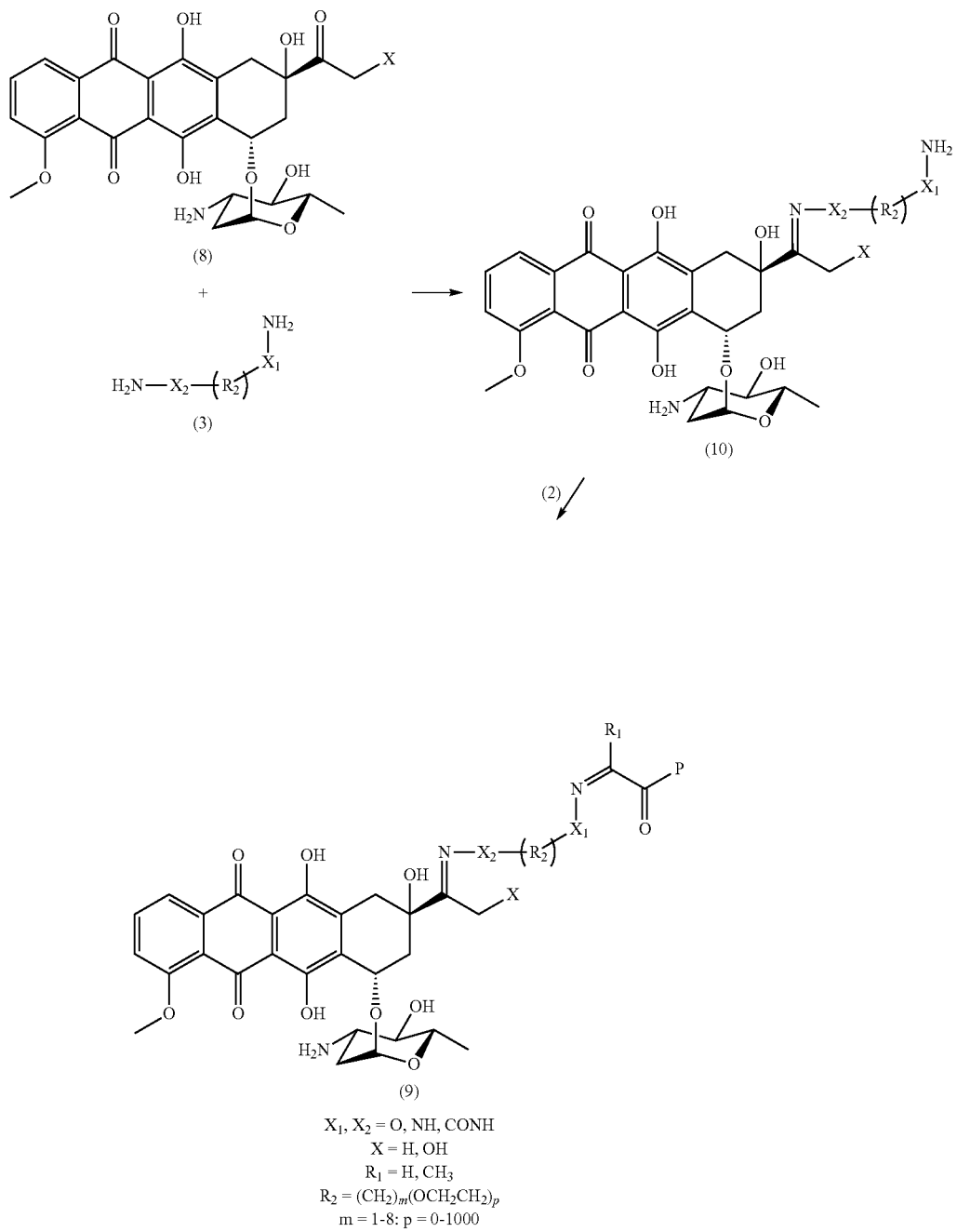

$X_1, X_2 = O, NH, CONH$
$X = H, OH$
$R_1 = H, CH_3$
$R_2 = (CH_2)_m(OCH_2CH_2)_p$
$m = 1\text{-}8; p = 0\text{-}1000$ For molecules that do not contain functionality for direct attachment as above for the anthracyclines, they can often be modified to contain the requisite functionality for crosslinking. For example, in Scheme 7, Taxol payloads can be prepared for crosslinking by acylating the secondary hydroxyl group of (11) by standard procedures used to introduce levulinic acid and like moieties known in the art. The adduct (12) can then be treated with either the bifunctional reagents (3), or attached directly to (4), not shown.

Scheme 7. Modification of taxol drugs to enable crosslinking to carbonyl-containing proteins.
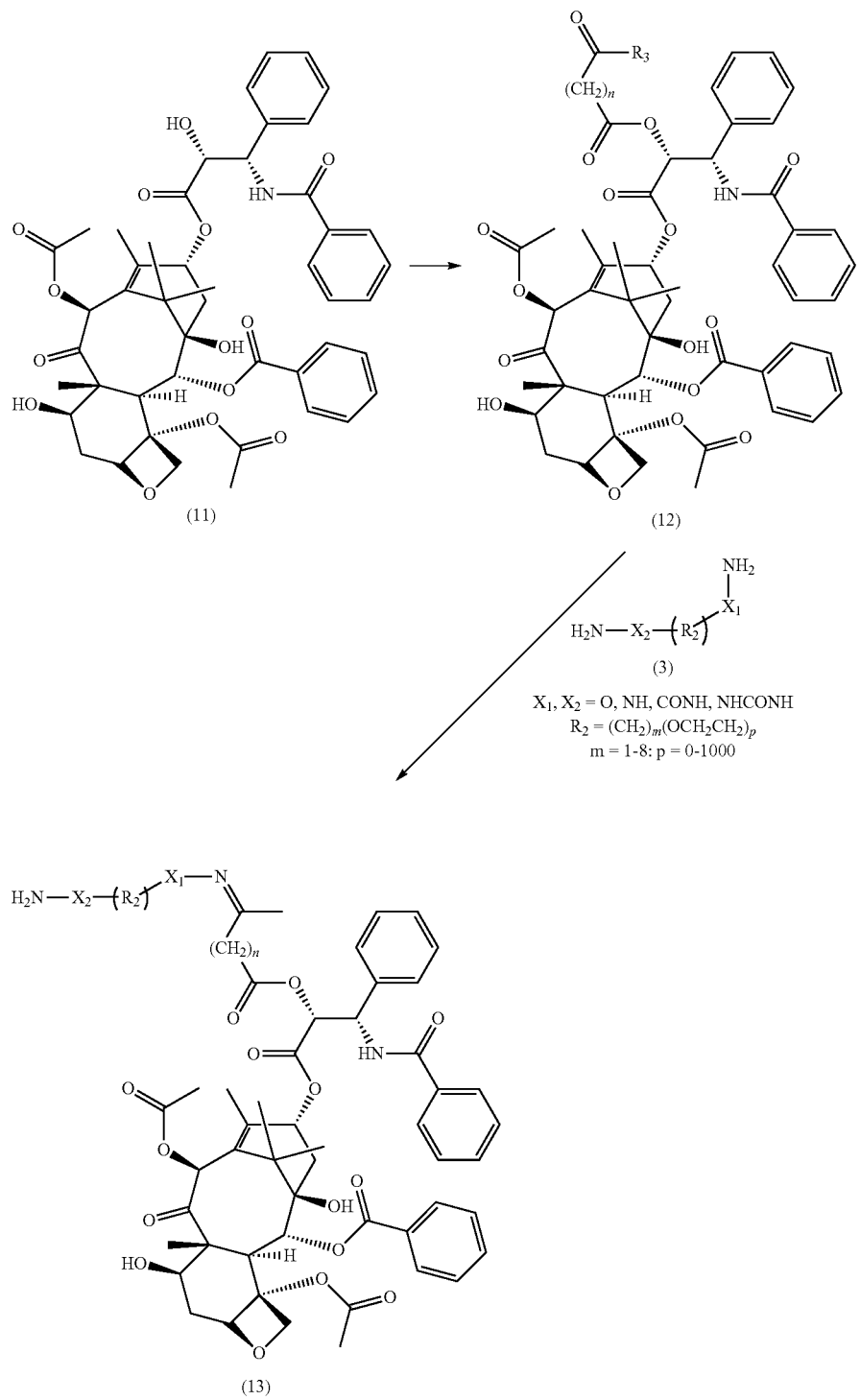
Alternatively, the secondary hydroxyl group in (11) (Scheme 8) can be acylated using aryl substrates bearing carbonyl substituents, that can serve as substrates as per the above pathway.

Scheme 8. Utilization of carbonyl-containing taxol derivatives for crosslinking to carbonyl-containing proteins.

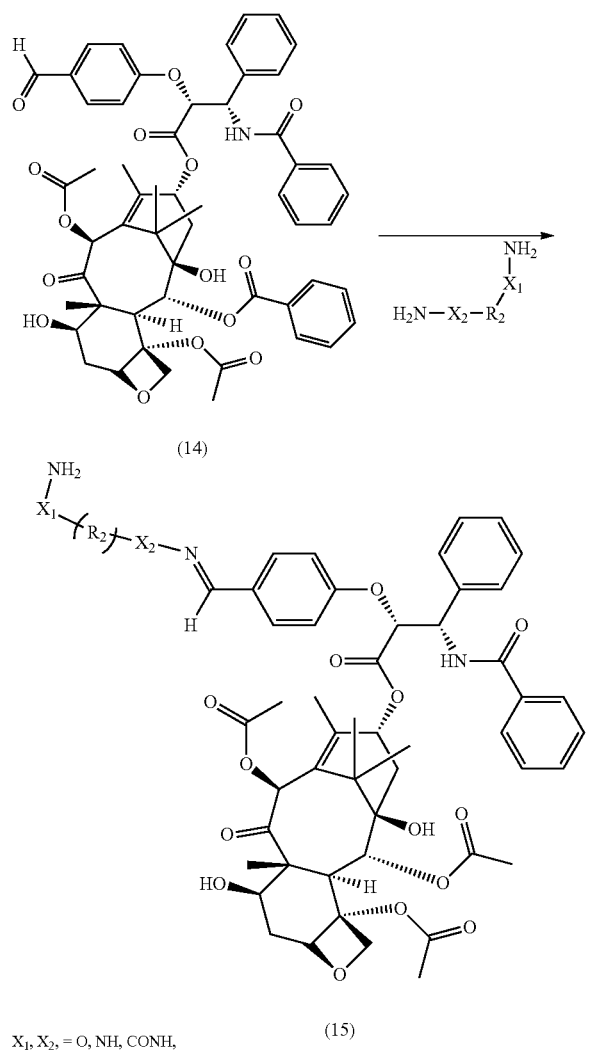

X$_1$, X$_2$, = O, NH, CONH, NHCONH
R$_2$ = (CH$_2$)$_m$(OCH$_2$CH$_2$)$_p$
m = 1-, 8: p = 0-1000

Camptothecin (16) (Scheme 9) is another example of an anticancer drug that can be prepared for crosslinking via the routes above. It can be acylated at its tertiary hydroxyl and prepared for attachment to the carrier protein to give the precursors denoted by structures of formula (17).

Scheme 9. Functionalization of camptothecin for crosslinking to proteins using carbonyl or azides as points of attachement.

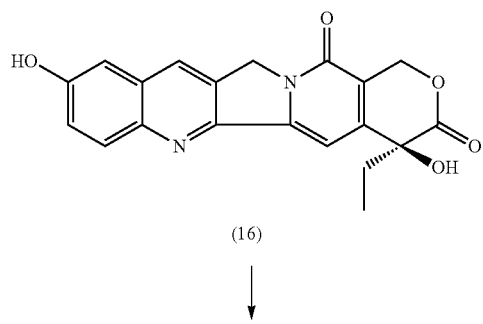

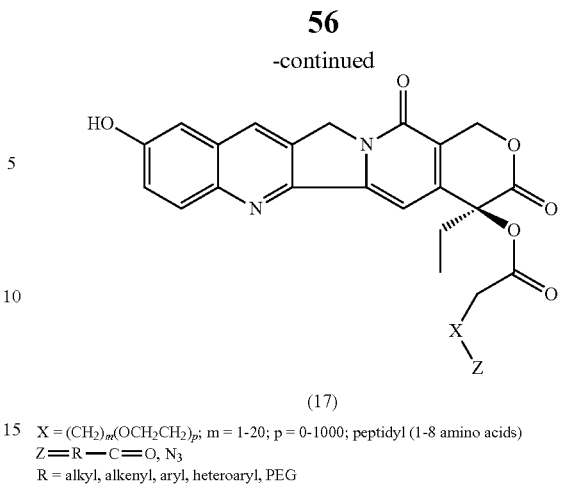

X = (CH$_2$)$_m$(OCH$_2$CH$_2$)$_p$; m = 1-20; p = 0-1000; peptidyl (1-8 amino acids)
Z═R—C═O, N$_3$
R = alkyl, alkenyl, aryl, heteroaryl, PEG We have also been able to site-specifically transaminate annexin proteins at their N-termini. The transamination can provide opportunities for reductive amination and reaction with carbonyl reagents which are shown in Scheme 10 to provide alkynes (19) and (21) or the corresponding azides (not shown). Indeed, the click chemistry, azide-alkyne combination, can be inversely designed with the protein bearing the azide at the N-terminus and the payload entity possessing an alkyne. Carbonyl entities can also be introduced by recombinant DNA methodologies (D. Rabuka et al. Site-specific chemical protein conjugation using genetically encoded aldehyde tags. Nat Protoc. 2012, 7, 1052-67; C. C. Liu and P. G. Schultz, Adding new chemistries to the genetic code. Annu Rev Biochem. 2010, 9, 413-44). Note that the examples in Scheme 10 of annexin modifications that can be combined with azide-bearing payloads preserve the cysteine for thiol-specific reactions.

Scheme 10. N-terminal Transamination of Annexin Proteins and Nitrogen Coupling Reactions.

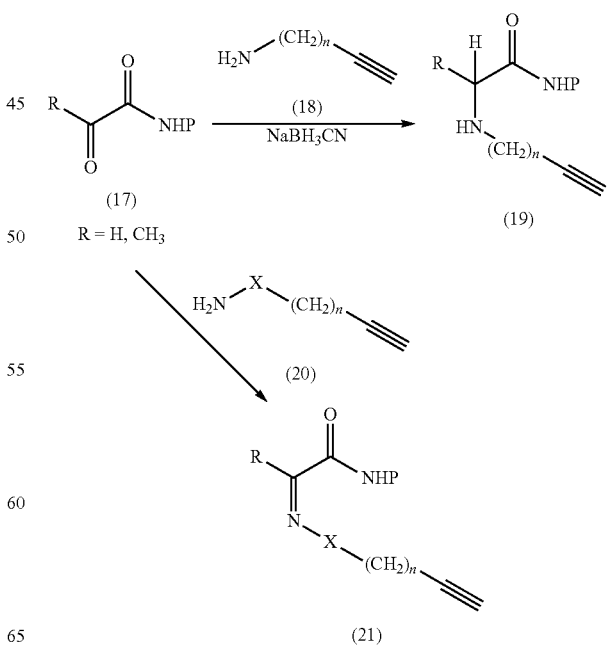

R = H, CH$_3$

Thiol Strategy

For proteins (e.g., annexin proteins) containing free cysteines, a further option is available as a free cysteine can be functionalized using thiol-specific reagents.

Indeed, annexins with solvent accessible cysteine thiols, such as annexin V-128 can be propargylated quantitatively, and undergo cycloaddition reactions as shown in Scheme 11.

Scheme 11. Site-specific Propargylation of Annexin Proteins and Coupling with Azide-linked Payloads.

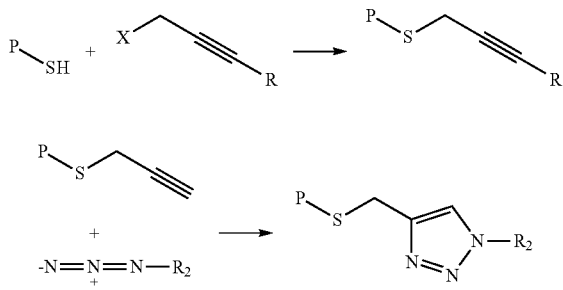

PSH = annexin protein; R = alkyl, aryl alkaryl, heteroaryl carboalkoxy, sulfonyloxy Beyond propargylation of select annexin cysteines, we have also been able to utilize α-bromopyruvate to functionalize annexin thiols to give pyruvyl-annexins, as well as benzylbromides to give certain derivatized annexins. Both reaction types are subject to further modification by carbonyl reactions alluded to above (Scheme 12).

Scheme 12. Thiol-specific Reactions of Annexins Applicable to the Conjugation of Payloads alpha-bromopyruvate

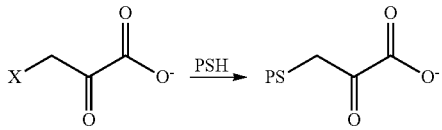

benzylbromide

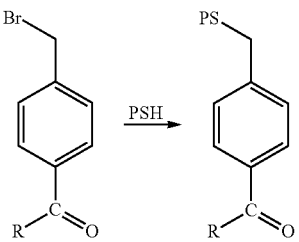

It is noteworthy that several anticancer drugs can be incorporated as payloads within the peptide template by condensing prefabricated maleimide-linked entities such as those shown in Scheme 13, with a cysteine thiol installed within the peptide template.

Scheme 13.
Maleimide-linked Prodrugs for Thiol-specified Conjugation.

Doxorubicin Prodrugs

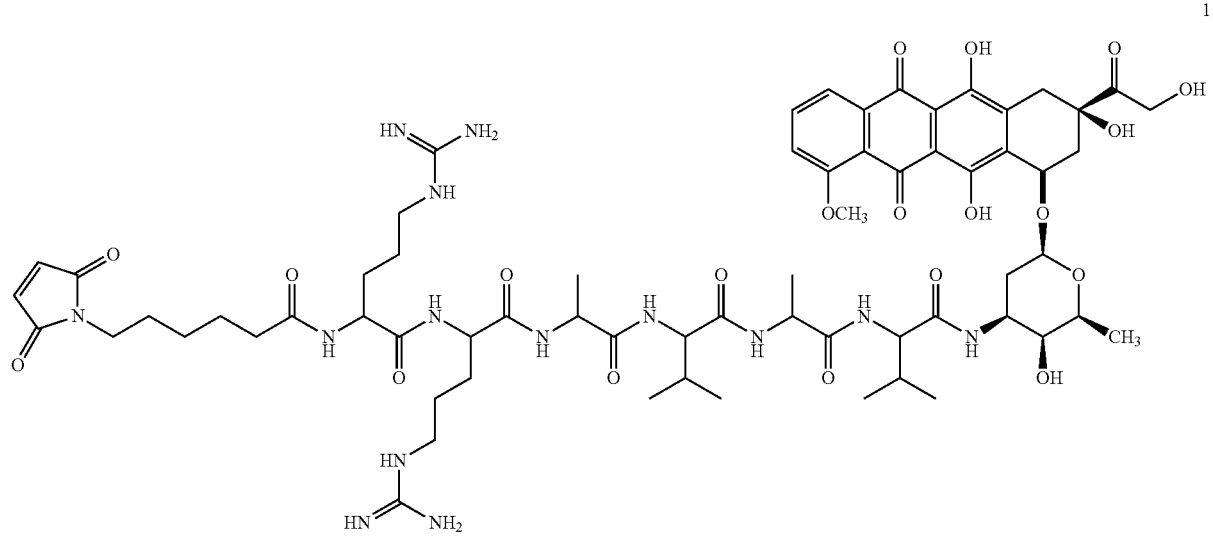

1

-continued
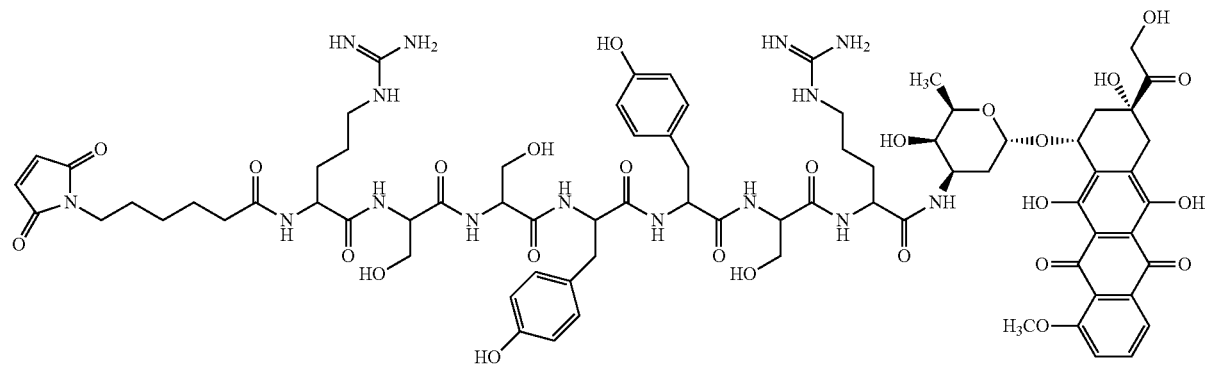
2
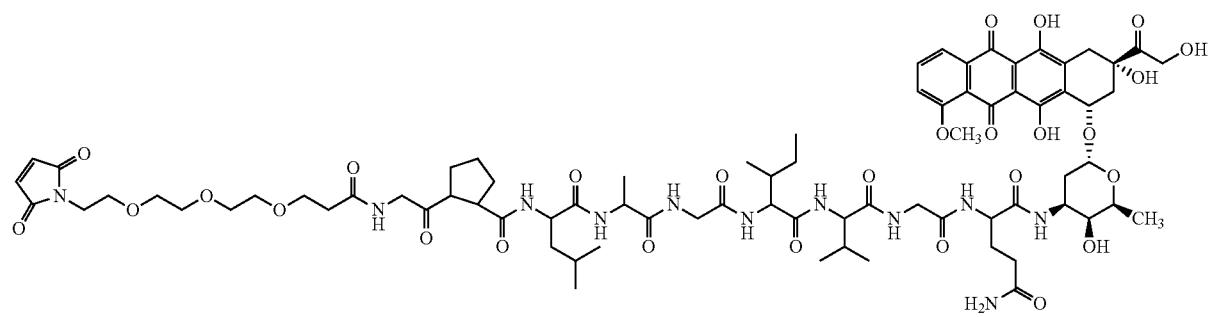
3
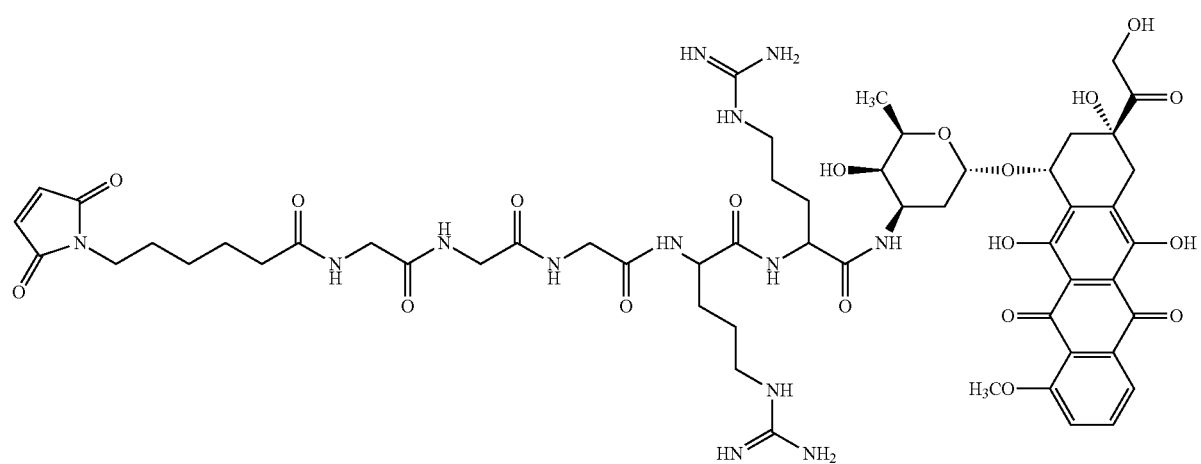
4
Methotrexate Prodrug
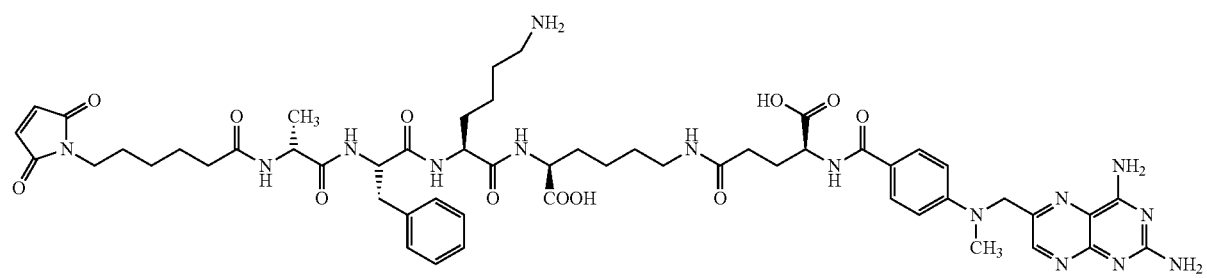
5

-continued

Camptothecin Prodrugs

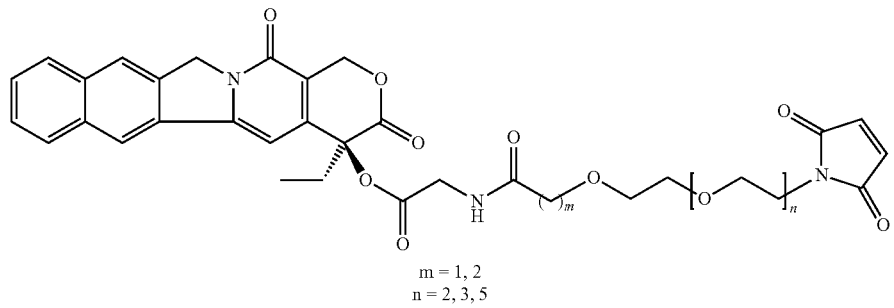

6 m = 1, 2
n = 2, 3, 5

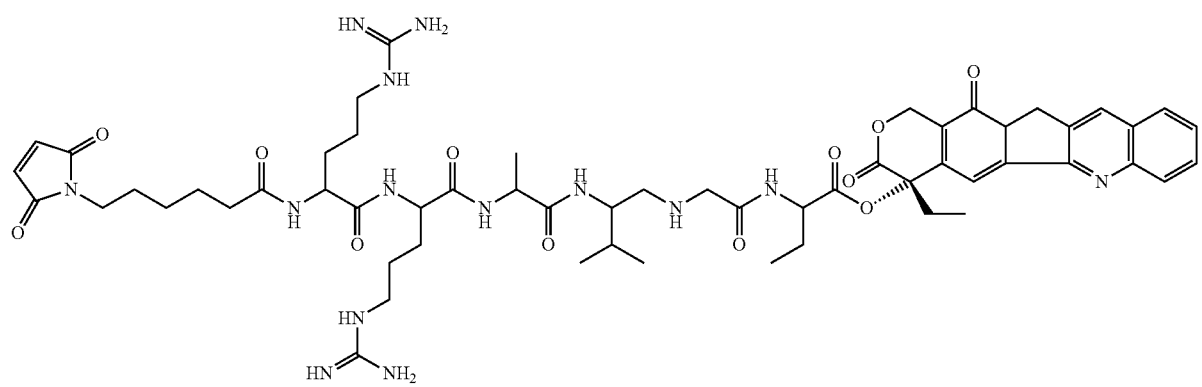

7

Platinum(II) Prodrugs

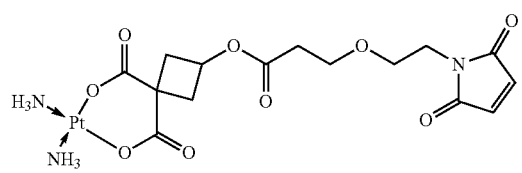

8

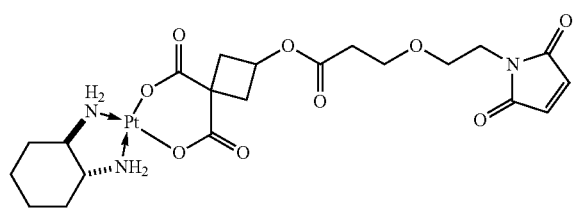

9

We have also been able to selectively functionalize free cysteines with a propargyl group in certain cysteine-containing proteins such as annexin V-128. The propargylated protein, which is convertible to 1,2,3-triazoles via cycloaddition, affords several advantages over current protocols for preparing thiol-linked conjugates, not the least of which is the in vivo stability of 1,2,3-triazoles, compared with maleimides. The triazole functionality can be installed by modifying the thiol in a two step sequence shown in Scheme 14, in which the propargyl group plays a pivotal role.

Scheme 14. Selective propargylation of free cysteine thiols in proteins.

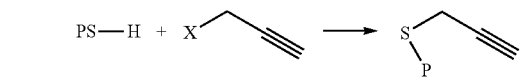

X = Br, Cl, I; SO$_3$R, R = alkyl or aryl

The introduction of an acetylenic moiety by propargyl substrates, allows 1,3-cycloadditions through an azido-substitutent (Scheme 15). The azido group has proven to be a relatively inert function in polar reactions, but generally reacts smoothly with acetylenes in 1,3-cycloadditions. Thus payloads can be introduced via the bifunctional azide linker (23) to give (24), followed by treatment with carbonyl-containing proteins (5), e.g., anthracyclines (8).

Scheme 15. Crosslinking of payloads utilizing 1,3-cycloaddition of bifunctional azide-containing linkers to propargylated thiols of proteins.

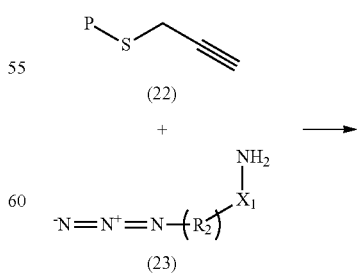

$X_1$ = O, NH, CONH, NHCONH
$R_2$ = (CH$_2$)$_m$(OCH$_2$CH$_2$)$_p$
m = 1-8: p = 0-1000

Scheme 17. Linkage of carbonyl entities to proteins via 1,3-cycloaddition of propargylated proteins and azido-carbonyl species.

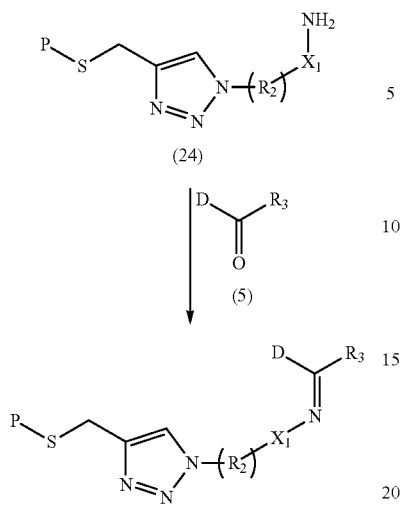

$R_1$ = H, alkyl, aryl, alkenyl, OH
$R_2$ = $(CH_2)_m(OCH_2CH_2)_p$
m = 1-8; p = 0-1000

Alternatively, the linker (23) can be condensed with payloads containing aldo- or keto-functions (5), e.g., (8), to give compounds of formula (25), followed by cycloadditions to the propargylated thiol protein (22) to give (26) (Scheme 16).

A number of chemotherapeutics are available in hydrazide form (29). Such therapeutics, exemplified by the desacetylvinblastine, can be linked to annexin proteins in the hydrazide format (Scheme 18).

Scheme 18. A vinblastine hydrazide derivative.

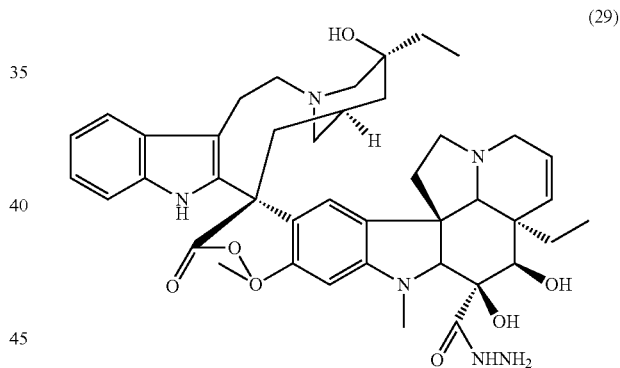

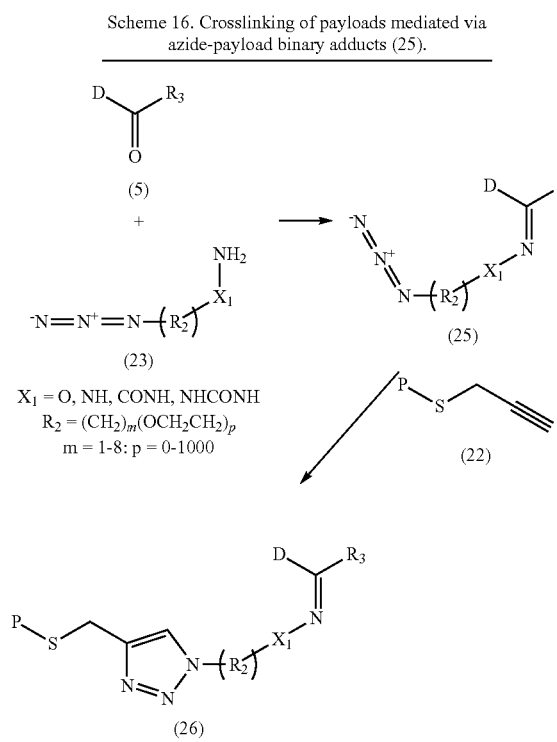

Scheme 16. Crosslinking of payloads mediated via azide-payload binary adducts (25).

$X_1$ = O, NH, CONH, NHCONH
$R_2$ = $(CH_2)_m(OCH_2CH_2)_p$
m = 1-8; p = 0-1000

Payloads may also be introduced through the use of α-azido carbonyl linkers (27) which can be condensed with (22) to give the carbonyl precursors (28) to crosslinked products (Scheme 17).

Thus α,ω-azido hydrazides, and the like, can be installed to give linkers capable of releasing payloads through cleavage of hydrazone or oxime. The α,ω-aminoxy-azides or α,ω-aminoxy-hydrazides can be prepared by several methods by chemists trained in the art. For example, ω-bromo alcohols can be used to obtain the aminoxy-azides by first displacing the bromide with azide, followed by conversion of the alcohol to the aminoxy function via Mitsunobu reactions or equivalent methods using N-hydroxy-phthalimide. The amino group can also be introduced by Ellman's method or by other methods known in the art. The α,ω-aminoxy-hydrazides are accessible via ω-bromo acids or esters, by displacement of the bromide by azide, followed by conversion of the acid to the hydrazide. The α,ω-azido carboxylic acids or amines are especially valuable for polymer therapeutics insofar as the azide can easily be installed on the polymer and then attached to an propargylated protein bearing a payload as via the 1,3-cycloaddition click chemistry. For example, polymer therapeutics can be prepared by condensing PEG amines with linkers of type (27, $R_1$=OH) the amide products of which can, in turn, be attached to a propargyl protein bearing payloads contained within P in (22), e.g., N-terminally attached anthracyclines.

A clear example of such an approach is provided below in Scheme 19 in which an anthracycline drug and a folate ligand (targeted for cancer cells in which its receptor is overexpressed) is linked site-specifically to an annexin protein. This type of conjugate can be targeted for ovarian cancer cells which both overexpress folate receptors, and expose phosphatidylserine on their cell surfaces.

Scheme 19. Crosslinking of both a folate ligand and an anthracycline anticancer agent to an annexin protein.

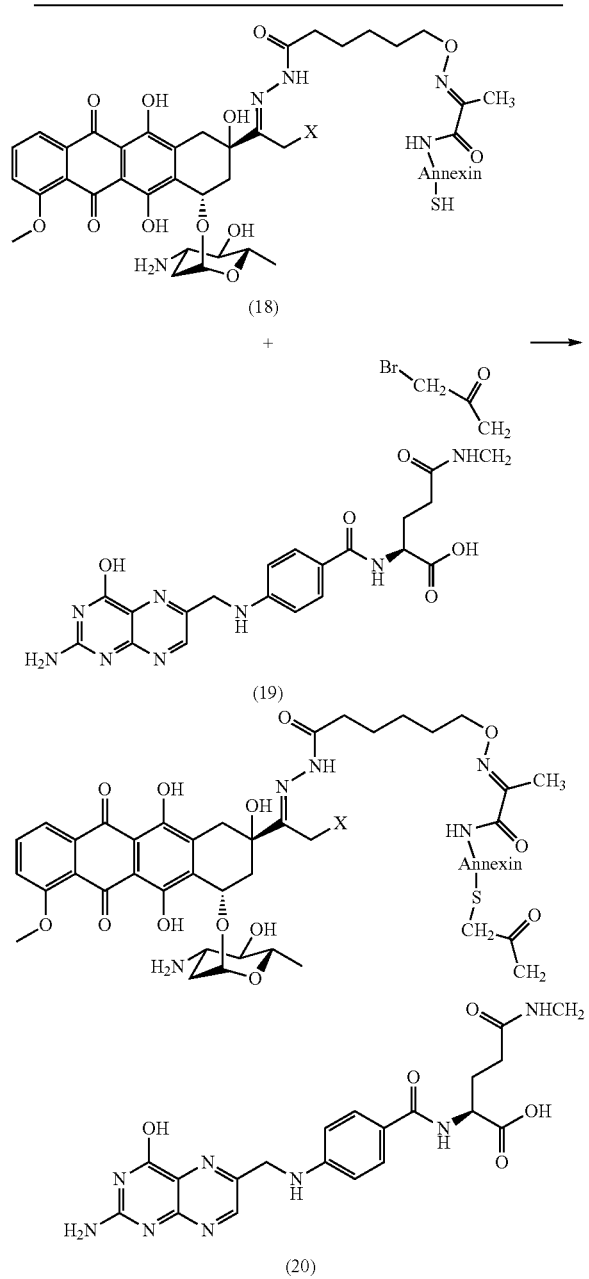

It should also be apparent that both the propargylated cysteine thiol and the N-terminal carbonyl modification of a single annexin protein can be exploited to give two equivalents of the payloaded template resulting in a conjugate of defined composition. See Scheme 20.

Scheme 20. A dual folate-anthracycline conjugate of an annexin protein in which folate is part of an extended cysteine.

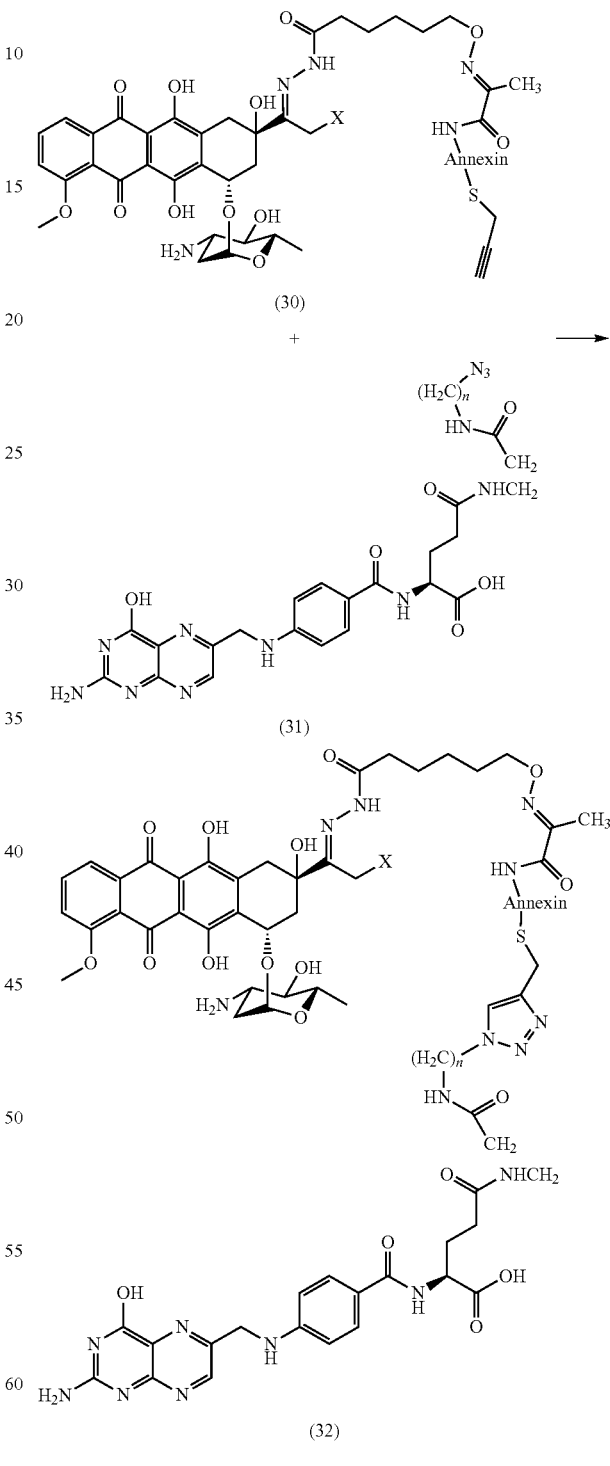

Scheme 21 provides another exemplary doubly-functionalized annexin protein.

Scheme 21. A doubly functionalized annexin protein carrying an anthracycline and a propargyl group.

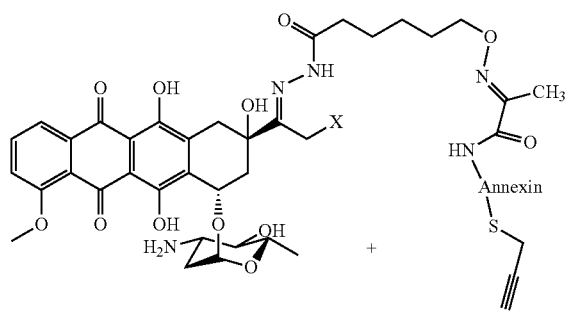

(30)

Scheme 22. Pegylation of Propargylated Proteins via 1,3-Cycloadditions of PEG-Azides.

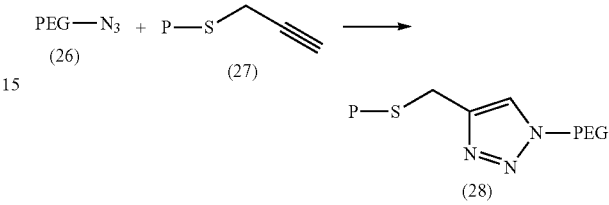

PEG = polyethylene glycol polymer; P = protein, annexin V-128 give product, Scheme 22. The cysteine of annexin V-128 also reacts with a variety of electrophilic substrates such as bromo-acetophenones, bromobenzyl substrates (not shown), or bromopyruvate that afford the possibility of crosslinking PEG (polyethylene glycol polymer) substrates to such proteins through sequences displayed in Schemes 23 and 24.

Preparation of Pegylated Compounds

Pegylation can be carried out site-specifically by first propargylating annexin V-128 and then condensing the propargylated product with a polyethylene glycol azide to Scheme 23. Crosslinking of annexin proteins to PEG polymers via a-haloacetophenone substrates.

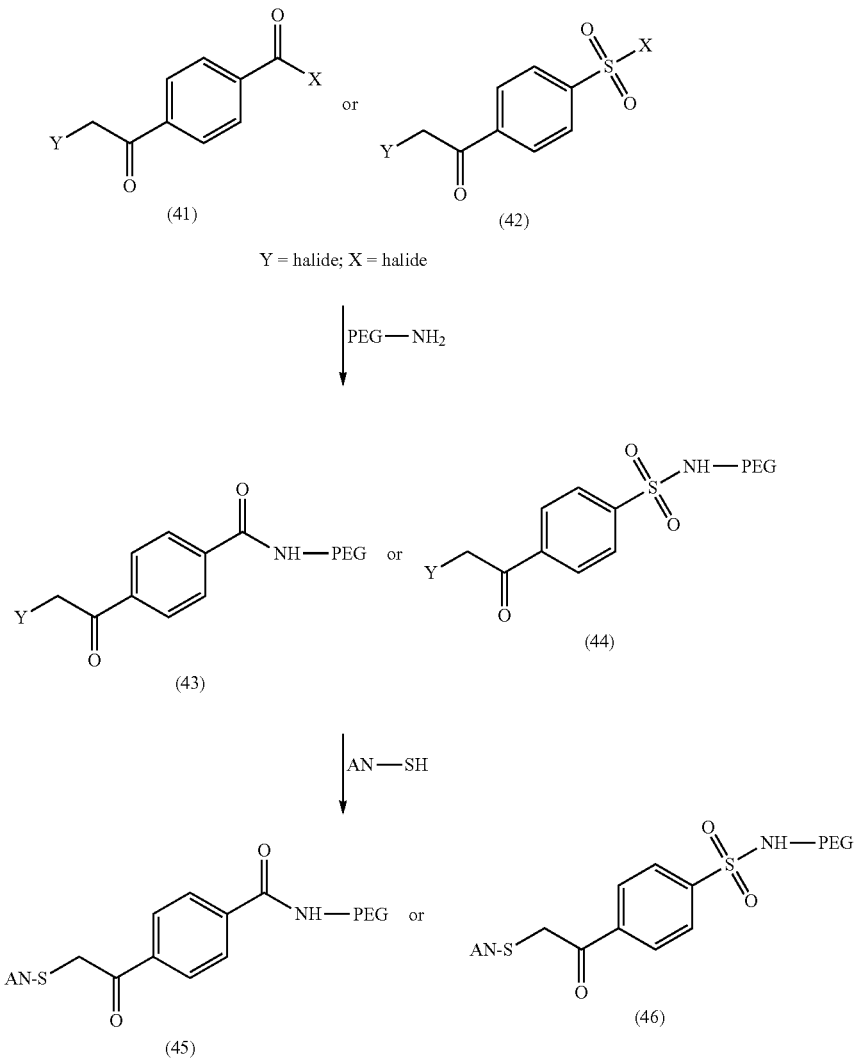

Scheme 24. Crosslinking by pyruvyl substrates of annexin proteins to PEG polymers.

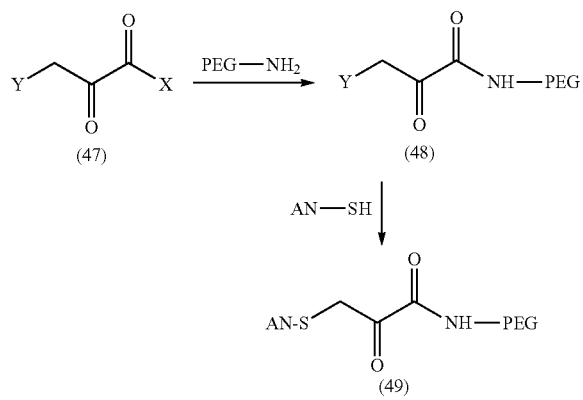

X = halide or active ester
Y = Br, Cl

Attachment of RGD Moieties

In addition to folate targeting, RGD targeting for cancer cells has proven to be effective at transporting attached entities to such cells. In keeping with these observations, peptide ligands containing the Arginine-Glycine-Aspartate (RGD) triad, which display a strong affinity and selectivity to the αVβ3 integrin, have been developed to target the tumor-associated cells expressing the αVβ3 receptors. An annexin-drug-RGD conjugate should constitute a specifically targeted therapy to such receptors, which also have a penchant annexin binding. Such conjugates can be assembled from RGD peptides such as cyclo (Arg-Gly-Asp-D-Phe-Glu) (33) which can be functionalized with various linker molecules (34) through the amino group on the α, ω-amine azide linkers. An entirely analogous route (not shown) using cyclo (Arg-Gly-Asp-D-Phe-Lys) in conjunction with linkers of type (27, $R_1$=OH), can also enable attachments to propargylated proteins, Scheme 25, (illustrated for p=0, m=n).

Scheme 25. 1,3-cycloaddition route to conjugation of RGD ligands to annexin proteins for targeting alpha (V) beta (3) receptors.

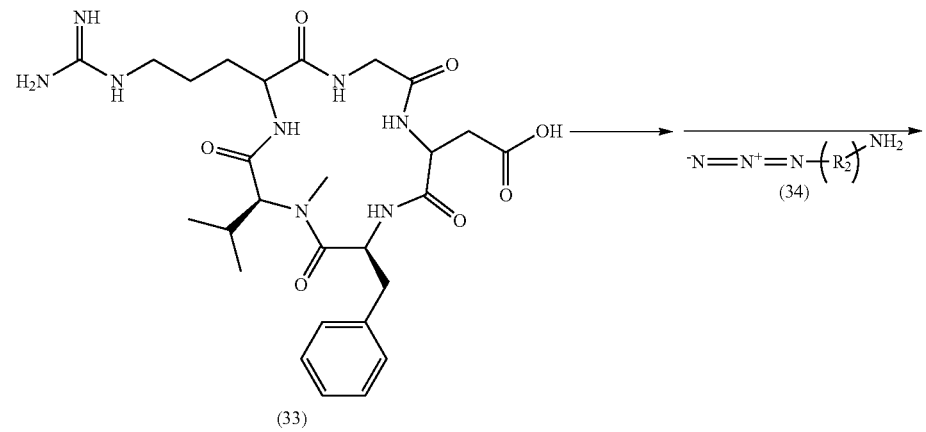

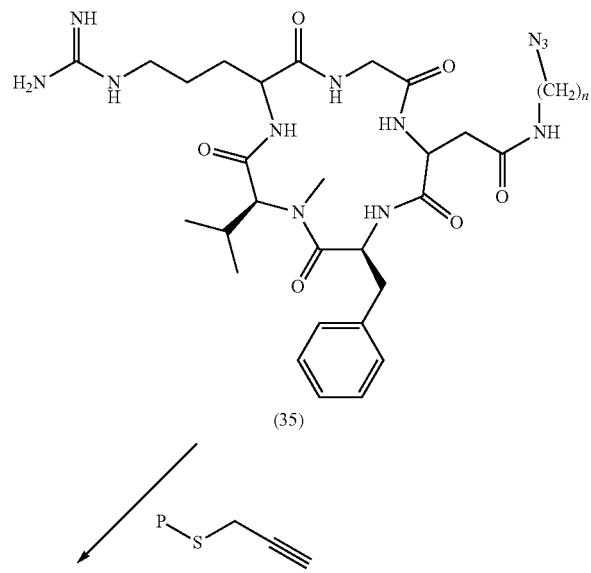

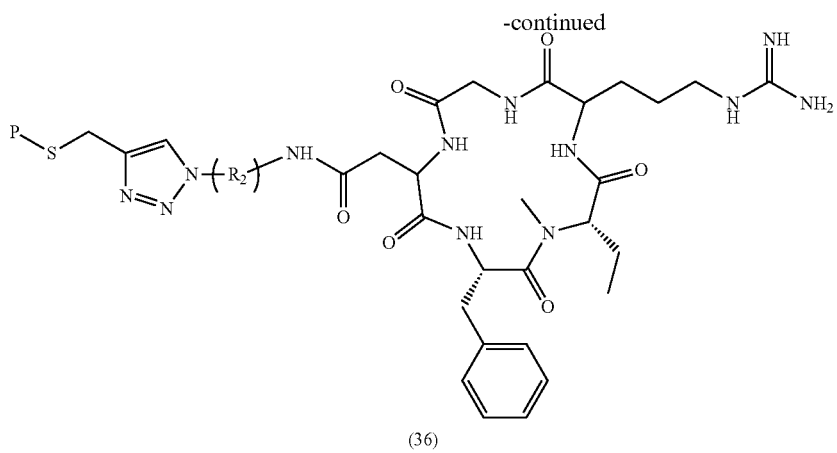

(36)

$R_2 = (CH_2)_m(OCH_2CH_2)_p$
m = 1-8; p = 0-1000

The chemistry we have invented can also be applied to payload loading of conjugates. For example 4 arm PEG amines (Scheme 26) are commercially available and protocols for monofunctionalization can be applied to generate mono-azides using ⟨,ω-azido-carboxylic acids after Ding H, Yong K T, Roy I, Hu R, Wu F, Zhao L, Law W C, Zhao W, Ji W, Liu L, Bergey E J, Prasad P N. Bioconjugated PLGA-4-arm-PEG branched polymeric nanoparticles as novel tumor targeting carriers. Nanotechnology. 2011, 22(16):165101.

Scheme 26. General structure of a 4-arm PEG polymer terminating in amines.

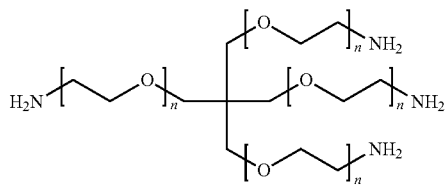

It should be noted that RGD targeting can also be applied to wounding and the repair of cells (Fong E, Tzlil S, Tirrell D A. Boundary crossing in epithelial wound healing. Proc Natl Acad Sci USA. 2010, 107(45):19302-7). Entirely analogous strategies to those above involving the attachment of thymosin β4, and RGD peptides to annexin are claimed for the repair of cells and tissues.

The unfunctionalized amino groups can then be condensed with RGD peptides to give azido-amides, and the entire assemblage can then be linked to propargylated protein by 1,3-cycloadditions reactions. The protein can also be charged with multiple drugs, through acylation routes involving the PEG amino groups.

As shown herein, the diversity and commercial availability of peptide precursors are attractive for constructing the multifunctional entities described herein. However, in principle, any template which provides the versatility to incorporate a click chemistry partner, cleavable drugs, and ligands to cell surface biomarkers, can be used as scaffolds and may offer significant advantages for a particular cancer target. Numerous examples of scaffolds have been developed for parallel synthesis that can be adapted for the multifunctional scaffolds which are subjects of this invention.

The advantages of a well characterized system are manifold. Importantly, the ability to trace effects to a single administered molecule, as opposed to an enormously complex starting mixture of protein conjugates, should afford a more reasonable basis for improving the properties of a promising lead conjugate. Systematically modifying the properties of a lead to develop structure-activity relationships has been the modus operandi in the pharmaceutical industry for decades. Indeed, an appealing aspect of the present invention is that the structures of therapeutically relevant molecules can be systematically varied in a modular way to reveal trends in activity.

Protein Dimerization

Besides chemistry dedicated toward the preparation of therapeutic proteins (e.g., annexin conjugates), this invention relates to aspects of the preparation of multimeric conjugates. In this disclosure, we describe multimers that are first prepared by recombinant methods and then chemically modified in multimer form. Homodimer of human annexin V can be prepared using well-established methods of recombinant DNA technology. Annexin molecules of homodimers can be joined through peptide bonds to a flexible linker. It is important that the dimer be able to fold in such a way that the convex surfaces of the monomer, which bind $Ca^{2+}$ and PS, can both gain access to externalized PS. Flexible linkers are known in the art, for example, (GGGGS)(n) (n=3-4), and helical linkers, (EAAAK)(n) are described in Arai, et al., Proteins. 2004, 57(4), 829-38. See also X. Chen et al., Fusion protein linkers: Property, design and functionality. Adv Drug Deliv Rev. 2012 Sep. 29. [Epub ahead of print].

The high molecular weight of the dimer exceeds the threshold of renal filtration and will result in circulation times with extended half-lives. In this invention we disclose the use of both bis-annexins that are not chemically modified, and bis-annexins that have been chemically modified to carry additional cargo such as drug pharmacophores and/or ligands that target biomarkers. Such modifications are most conveniently obtained by first constructing the payloaded template, and then in a second stage condensing the payloaded segment onto to the multimeric annexin protein.

The ability to site-specifically modify annexin proteins at both their N-termini and cysteine thiols permits the site-specific construction of a single agent bearing multiple therapeutics specifically targeted for cancer cells in dimer form. In this invention the annexin fusion protein serves as the delivery system because of its affinity for cancer cells, as well as the carrier of templates bearing drugs and other therapeutically relevant entities. Indeed, an annexin fusion protein is the delivery vehicle and the payloaded template is the cargo or freight.

The formation of annexin dimers has been approached in several ways. One approach involves the condensation of annexin proteins with benzoquinone via cysteine thiol (Cys 316) attack on the ring (Scheme 27). Whereas one equivalent of annexin V forms a mono-adduct quantitatively with 1,4-benzoquinone, it has not been possible to crosslink two molecules of annexin V using only 1,4-benzoquinone. However, the monoadduct of annexin V reacts with annexin V-128, to give a dimer containing one molecule of annexin V-128 crosslinked to annexin V. It is noteworthy that annexin V-128 is considerably more nucleophilic than annexin V, and the ability to introduce a second protein molecule on the framework of a small crosslinker is generally, considerably more difficult than forming the monoadduct. Coupling such annexin proteins through their free cysteines has the advantage of allowing other modifications of the protein to be retained on the protein framework.

Scheme 27. Crosslinking of annexin proteins by mediated by 1,4-benzoquinones.

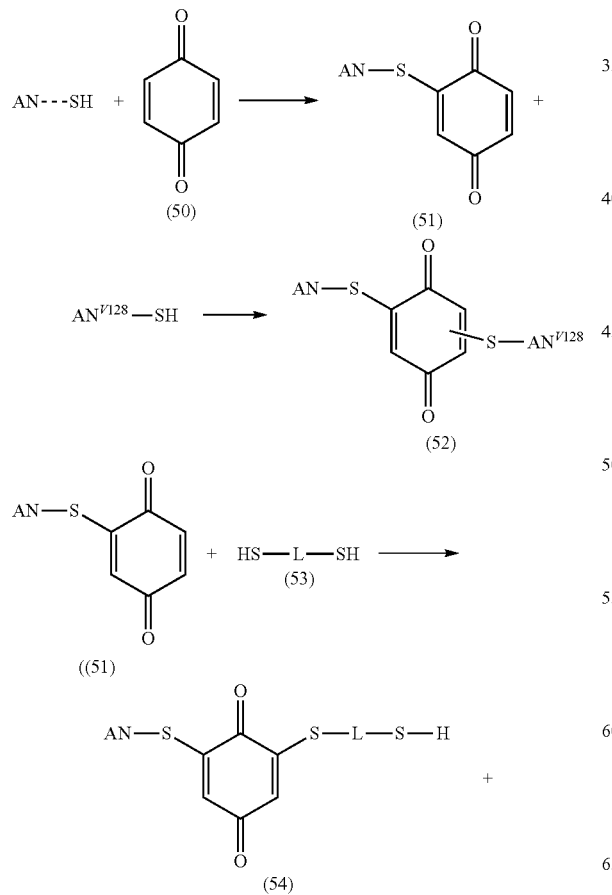

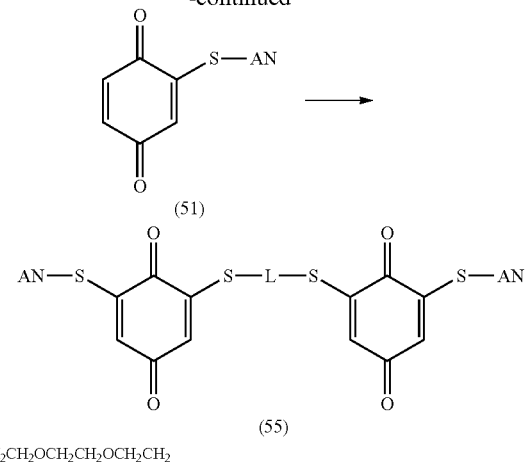

$L = CH_2CH_2OCH_2CH_2OCH_2CH_2$

We have observed the reaction of annexin V-128 to form dimers with bis-maleimides, Scheme 28. The maleimide can be used in excess to obtain the mono-labeled system, which can be used, in turn, with a second species with a reactive thiol. The reaction of annexin V-128 with bis-maleimides occurs rapidly at the protein cysteine thiol. The fact that the addition of a second equivalent of annexin V-128 is more difficult than the first equivalent allows for the site specific formation of heterodimers, if each protein or peptide has a suitably reactive thiol.

Scheme 28. Formation of annexin V-128 dimers thorugh crosslinking by bis-maleimides.

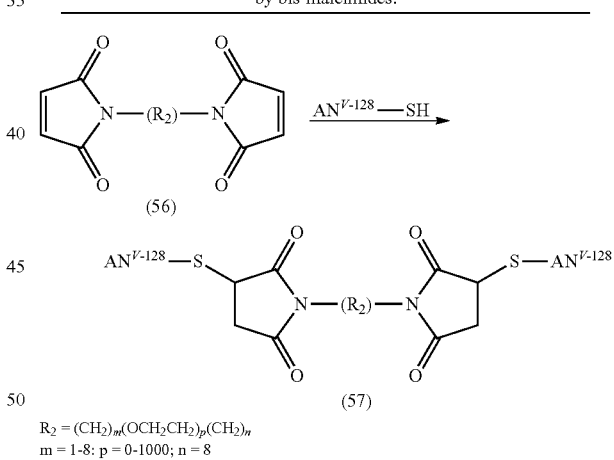

$R_2 = (CH_2)_m(OCH_2CH_2)_p(CH_2)_n$
m = 1-8: p = 0-1000; n = 8

Propargylation of cysteine thiol creates an option for crosslinking annexin V-128 through 1,3-cycloadditions to alkyne, which renders the crosslink kinetically irreversible (Scheme 29). This option depends on the reactivity of the thiol entity and the specificity of the reaction. Annexin V can be slow to react with propargyl substrates like halides and tosylates and ultimately reacts nonspecifically. By contrast, annexin V-128 can be thiol-specifically propargylated and then condensed with azide substrates. This reaction can then be exploited using bis-azide substrates such as linear α,ω-bis azides or bis-1,4-azidomethylbenzene and the like (Scheme 29). Such bis-azide systems can be prepared from the corresponding bis-diols or bis-halides.

Scheme 29. Formation of protein dimers by condensation of bis-azides with propargylated proteins.

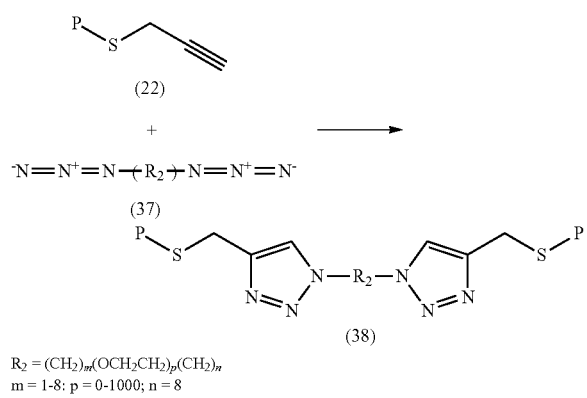

$R_2 = (CH_2)_m(OCH_2CH_2)_p(CH_2)_n$
m = 1-8; p = 0-1000; n = 8

Another sequence that can be employed involves the use of allylic substrates such as allyl bromide to first alkylate the protein thiol and then perform metathesis reactions with the proteins incorporating olefin side chains.

Yet another important feature of targeted therapy is the ability to target more than one biomarker on the surface of cells with annexin dimers modified to increase specificity for such cells. Thus annexin V-128 dimers from recombinant DNA technology can be prepared and the thiols subsequently modified with folate derivatives (cf. Figure 10) to target both phosphatidylserine and the folate receptor.

Our ability to modify the N-terminus of annexin enables us to augment the affinity of PS for annexin V by introducing additional functionality through the N-terminus in a variety of ways using linkers of the type (58) indicated in Scheme 30.

Scheme 30. Heterobifunctional linkers as key intermdiates in the crosslinking of N-terminal annexin ketoamides.

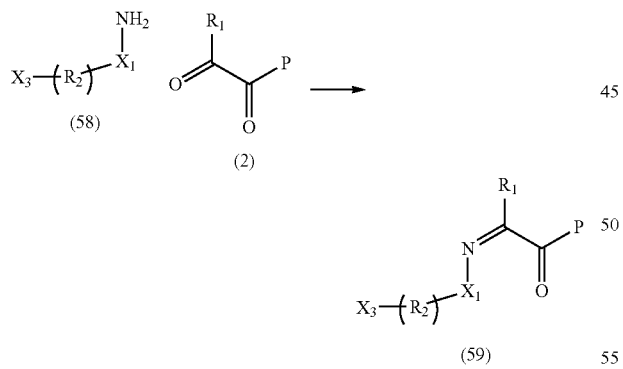

$X_1$ = O, NH, CONH
$R_2 = (CH_2)_m(OCH_2CH_2)_p$
m = 1-8; p = 0-1000, P = protein functionality
$X_3 = N_3$; SH; ———≡

Both annexin V and annexin V-128 undergo transamination to give the N-terminal ketoamides. This modification affords the opportunity for utilizing heterobifunctional linkers that attach oxime or carbazone functionality at the protein main chain and optional functional groups in the side chain terminus that can be used to connect to payloads as suggested by Figure 27. Of particular note is that protein-linker adducts can be stabilized by binding the linker irreversibly to the protein framework by reducing carbazone linkages (59, $X_1$=CONH) with sodium cyanoborohydride.

Functionalization of Multimeric Proteins

To illustrate the potential for multiple cargo, Scheme 31 portrays possible points of attack on modified bis-annexin frameworks (25). For homo-bis-annexin frameworks (those with two identical annexin sequences) that contain two solvent accessible thiols of normal thiol reactivity it is not feasible to distinguish between the thiols. However, such homo-dimers can be symmetrically substituted with payloads. An additional feature can be incorporated into the dimer framework by transamination of an annexin possessing an alanine or glycine N-terminal amino acid, or incorporating an aldehyde into the protein framework as depicted schematically in Figure 7. The carbonyl modification is subject to a variety of reactions including reductive amination. Thus, besides the thiol attachments, additional features can be introduced at the N-terminal.

Scheme 31. Illustration of three potential points of attachment in an annexin fusion protein.

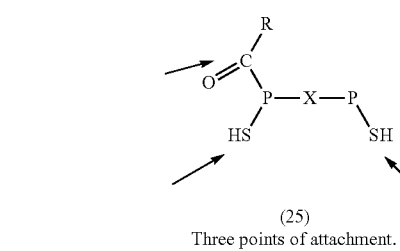

(25)
Three points of attachment.

P = annexin protein; X = linker; R = H, alkyl

We have determined that a preferred sequence for dimer modification involves propargylation of reactive thiols followed by azide cycloaddition (Scheme 32).

Scheme 32. Propargylation of annexin cysteine thiols en route to symmetrically substituted fusions proteins.

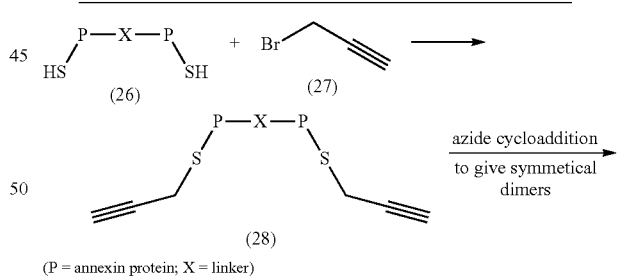

(P = annexin protein; X = linker)

Hetero-dimers can be engineered with one annexin V-128 and one annexin V amino acid sequence, for example, Scheme 33. Such hybrid dimers (29) possess differential thiol reactivity. Thus distinct cargo can be linked at the annexin V-128 thiol, which is considerably more reactive than that of annexin V and can be specifically functionalized by propargylation and benzylation, in the presence of a buried unreactive thiol of annexin V as described in Figure 9. Subsequently, Cys 316 of annexin V can be modified by an α-halo ketone or maleimide linked payloads. Thus, such dimers can be specifically functionalized at each thiol to carry diverse payloads. It is possible by judicious choice of thiol reactive entities in bis-thiol acceptors to combine dimers with reactive thiols and form tetramers.

Annexin can also be fused with peptides or proteins that augment its affinity for a specific cancer cell. Thus annexin can be fused with epidermal growth factor to capture EGF's affinity for the corresponding receptor, or fused with transferrin or human serum albumin.

Scheme 33. Formation of selectively propargylated fusion proteins (30) from heterodimer fusion proteins (29) containing a buried cysteine in an annexin unit.

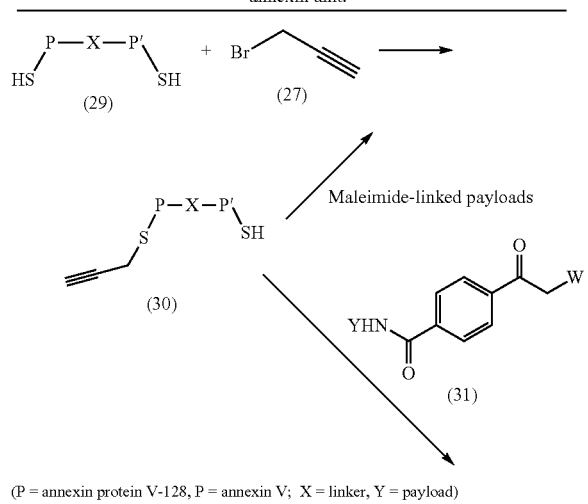

(P = annexin protein V-128, P = annexin V; X = linker, Y = payload)

It should be pointed out that copper free click chemistry can be performed to give annexin conjugates as depicted in Scheme 34. In this exemplary sequence commercially available cyclooctynes, exemplified by (33) preferentially reacts with the acid bromide (or an active ester) of (34), which can then be combined with thiol-containing proteins such as annexins or HSA. The intermediates (34) and (35) are invaluable and can be combined with azides or bis-azides in various modes to form drug conjugates or dimers (not shown). It is to be noted that the use of bromobenzyl substrates and bromoacetamide (not shown) substrates are privileged synthetic motifs that lead to particularly stable thioether C—S bonds.

Scheme 34. Formation of a cyclooctyne intermediate (35) for attachment of protein thiols, and azide-linked therapeutically-relevant cargo by copper-free protocols.

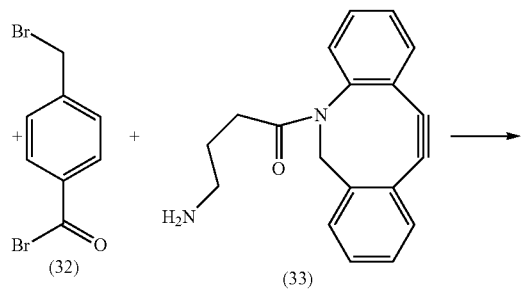

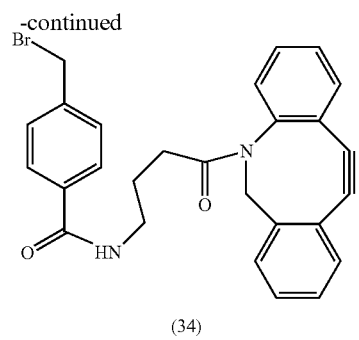

As well, the cyclooctyne (33) can be combined with activated dicarboxylic acids to give the bis-cyclooctyne which can be used as an intermediate to form cargo carrying tetramers by reaction of dimers substituted with azide functions (not shown).

Solid Phase Protein Synthesis

By way of example, one may consider the construction of a dimeric annexin conjugate that carries a number of chemotherapeutic entities in prodrug form, and a folate moiety targeted to specific cancer cells overexpressing folate receptors.

Such an agent can be assembled using conventional techniques and commercially available materials as exemplified in Scheme 35. (Entirely analogous schemes using amino acid and peptide spacers for non-contiguous payloads are easily prepared by chemists trained in the art.) First, using solid phase protein synthesis (SPPS), two molecules of the commercially available O-methyl glutamate ester ((1), shown bound to a solid support) can be coupled to give the dipeptide diester (2). A third molecule of amino acid, the folate-modified azidolysine (not shown), can be coupled to give the tripeptide (4), or alternatively treatment of (2) with the t-Boc-protected azidolysine amino acid (3) followed by t-Boc-deprotection and acylation with folate, can give (4).

After treatment with hydrazine the glutamate esters are converted to the corresponding hydrazides and then released from the solid support to form (5). Solution chemistry can then be used to prepare the bis-doxorubicin product (6). The latter "payloaded" system can, in principle, then be combined with alkynylated proteins in click chemistry fashion to give a multi-therapeutic agent. The agent possesses the combined properties of annexin with the linked peptide cargo, specifically targeted for cancer cells expressing PS on their outer surfaces and overexpressing folate receptors. This protocol is capable of significant variations including varying the ligand targeting biomarkers, the anti-cancer drugs, as well as substituting amino acids with protected aminoxy side chains to prepare oxime-linked drug conjugates. (To effect site specific reactions with the payloaded entity, complementary reaction functionality is required, which is not part of the normal repertoire of protein synthesis. To realize the necessary site-specific conjugation between template and dimeric annexin we have invented methodology, which allows for the installation of alkyne functionality in annexin proteins (vide infra).)

Scheme 35. Exemplary Sequential Coupling of Amino Acids for Constructing Templates for Therapeutically Relevant Payloads.

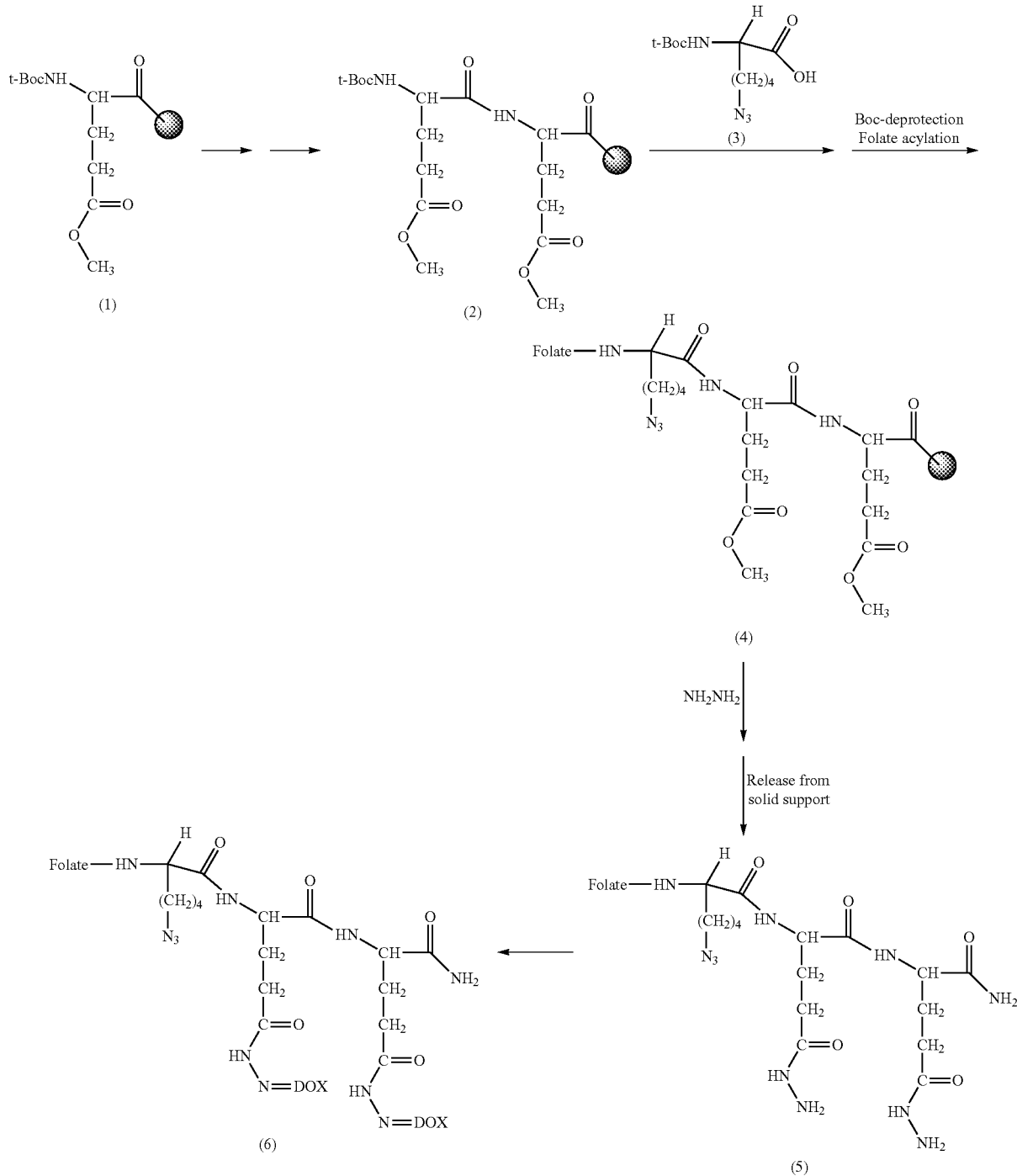

This template approach can be extended to payloaded peptide templates bearing more than two identical drug entities, by sequential addition of n-amino acids designed to carry drug-modified side chains. Fmoc chemistry can also be used to attach drug-modified amino acids directly to the growing peptide chain.

In a variant of the approach described above, Scheme 36, two different chemotherapeutic agents can be assembled on the template. Since both Fmoc- and t-Boc-protected hydrazines are available, the differentially protected bis-hydrazides (7) and (8) can be assembled and ultimately, orthogonally deprotected. Using standard techniques of SPPS the modified template bearing two distinct chemotherapeutic agents (9) and (10) (e.g., doxorubicin and taxol) can be constructed in two distinct configurations, regiospecifically. It is to be noted that acid sensitive hydrazone linkers have been used for delivery of several drug types including taxols, anthracyclines, and Vinca alkaloids. Analogous hydrolytically or enzymatically labile linkages incorporating taxols, platinum drugs, camptothecins, for example can be exploited using a template strategy disclosed above.

Scheme 36. Structural Relationship between Differentially Protected Hydrazides and Regioisomers of Payloaded Templates.

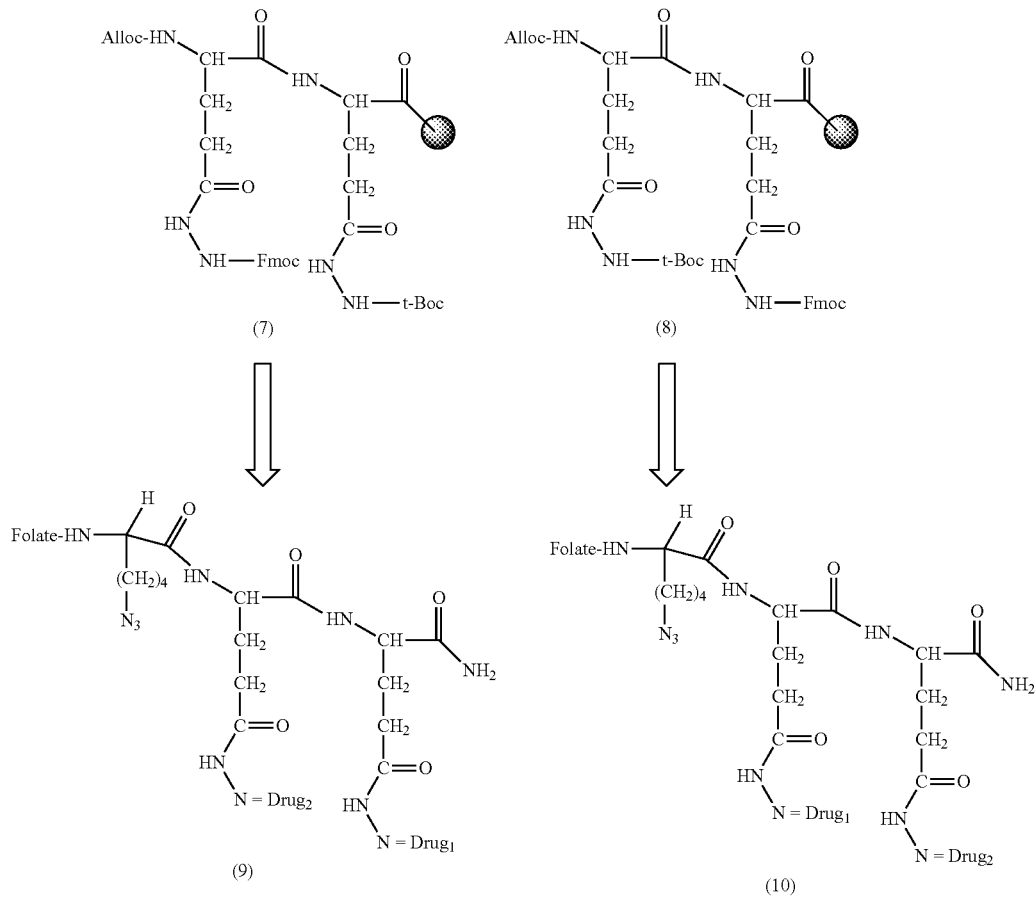

To effect site specific reactions with the payloaded entity, complementary reaction functionality is required, which is not part of the normal repertoire of protein synthesis. We have invented methodology, which allows for the installation in annexin proteins of complementary functionality: alkyne functionality, at appropriate cysteine thiols, e.g., annexin V-128, or at the N-termini of annexins, which can be applied to annexin fusion proteins as well, e.g., dimers.

The anticancer agent and the ligand may be directly coupled together or indirectly coupled together via a linker. In addition, the anticancer agent may be conjugated to PEG, or the conjugate may be encapsulated in a liposome.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A pharmaceutical composition comprising a therapeutic compound having a structure according to formula (I),

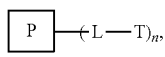

wherein

P represents a multimer of proteins, wherein P comprises 2, 3, or 4 proteins having a solvent accessible thiol, wherein at least one of said proteins has at least 90% sequence identity to SEQ ID NO: 1;

each L independently represents an organic linker group;

each T independently represents a therapeutic agent, a protein, or a ligand to a biomarker;

n is an integer from 0-10; and wherein each L-T moiety present is site-specifically attached to an amino acid residue of P, wherein the compound according to formula (I) represents at least about 75% of biologically active proteins present in the composition, wherein said proteins in P are linked via a chemical modification to said solvent accessible thiol in said proteins; and wherein subunits in P are linked together by:
(a) a linker having the structure

XXI

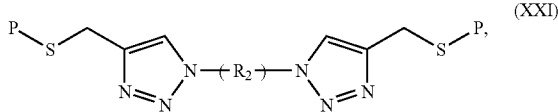
(XXI)

wherein $R_2$ is $(CH_2)_m(OCH_2CH_2)_p$, wherein m is an integer from 1 to 8, and p is an integer from 0 to 1000; or (b) a linker formed through a reaction between solvent accessible thiols in said subunits and a compound having the structure

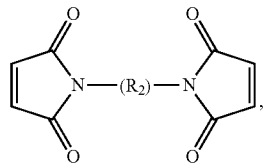
(XXXII)

wherein $R_2$ is $(CH_2)_m(OCH_2CH_2)_p$, where m is an integer between from 1 to 8, and p is an integer between from 0 to 1000.

2. The pharmaceutical composition of claim 1, wherein n is an integer from 1-10.

3. The pharmaceutical composition of claim 1, wherein P comprises at least one protein having at least 90% sequence identity to SEQ ID NO: 1 and at least one protein selected from the group consisting of a synaptotagmin protein, lactadherin, alpha-fetoprotein, a transferrin protein, human serum albumin, integrin αvβ3, and integrin αvβ5.

4. The pharmaceutical composition of claim 1, wherein P comprises a protein having at least 95% sequence identity to SEQ ID NO: 1.

5. The pharmaceutical composition of claim 1, wherein P comprises annexin V-128.

6. The pharmaceutical composition of claim 1, wherein P comprises an annexin protein modified to include an RGD sequence.

7. The pharmaceutical composition of claim 1, wherein P comprises an annexin protein modified to include an aldehyde or ketone; or
wherein P comprises an annexin protein modified to include a carbonyl group on the N-terminal residue, said carbonyl group capable of undergoing reductive amination with an aromatic amine.

8. The pharmaceutical composition of claim 1, wherein n is 0.

9. The pharmaceutical composition of claim 1, wherein each L is, independently, a linker group selected from the group consisting of
C1-C20 alkylene;
polyethylene glycol;
a peptide having between 2-25 amino acid residues;
a peptoid having between 2-25 residues;
a linker formed from an α,ω-bifunctional compound, wherein each terminal functional group of the bifunctional compound is selected, independently, from aminooxy, hydrazine, semicarbazide, N-hydroxysuccinimide ester, maleimide, thiol, alkyne, azide, aldehyde, and alkoxylamine;
a linker formed from a bis-anhydride, bis-imidate, or bis-carbonyl imidazole moiety; or
a linker formed from a cycloaddition reaction between an alkyne moiety and an azide.

10. The pharmaceutical composition of claim 9, wherein each L is, independently, a linker group selected from the group consisting of:
a linker formed from a bis-aminooxyalkane $NH_2O(CH_2)_nONH_2$ where n is an integer between 1-20;
a peptoid or peptide having between 2-15 residues, optionally said peptoid or peptide comprises at least one amino acid in the D-configuration, a residue containing a thiol side chain, a residue comprising a nucleophilic nitrogen containing side chain, a residue having a sidechain comprising a hydrazine or aminooxy group, a residue having a side chain comprising a carboxylic acid or carboxylic ester, or any combination thereof;
a linker formed from a bis-hydrazino-alkane $NH_2NH(CH_2)_nONHNH_2$ where n is an integer between 1-20;
a linker formed from a bis-semicarbazide-alkane $NH_2NRCO(CH_2)_nOCNRNH_2$ where n is an integer between 1-20;
a linker formed from α,ω-bifunctional compound, wherein one terminal functional group is an azide, and the other terminal group is an aminooxy or a hydrazine;
a linker comprising polyethylene glycol polymer comprising up to 1000 monomeric moieties; and
a linker comprising a triazole.

11. The pharmaceutical composition of claim 1, wherein said therapeutic protein comprises one or more T groups independently selected from a chelate, protein, vitamin, enzyme, peptide, peptoid, antibody, drug, prodrug, a ligand to biomarker, and a stimulator of efferocytosis.

12. A method of treating cancer in a patient, said method comprising administering to said patient an effective amount of the pharmaceutical composition of claim 1.

13. A pharmaceutical composition comprising a therapeutic compound-having a structure according to formula (I),

(I)

wherein
P represents a multimer of proteins, wherein P comprises 2, 3, or 4 proteins having a solvent accessible thiol, wherein at least one of said proteins has at least 90% sequence identity to SEQ ID NO: 1;
each L independently represents an organic linker group;
each T independently represents a therapeutic agent, a protein, or a ligand to a biomarker;
n is an integer from 1-10; and
wherein each L-T moiety present is site-specifically attached to an amino acid residue of P,
wherein the compound according to formula (I) represents at least about 75% of biologically active proteins present in the composition,
wherein said proteins in P are linked via a chemical modification to said solvent accessible thiol in said proteins; and wherein each L is, independently, a linker group selected from the group consisting of:
a linker formed from a bis-aminooxyalkane NH$_2$O(CH$_2$)$_n$ONH$_2$ where n is an integer between 1-20;
a peptoid or peptide having between 2-15 residues, optionally said peptoid or peptide comprises at least one amino acid in the D-configuration, a residue containing a thiol side chain, a residue comprising a nucleophilic nitrogen containing side chain, a residue having a sidechain comprising a hydrazine or aminooxy group, a residue having a side chain comprising a carboxylic acid or carboxylic ester, or any combination thereof;
a linker formed from a bis-hydrazino-alkane NH$_2$NH(CH$_2$)$_n$ONHNH$_2$ where n is an integer between 1-20;
a linker formed from a bis-semicarbazide-alkane NH$_2$NRCO(CH$_2$)$_n$OCNRNH$_2$ where n is an integer between 1-20;
a linker formed from α,ω-bifunctional compound, wherein one terminal functional group is an azide, and the other terminal group is an aminooxy or a hydrazine;
a linker comprising polyethylene glycol polymer comprising up to 1000 monomeric moieties; and
a linker comprising a triazole.

14. The pharmaceutical composition of claim 13, wherein P comprises a protein having at least 95% sequence identity to SEQ ID NO: 1.

15. The pharmaceutical composition of claim 13, wherein P comprises annexin V-128.

16. The pharmaceutical composition of claim 13, wherein said therapeutic protein comprises one or more T groups independently selected from a chelate, protein, vitamin, enzyme, peptide, peptoid, antibody, drug, prodrug, a ligand to biomarker, and a stimulator of efferocytosis.

* * * * *

SEQUENCE LISTING

<160> NUMBER OF SEQ ID NOS: 1

<210> SEQ ID NO 1
<211> LENGTH: 320
<212> TYPE: PRT
<213> ORGANISM: Homo sapiens

<400> SEQUENCE: 1

-continued

```
Met Ala Gln Val Leu Arg Gly Thr Val Thr Asp Phe Pro Gly Phe Asp
1               5                   10                  15
Glu Arg Ala Asp Ala Glu Thr Leu Arg Lys Ala Met Lys Gly Leu Gly
                20                  25                  30
Thr Asp Glu Glu Ser Ile Leu Thr Leu Leu Thr Ser Arg Ser Asn Ala
                35                  40                  45
Gln Arg Gln Glu Ile Ser Ala Ala Phe Lys Thr Leu Phe Gly Arg Asp
    50                  55                  60
Leu Leu Asp Asp Leu Lys Ser Glu Leu Thr Gly Lys Phe Glu Lys Leu
65                  70                  75                  80
Ile Val Ala Leu Met Lys Pro Ser Arg Leu Tyr Asp Ala Tyr Glu Leu
                85                  90                  95
Lys His Ala Leu Lys Gly Ala Gly Thr Asn Glu Lys Val Leu Thr Glu
                100                 105                 110
Ile Ile Ala Ser Arg Thr Pro Glu Glu Leu Arg Ala Ile Lys Gln Val
                115                 120                 125
Tyr Glu Glu Glu Tyr Gly Ser Ser Leu Glu Asp Asp Val Val Gly Asp
    130                 135                 140
Thr Ser Gly Tyr Tyr Gln Arg Met Leu Val Val Leu Leu Gln Ala Asn
145                 150                 155                 160
Arg Asp Pro Asp Ala Gly Ile Asp Glu Ala Gln Val Glu Gln Asp Ala
                165                 170                 175
Gln Ala Leu Phe Gln Ala Gly Glu Leu Lys Trp Gly Thr Asp Glu Glu
                180                 185                 190
Lys Phe Ile Thr Ile Phe Gly Thr Arg Ser Val Ser His Leu Arg Lys
                195                 200                 205
Val Phe Asp Lys Tyr Met Thr Ile Ser Gly Phe Gln Ile Glu Glu Thr
    210                 215                 220
Ile Asp Arg Glu Thr Ser Gly Asn Leu Glu Gln Leu Leu Leu Ala Val
225                 230                 235                 240
Val Lys Ser Ile Arg Ser Ile Pro Ala Tyr Leu Ala Glu Thr Leu Tyr
                245                 250                 255
Tyr Ala Met Lys Gly Ala Gly Thr Asp Asp His Thr Leu Ile Arg Val
                260                 265                 270
Met Val Ser Arg Ser Glu Ile Asp Leu Phe Asn Ile Arg Lys Glu Phe
                275                 280                 285
Arg Lys Asn Phe Ala Thr Ser Leu Tyr Ser Met Ile Lys Gly Asp Thr
    290                 295                 300
Ser Gly Asp Tyr Lys Lys Ala Leu Leu Leu Leu Cys Gly Glu Asp Asp
305                 310                 315                 320
```